US008412306B2

(12) United States Patent
Kurpad et al.

(10) Patent No.: US 8,412,306 B2
(45) Date of Patent: Apr. 2, 2013

(54) VOLTAGE STANDING WAVE SUPPRESSION FOR MR-GUIDED THERAPEUTIC INTERVENTIONS

(75) Inventors: Krishna N. Kurpad, Madison, WI (US); Orhan Unal, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1182 days.

(21) Appl. No.: 11/728,874

(22) Filed: Mar. 27, 2007

(65) Prior Publication Data

US 2008/0208031 A1 Aug. 28, 2008

Related U.S. Application Data

(60) Provisional application No. 60/904,158, filed on Feb. 28, 2007.

(51) Int. Cl.
*A61B 5/05* (2006.01)
(52) U.S. Cl. .......................... 600/423; 600/411; 600/424
(58) Field of Classification Search .................. 600/411, 600/420, 424, 431, 433–434, 423
See application file for complete search history.

(56) References Cited

U.S. PATENT DOCUMENTS

| | | |
|---|---|---|
| 4,855,353 A | 8/1989 | Kurami et al. |
| 4,986,980 A | 1/1991 | Jacobsen |
| 5,039,512 A | 8/1991 | Kraft et al. |
| 5,087,440 A | 2/1992 | Cacheris et al. |
| 5,098,692 A | 3/1992 | Gries et al. |
| 5,264,634 A | 11/1993 | Becker et al. |
| 5,294,886 A | 3/1994 | Duerr |
| 5,318,025 A | 6/1994 | Dumoulin et al. |
| 5,583,206 A | 12/1996 | Snow et al. |
| 5,627,079 A | 5/1997 | Gardella, Jr. et al. |
| 5,715,822 A | 2/1998 | Watkins et al. |
| 5,744,958 A | 4/1998 | Werne |
| 5,817,292 A | 10/1998 | Snow et al. |

(Continued)

FOREIGN PATENT DOCUMENTS

| | | |
|---|---|---|
| AU | 758331 | 12/1999 |
| EP | 0331616 A2 | 9/1989 |

(Continued)

OTHER PUBLICATIONS

United States Office Action for U.S. Appl. No. 09/105,033 dated Oct. 18, 2000 (7 pages).

(Continued)

*Primary Examiner* — Brian Casler
*Assistant Examiner* — Rajeev Siripurapu

(57) ABSTRACT

A system and method of tracking a medical device and generating an image of a target area. The medical device includes a tracking device to create an imaging field-of-view that extends beyond the tip of the medical device while allowing the tip of the medical device to be visualized. The medical device further includes an imaging/visualization device to create an imaging field from the point of view of the medical device. A voltage standing wave suppression device is formed on the exterior surface of the medical device to prevent the formation of voltage standing waves and localized tissue heating. The voltage standing wave suppression device includes two cable traps spaced apart from one another with each cable trap being formed of a closely packed coiled region of a conductor extending the length of the medical device.

32 Claims, 48 Drawing Sheets

U.S. PATENT DOCUMENTS

| | | | |
|---|---|---|---|
| 5,932,188 | A | 8/1999 | Snow et al. |
| 5,980,862 | A | 11/1999 | Meade et al. |
| 6,026,316 | A | 2/2000 | Kucharczyk et al. |
| 6,061,587 | A | 5/2000 | Kucharczyk et al. |
| 6,171,240 | B1 | 1/2001 | Young et al. |
| 6,246,896 | B1 | 6/2001 | Dumoulin et al. |
| 6,317,091 | B1 | 11/2001 | Oppelt |
| 6,361,759 | B1 | 3/2002 | Frayne et al. |
| 6,395,299 | B1 | 5/2002 | Babich et al. |
| 6,470,204 | B1 | 10/2002 | Uzgiris et al. |
| 6,487,437 | B1 * | 11/2002 | Viswanathan et al. ........ 600/423 |
| 6,516,213 | B1 | 2/2003 | Nevo |
| 6,741,822 | B2 | 5/2004 | Ishiguro et al. |
| 6,778,689 | B1 | 8/2004 | Aksit et al. |
| 6,799,067 | B2 | 9/2004 | Pacetti et al. |
| 6,845,259 | B2 | 1/2005 | Pacetti et al. |
| 6,871,086 | B2 | 3/2005 | Nevo et al. |
| 6,876,198 | B2 | 4/2005 | Watanabe et al. |
| 6,882,149 | B2 | 4/2005 | Nitz |
| 6,892,090 | B2 | 5/2005 | Verard et al. |
| 6,896,873 | B2 | 5/2005 | Frayne et al. |
| 6,896,874 | B2 | 5/2005 | Li et al. |
| 6,898,454 | B2 | 5/2005 | Atalar et al. |
| 2002/0040185 | A1 | 4/2002 | Atalar et al. |
| 2002/0095084 | A1 | 7/2002 | Vrijheid et al. |
| 2003/0077225 | A1 | 4/2003 | Laurent et al. |
| 2003/0100830 | A1 | 5/2003 | Zhong et al. |
| 2003/0120146 | A1 | 6/2003 | Dumoulin |
| 2003/0135110 | A1 | 7/2003 | Leussler |
| 2003/0187347 | A1 | 10/2003 | Nevo et al. |
| 2004/0024301 | A1 | 2/2004 | Hockett et al. |
| 2004/0171934 | A1 | 9/2004 | Khan et al. |
| 2004/0253292 | A1 | 12/2004 | Unal et al. |
| 2005/0165301 | A1 | 7/2005 | Smith et al. |
| 2005/0171425 | A1 | 8/2005 | Burke |
| 2006/0206105 | A1 | 9/2006 | Chopra et al. |
| 2007/0156042 | A1 | 7/2007 | Unal et al. |
| 2007/0167726 | A1 | 7/2007 | Unal et al. |
| 2008/0114235 | A1 * | 5/2008 | Unal et al. .................... 600/411 |
| 2008/0183070 | A1 | 7/2008 | Unal et al. |

FOREIGN PATENT DOCUMENTS

| | | |
|---|---|---|
| EP | 0928972 A2 | 7/1999 |
| EP | 1082143 | 3/2001 |
| EP | 1102074 | 5/2001 |
| GB | 2353039 A2 | 2/1999 |
| JP | 10-080414 | 3/1998 |
| JP | 2001500501 | 1/2001 |
| WO | 9200748 A1 | 1/1992 |
| WO | 9408629 A1 | 4/1994 |
| WO | 9423782 A1 | 10/1994 |
| WO | 9505669 A1 | 2/1995 |
| WO | 9524225 A1 | 9/1995 |
| WO | 9600588 A1 | 1/1996 |
| WO | 9719362 A1 | 5/1997 |
| WO | 98/10797 | 3/1998 |
| WO | 9828258 A1 | 7/1998 |
| WO | 9910035 A2 | 3/1999 |
| WO | WO 99/18852 | 4/1999 |
| WO | 9960920 A2 | 12/1999 |
| WO | 01/56469 | 8/2001 |
| WO | 0181460 A1 | 11/2001 |
| WO | 0222186 A1 | 3/2002 |
| WO | 03/045457 | 6/2003 |
| WO | 03094975 A1 | 11/2003 |
| WO | 03098245 A1 | 11/2003 |
| WO | WO 2004/093921 | 11/2004 |
| WO | 2005037143 A1 | 4/2005 |
| WO | 2005/101045 | 10/2005 |
| WO | WO 2005/109025 | 11/2005 |
| WO | WO 2006031317 A2 * | 3/2006 |
| WO | WO 2007/078405 | 7/2007 |
| WO | WO 2007/078409 | 7/2007 |
| WO | WO 2008/060589 | 5/2008 |
| WO | WO 2008/094855 | 8/2008 |
| WO | 2008/106201 | 9/2008 |
| WO | 2008/106212 | 9/2008 |

OTHER PUBLICATIONS

United States Office Action for U.S. Appl. No. 09/105,033 dated May 7, 2001 (9 pages).

United States Office Action for U.S. Appl. No. 10/096,368 dated Sep. 10, 2002 (9 pages).

United States Office Action for U.S. Appl. No. 10/421,584 dated Sep. 28, 2005 (10 pages).

United States Office Action for U.S. Appl. No. 11/322,451 dated Jul. 9, 2009 (13 pages).

Burl, M. et al., "Tuned fiducial markers to identify body locations with minimal perturbation of tissue magnetization," Magn. Reson. Med. (1996) 36(3):491-493.

Fried, M.P. et al., "Image guides surgery in a new magnetic resonance suite: preclinical considerations," Laryngoscope (1996) 106(4):411-417.

Jiang, X. et al., "Novel magnetic resonance signal enhancing coating material," Adv. Materials (2001) 13(7):490-493 (XP001044106).

Kandarpa, K. et al., "Prototype miniature endoluminal MR imaging catheter," J. Vasc. Int. Radio. (1993) 4:419-427.

Kende, A.S. et al., "Synthesis of some novel functionalized double Michael acceptors based on bis(vinylsulfonyl) methane (BVSM)," retrieved from STN, Database accession No. 1996:721056, XPP002281329 abstract.

Kim, S.H. et al., "Lateral diffusion of amphiphiles and macromolecules at the air/water inface," J. Phys. Chem. (1992) 96:4034.

Kochli, V.D. et al., "Vascular interventions guided by ultrafast MR imaging: evaluation of different materials," Magn. Reson. Med. (1994) 31(3):309-314.

Korosec, F.R. et al., "Time-resolved contrast-enhanced 3D MR angiography," Magn. Reson. Medicine (1996) 36:345-351.

Ladd, M.E. et al., "Vascular guidewire visualization for MR fluoroscopy," Proc. ISMRM (1997) 1937.

Ocali, O. et al., "Intravascular magnetic resonance imaging using a loopless catheter antenna," Magn. Reson. Med. (1997) 37(1):112-118.

Patz, S. et al., "A novel approach to MRI visibility of catheters in real-time studies," BSX poster #2255, International Society for Magnetic Resonance in Medicine, 10th Scientific Meeting and Exhibition (May 18-24, 2002).

Unal, O. et al., "A rapid 2D time-resolved variable-rate κ-space sampling MR technique for passive catheter tracking during endovascular procedures," Magn. Reson. Med. (1998) 40(3):356-362.

Unal, O. et al., Multi-mode Probes for MR-guided Therapeutic Endovascular Interventions, p. 1398, Proc. Intl. Soc. Mag. Reson. Med. 14, 2006.

Leung, D.A. et al., "Intravascular MR Tracking Catheter: Preliminary Experimental Evaluation," Amer. J. Roentgenology (1995) 164:1265-1270.

Omary, R.A. et al., "Real-time MR imaging-guided passive catheter tracking with use of gadolinium-filled catheters," J. Vascular & Interventional Radiology (2000) 11(8):1079-1085.

Buecker, A. et al., "Simultaneous real-time visualization of the catheter tip and vascular anatomy for MR-guided PTA of iliac arteries in an animal model," J. Mag. Res. Imag. (2002) 16:201-208.

Brodsky, E.K. et al., "Using multiple half-echos to improve sampling efficiency and fat suppression in time-resolved MRA," Proc. Int. Soc. Mag. Reson. Med. (2003) 11:322.

Quick, H.H. et al., "Interventional magnetic resonance angiography with no strings attached: wireless active catheter visualization," Mag. Res. Med. (2005) 53:446-455.

Scott, G.C. et al., "Resistively coupled interventional device visualization," Proc. Intl. Soc. Mag. Reson. Med. (2006) 14:266.

Zuehlsdorff, S. et al., "MR coil design for simultaneous tip tracking and curvature delineation of a catheter," Mag. Res. Med. (2004) 52:214-218.

* cited by examiner

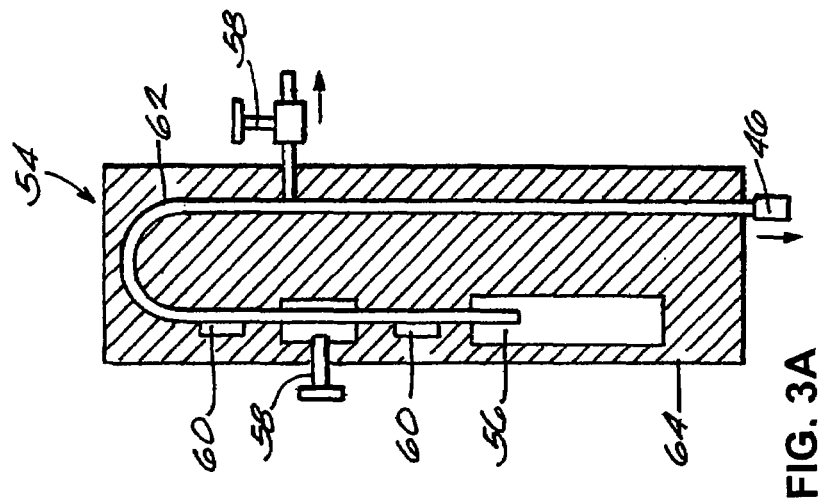
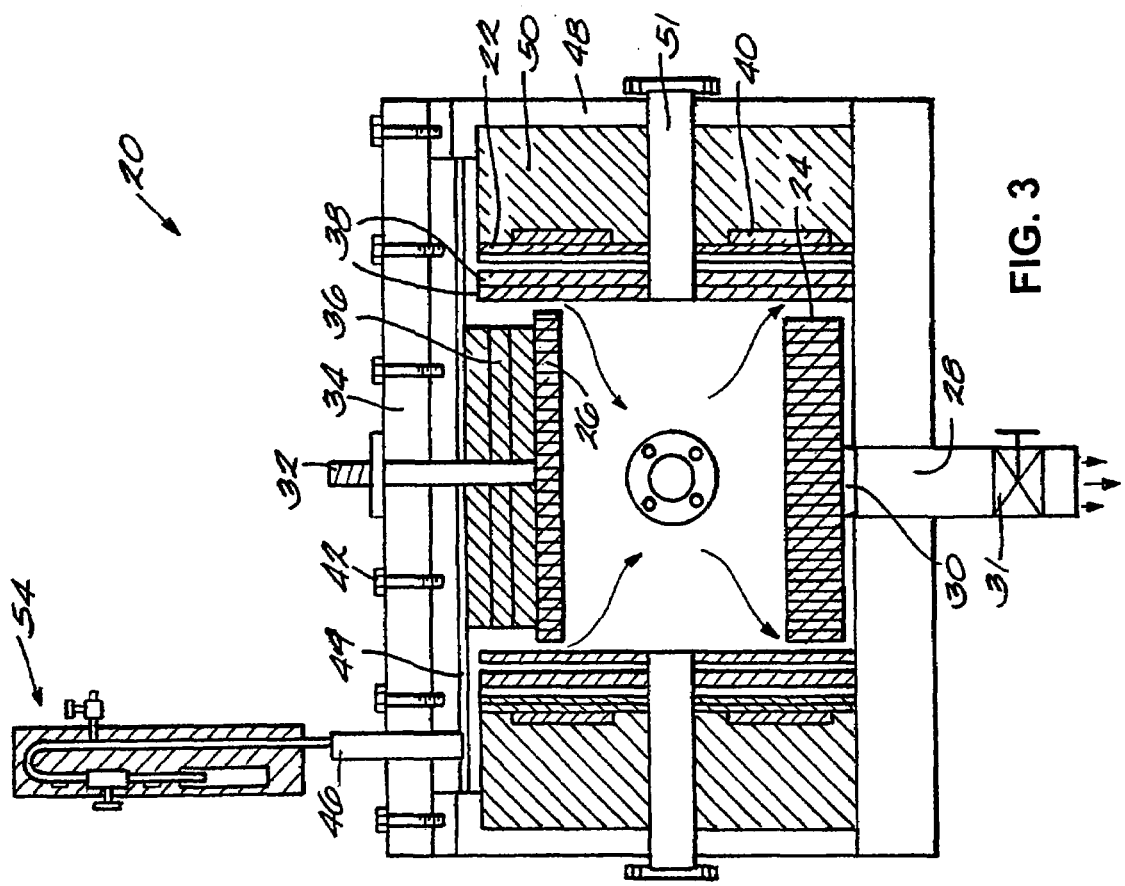
FIG. 3A
FIG. 3

(a) (b)
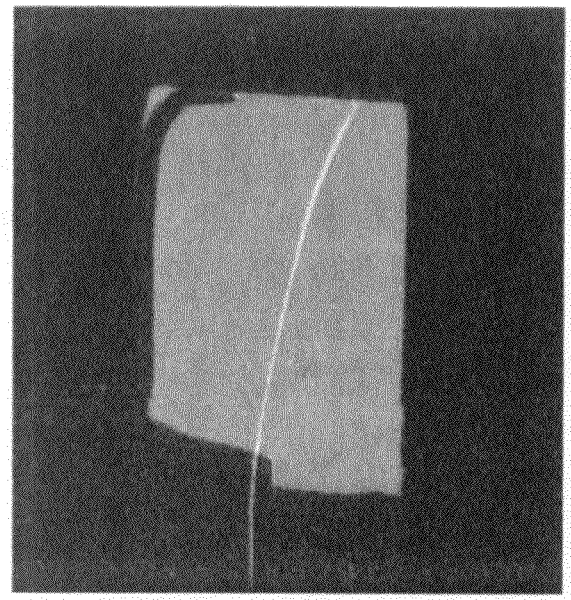 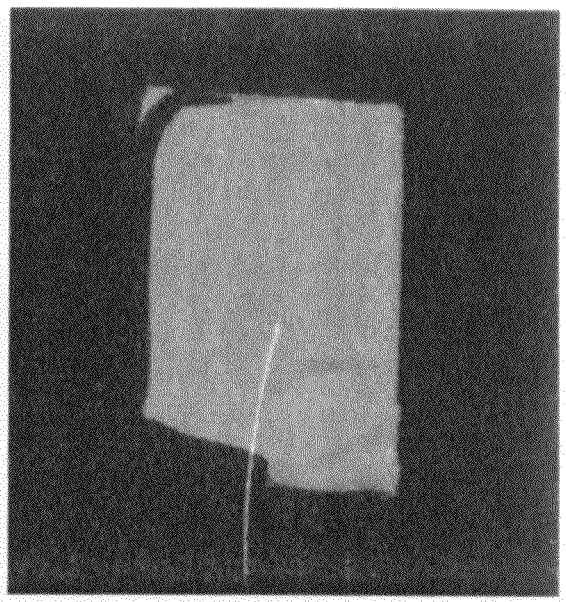
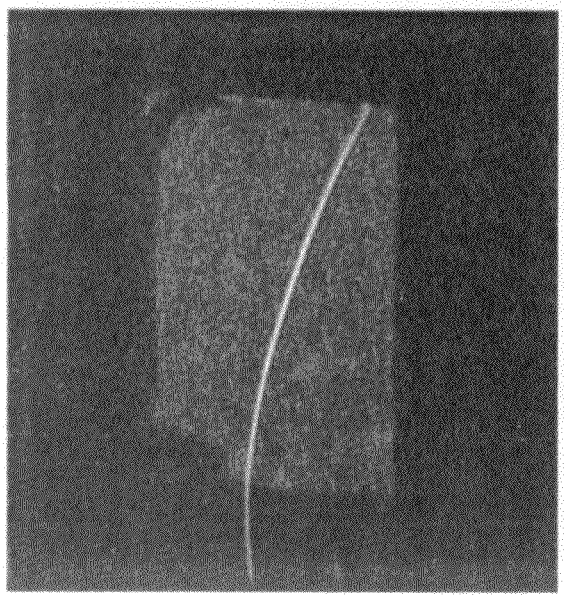 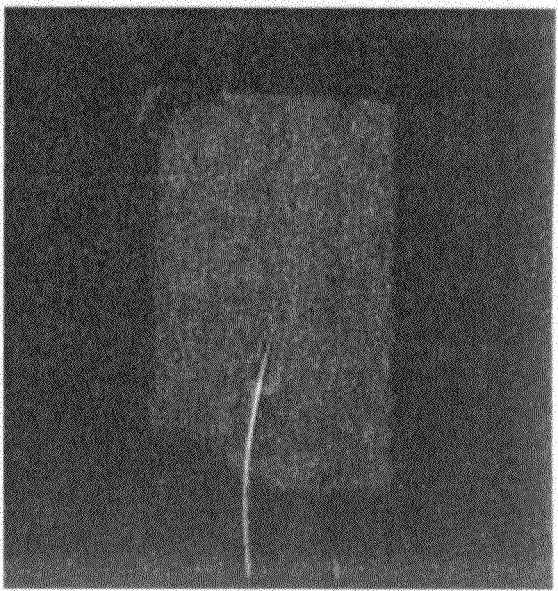
(c) (d)
FIG. 5

Samples for MRI tests
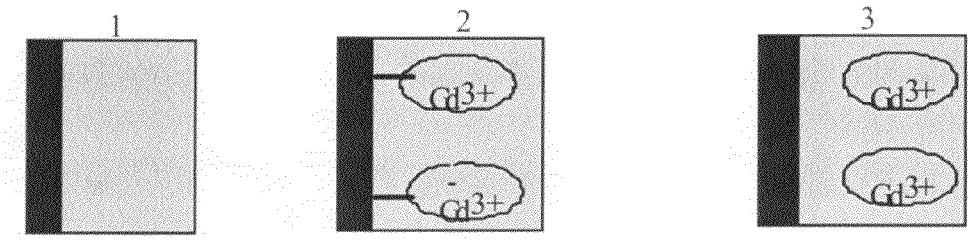
PE/ agarose     PE-DTPA[Gd(III)]/ agarose     PE/ (DTPA[Gd(III)]+agarose)
Sapmles 1, 2, and 3 are soaked in yogurt, saline and human blood respectively in MRI test
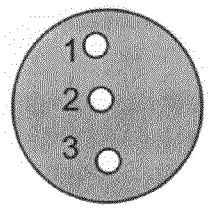 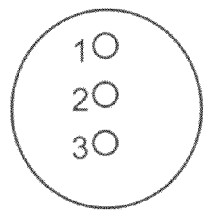 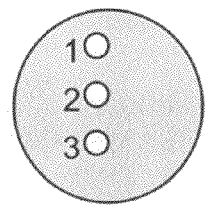
In yogurt     In saline (0.9% NaCL, pH=5.0 Osmolarity=308mOsmol/L)     In human blood
Figure 9

- DTPA linker to primary polymer chain (1)
- physisorption site of hydrogel chain on PEsurface (2)
- covalent links of polymer chains on PEsurface (3)
- cross-linker of hydrogel chains (4)
- cross-linker of primary polymer and hydrogel chains (4)
- DTPA-$Gd^{3+}$ complex (5)
- primary polymer chain linked to PE surface (6)
- gel polymer chain (7)

(1) -NH-CO-, amide linkage
(3) SurModics proprietary process, most likely photo-initiated.
(4) a. If hydrogel chain is poly(acrylamide), bisacrylamide is crosslinker

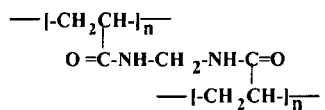

N, N'-methylene-bisacrylamide crosslinker b. If hydrogel chain is gelatin, glutaraldehyde is crosslinker,
-N=CH-CH2-CH2-CH2-CH=N-

(5) DTPA-Gd(III) complex

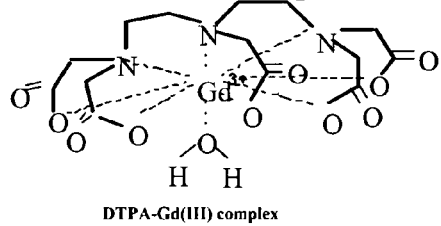

DTPA-Gd(III) complex (6) SurModics proprietary material (7) a. poly(acrylamide), 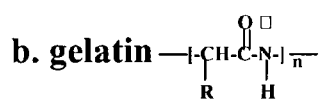

b. gelatin

Figure 14

(1) -NH-CO-, amide linkage
(2) Hydrophobic patches of PE surfaces
(3) Hydrogel chain is gelatin, so glutaraldehyde is the crosslinker for both gelatin-gelatin and gelatin-primary polymer(amine containing),
-N=CH-CH2-CH2-CH2-CH=N-
(4) DTPA-Gd(III) complex    (5) poly(N-[3-aminopropyl]-methacrylamide)
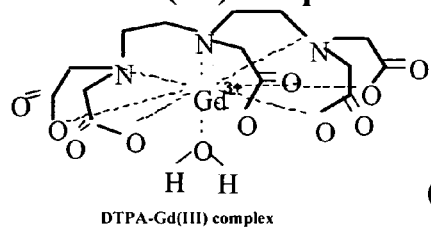
DTPA-Gd(III) complex
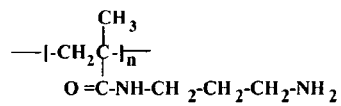
(6) gelatin
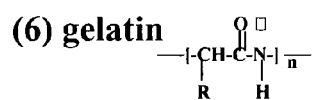
Figure 17

● DTPA linker to hydrogel chain (1)

▫ physisorption site of hydrogel chain on PE surface (2)

● cross-linker of hydrogel chains (3)

(Gd³⁺) DTPA-Gd³⁺ complex (4)

∿ hydrogel polymer chain (5)

(1) -NH-CO-, amide linkage
(2) Hydrophobic patches on PE surfaces
(3) Hydrogel chain is gelatin, so glutaraldehyde is the crosslinker
-N=CH-CH2-CH2-CH2-CH=N-
(4) DTPA-Gd(III) complex      (5) gelatin
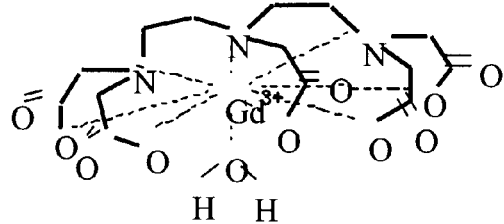
DTPA-Gd(III) complex
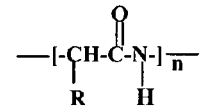
Figure 20

VOLTAGE STANDING WAVE SUPPRESSION FOR MR-GUIDED THERAPEUTIC INTERVENTIONS

RELATED APPLICATIONS

This application claims the benefit of provisional U.S. patent application Ser. No. 60/904,158 titled "Multi-Mode Probe for MR-Guided Therapeutic Endovascular Interventions" filed on Feb. 28, 2007, the entire disclosure of which is incorporated by reference. Also incorporated herein by reference is the content of U.S. patent application Ser. No. 11/728,873 titled "System and Method of Performing Therapeutic Endovascular Interventions" filed on an even date herewith.

STATEMENT REGARDING FEDERALLY SPONSORED RESEARCH OR DEVELOPMENT

This invention was made with United States Government support under Grant No. NIH HL072260 awarded by the National Institutes of Health. The United States Government has certain rights in this invention.

BACKGROUND

Since its introduction, magnetic resonance (MR) has been used to a large extent solely for diagnostic applications. Recent advancements in magnetic resonance imaging now make it possible to replace many diagnostic examinations previously performed with x-ray imaging with MR techniques. For example, the accepted standard for diagnostic assessment of patients with vascular disease was, until quite recently, x-ray angiography. Today, MR angiographic techniques are increasingly being used for diagnostic evaluation of these patients. In some specific instances such as evaluation of patients suspected of having atheroscleroic disease of the carotid arteries, the quality of MR angiograms, particularly if they are done in conjunction with contrast-enhancement, reaches the diagnostic standards previously set by x-ray angiography.

More recently, advances in MR hardware and imaging sequences have begun to permit the use of MR for monitoring and control of certain therapeutic procedures. That is, certain therapeutic procedures or therapies are performed using MR imaging for monitoring and control. In such instances, the instruments, devices or agents used for the procedure and/or implanted during the procedure are visualized using MR rather than with x-ray fluoroscopy or angiography. The use of MR in this manner of image-guided therapy is often referred to as interventional magnetic resonance (interventional MR). These early applications have included monitoring ultrasound and laser ablations of tumors, guiding the placement of biopsy needles, and monitoring the operative removal of tumors.

Of particular interest is the potential of using interventional MR for the monitoring and control of endovascular therapy. Endovascular therapy refers to a general class of minimally-invasive interventional (or surgical) techniques which are used to treat a variety of diseases such as vascular disease and tumors. Unlike conventional open surgical techniques, endovascular therapies utilize the vascular system to access and treat the disease. For such a procedure, the vascular system is accessed by way of a peripheral artery or vein such as the common femoral vein or artery. Typically, a small incision is made in the groin and either the common femoral artery or vein is punctured. An access sheath is then inserted and through the sheath a catheter is introduced and advanced over a guide-wire to the area of interest. These maneuvers are monitored and controlled using x-ray fluoroscopy and angiography. Once the catheter is properly situated, the guide-wire is removed from the catheter lumen, and either a therapeutic device (e.g., balloon, stent, coil) is inserted with the appropriate delivery device, or an agent (e.g., embolic agent, anti-vasospasm agent) is injected through the catheter. In either instance, the catheter functions as a conduit and ensures the accurate and localized delivery of the therapeutic device or agent to the region of interest. After the treatment is completed, its delivery system is withdrawn, i.e., the catheter is withdrawn, the sheath removed and the incision closed. The duration of an average endovascular procedure is about 3 hours, although difficult cases may take more than 8 hours. Traditionally, such procedures have been performed under x-ray fluoroscopic guidance.

Performing these procedures under MR-guidance provides a number of advantages. Safety issues are associated with the relatively large dosages of ionizing radiation required for x-ray fluoroscopy and angiographic guidance, whereas MR is free of harmful ionizing radiation. While radiation risk to the patient is of somewhat less concern (since it is more than offset by the potential benefit of the procedure), exposure to the interventional staff can be a major problem. In addition, the adverse reactions associated with MR contrast agents is considerably less than that associated with the iodinated contrast agents used for x-ray guided procedures.

Other advantages of MR-guided procedures include the ability to acquire three-dimensional images. In contrast, most x-ray angiography systems can only acquire a series of two-dimensional projection images. MR has clear advantages when multiple projections or volume reformatting are required in order to understand the treatment of complex three-dimensional vascular abnormalities, such as arterial-venous malformations (AVMs) and aneurysms. Furthermore, MR is an attractive modality for image-guided therapeutic interventions for its ability to provide excellent soft-tissue contrast and multi-planar capability. MR is sensitive to measurement of a variety of functional parameters, and thus, MR has the capability to provide not only anatomical information but also functional or physiological information including temperature, blood flow, tissue perfusion and diffusion, brain activation, and glomerular filtration rate (GFR). This additional diagnostic information, which, in principle, can be obtained before, during and immediately after therapy, cannot be acquired by x-ray fluoroscopy alone. Therefore, MR has the potential to change intravascular therapy profoundly if it can be used for performing MR-guided therapeutic endovascular procedures.

SUMMARY

An MR-guided minimally-invasive endovascular procedure requires (1) tracking and guidance of therapeutic endovascular devices such as catheters and guidewires to the region of interest, (2) obtaining high-resolution anatomical images of the target region and its surroundings in real-time in order to diagnose and assess disease, (3) performing a therapeutic procedure or intervention, and (4) evaluation of the outcome of the therapeutic procedure.

In one embodiment, the invention provides a medical device system comprising a medical device having an exterior surface, a distal end and a proximal end, a tracking device coupled to the exterior surface adjacent the distal end of the medical device, a conductive member electrically coupled to the tracking device and extending to the proximal end of the medical device and a proximal cable trap and a distal cable trap electrically coupled to the conductive member. The tracking device is adapted to transmit a signal to an imaging system to generate an image field forward of the distal end.

In another embodiment, the invention provides a medical device system comprising a medical device having an exterior surface, a distal end and a proximal end, a tracking device coupled to the exterior surface adjacent the distal end of the medical device, a conductive member electrically coupled to the tracking device and extending to the proximal end of the medical device and a voltage standing wave suppression device on the exterior surface of the medical device. The tracking device is adapted to transmit a signal to an imaging system to generate an imaging field-of-view forward of the distal end.

In another embodiment, the invention provides a medical device system comprising a medical device having an exterior surface, a distal end and a proximal end, an imaging device extending from a proximal end of the medical device to the distal end and configured to internally image from a point of view of the medical device and a proximal cable trap and a distal cable trap electrically coupled to the imaging device.

In another embodiment, the invention provides a method of performing an interventional procedure using an imaging system. The method comprises moving a multi-mode medical device toward a target area, transmitting a differential mode signal from a distal end of the medical device to a proximal end of the medical device and suppressing a common mode signal on an exterior of the medical device.

In another embodiment, the invention provides a medical device system comprising a medical device having an exterior surface, a distal end and a proximal end, a tracking device, an imaging device, an MR-visible coating and a proximal cable trap and a distal cable trap electrically coupled to the imaging device. The tracking device is coupled to the exterior surface adjacent the distal end of the medical device and is adapted to transmit a signal to an imaging system to generate an imaging field-of-view forward of the distal end. The imaging device is electrically coupled to the tracking device and is adapted to transmit a signal to the imaging system to generate an image from a point of view of the medical device. The MR-visible coating is applied to at least a portion of the medical device to allow the respective portion of the medical device to be visualized using magnetic resonance imaging. The MR-visible coating includes at least one of a paramagnetic-metal-ion/ligand complex, a paramagnetic-metal-ion/chelate complex, a cross-linker, a hydrogel, and combinations thereof.

In another embodiment, the invention provides a medical device system comprising a medical device having an exterior surface, a distal end and a proximal end, the medical device being adapted for use within an external field, a co-axial conductive member extending from the distal end of the medical device to the proximal end of the medical device, and a proximal cable trap and a distal cable trap coupled to the exterior surface of the medical device.

In another embodiment, the invention provides a medical device system comprising a medical device having an exterior surface, a distal end and a proximal end, the co-axial device being adapted for use within an external field, a co-axial conductive member extending from the distal end of the medical device to the proximal end of the medical device, and a voltage standing wave suppression device coupled to the exterior surface of the medical device.

Other aspects of the invention will become apparent by consideration of the detailed description and accompanying drawings.

BRIEF DESCRIPTION OF THE DRAWINGS

FIGS. 3 and 3A are schematic representations of a capacitively coupled RF plasma reactor for use in the method of the present invention, FIG. 3A being an enlarged view of the vapor supply assemblage of the plasma reactor of FIG. 3;

FIG. 5 is temporal MR snapshots of a Gd-DTPA-filled catheter;

FIG. 8 shows the chemical synthesis of linking DTPA[Gd(III)] to the surface of a polymer-based medical device and the overcoating of the device with a hydrogel.

FIG. 9 is a diagram showing hydrogel overcoating of three samples to undergo MR-visibility testing.

FIG. 13 shows the chemical structure of an MR signal-emitting coating polymer-based medical device in which DTPA[Gd(III)] was attached on the device surface, and then encapsulated by a cross-linked hydrogel.

FIG. 14 shows the chemical details for the example schematically represented in FIG. 13.

FIG. 15 is an MR maximum-intensity-projection (MIP) image, using a 3D RF spoiled gradient-recalled echo (SPGR) sequence in a live canine aorta, of an example of the second embodiment of the present invention shown in FIG. 13 with dry thickness of the entire coating of 60 μm. The length of coated PE rod is about 40 cm with a diameter of about 2 mm. The image was acquired 25 minutes after the rod was inserted into the canine aorta.

FIG. 16 shows the chemical structure of an MR signal-emitting hydrogel coating on the surface of a medical device in which a DTPA[Gd(III)] linked primary polymer was dispersed and cross-linked with hydrogel.

FIG. 17 shows the chemical details for the example schematically represented in FIG. 16.

FIG. 18 is an MR maximum-intensity-projection (MIP) image, using a 3D RF spoiled gradient-recalled echo (SPGR) sequence in a live canine aorta, of an example of the third embodiment of the present invention shown in FIG. 16 with dry thickness of the entire coating of about 60 μm, but with a guide-wire instead of polyethylene. The length of coated guide-wire is about 60 cm with the diameter of about 0.038 in. The image was acquired 10 minutes after the guide-wire was inserted into the canine aorta.

FIG. 19 is a schematic representation of a hydrogel (e.g. gelatin) encapsulating the complex. In other words, FIG. 19 shows the chemical structure of an MR signal-emitting hydrogel coating on the surface of a medical device in which a DTPA[Gd(III)] linked hydrogel, gelatin, was dispersed and cross-linked.

FIG. 20 shows the chemical details for the example schematically represented in FIG. 19.

FIG. 21 shows an MR maximum-intensity-projection (MIP) image, using a 3D RF spoiled gradient-recalled echo (SPGR) sequence in a live canine aorta, of the example of the fourth embodiment of the present invention shown in FIG. 19 with dry thickness of the entire coating of 60 μm, but with a guide-wire instead of polyethylene. The length of coated guide-wire is about 60 cm with the diameter of about 0.038 in. The image was acquired 30 minutes after the rod was inserted into the canine aorta.

FIG. 22 shows an MR maximum-intensity-projection (MIP) image, using a 3D RF spoiled gradient-recalled echo (SPGR) sequence in a live canine aorta, of the example of the fourth embodiment of the present invention shown in FIG. 19 with dry thickness of the entire coating of 30 μm, but with a guide-wire instead of polyethylene. The length of coated guide-wire is about 45 cm with a diameter of about 4 F. The image was acquired 20 minutes after the rod was inserted into the canine aorta.

FIG. 23 shows the chemical structure of an MR signal-emitting hydrogel coating on the surface of a medical device in which a hydrogel, namely, gelatin sequesters a DTPA[Gd(III)] complex, upon cross-linking the gelatin with glutaraldehyde. The complex is not covalently linked to the hydrogel or the substrate.

DETAILED DESCRIPTION

Figure 1:
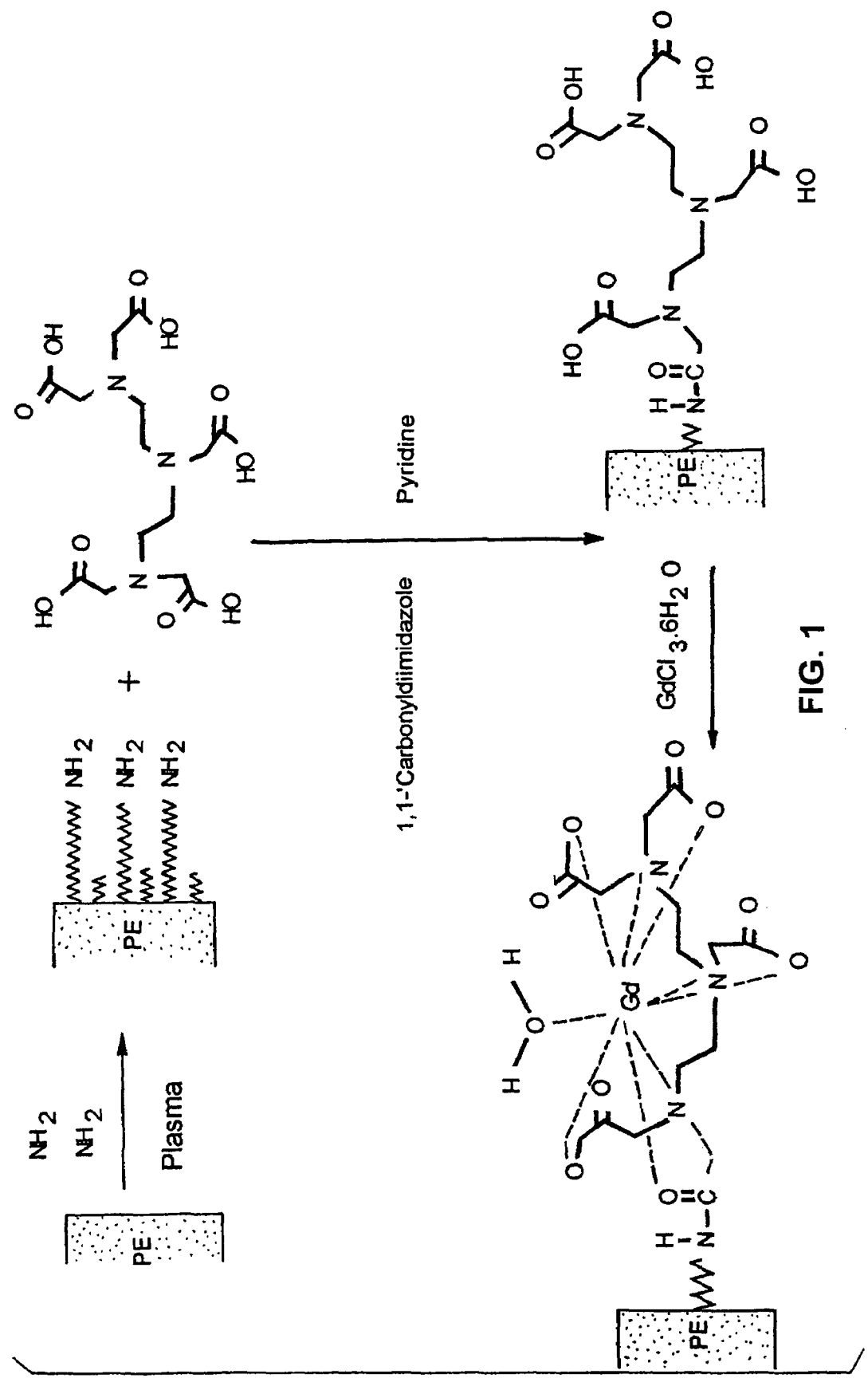
FIG. 1 is a schematic representation of the three-step coating method in accordance with the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any nonclaimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Some embodiments of the present invention relate to multi-mode medical device systems capable of being tracked and visualized under magnetic resonance (MR) guidance, of internal imaging anatomical structures, and/or of practicing interventional therapeutic procedures. Methods of the present invention can include methods of manufacturing a multi-mode medical device system, methods of tracking and visualizing a multi-mode medical device system using MR guidance, methods of MR imaging with the multi-mode medical device system, methods of enhancing the practice of interventional therapeutic procedures, and methods of using one multi-mode medical device system to perform tracking, visualizing, internal imaging and interventional procedures.

As used herein and in the appended claims, the term "medical device" is used in a broad sense to refer to any tool, instrument or object that can be employed to perform an operation or therapy on a target, or which itself can be implanted in the body (human or animal) for some therapeutic purpose. Examples of medical devices that can be employed to perform an operation or therapy on a target include, but are not limited to, at least one of endovascular devices, biopsy needles, ablation devices, and any other device suitable for being used to perform an operation or therapy on a target. Examples of medical devices which can be implanted in the body include, but are not limited to, at least one of a stent, a graft, and any other device suitable for being implanted in the body for a therapeutic purpose.

Examples of endovascular devices include, without limitation, at least one of catheters, guidewires, ablation devices, and combinations thereof. Examples of endovascular procedures that can be performed with the multi-mode medical device system of the present invention include, without limitation, at least one of the treatment of partial vascular occlusions with balloons; the treatment of arterial-venous malformations with embolic agents; the treatment of aneurysms with stents or coils; the treatment of sub-arachnoid hemorrhage (SAH)-induced vasospasm with local applications of papaverine; the delivery and tracking of drugs and/or stem cells; the treatment of tumors with electromagnetic energy; and combinations thereof. In these endovascular procedures, the device or agent can be delivered via the lumen of a catheter, the placement of which has traditionally relied on, to varying degrees, x-ray fluoroscopic guidance.

As used herein and in the appended claims, the term "target" or "target object" is used to refer to all or part of an object, human or animal to be visualized and/or internally imaged. When visualized, the target or target object can be positioned in an imaging region of a magnetic resonance imaging system ("MRI system"). As used herein and in the appended claims, the term "imaging region" is used to refer to the space within an MRI system in which a target can be positioned to be visualized using an MRI system. As used herein and in the appended claims, the term "target region" or "target area" is used to refer to a region of the target or target object of interest. For example, in an endovascular procedure, the target may be a human body, and the target region may be a specific blood vessel, or a portion thereof, within the human body.

An MR-guided interventional procedure can include: a) MR-guidance of a medical device to the region of interest, b) high-resolution MR imaging of the target region and its surroundings in order to diagnose and assess disease, c) performance of a therapeutic interventional procedure, and d) evaluation of the outcome/efficacy of the therapeutic procedure. A number of methods have been previously developed and employed for the separate tracking and visualization of medical devices. Independent devices have also been developed for high spatial resolution internal imaging, as the requirements for tracking and imaging devices are entirely different. A procedure that employs separate tracking and imaging devices, however, will necessitate multiple insertions and extractions of the medical device from the target region, thereby increasing the risk of causing injury to surrounding tissue (e.g., vasculature).

As used herein and in the appended claims, the term "pass" is used to refer to the entire cycle of inserting and removing a medical device from a target object, such as a human body. In other words, a pass refers to one cycle of insertion and extraction. Endovascular procedures generally require several passes with multiple devices to perform a therapeutic procedure. For example, tracking, internal imaging, and visualization, and ultimately the therapeutic procedure are performed by separate medical devices, each requiring separate insertions and extractions. In contrast, the present invention is directed to a multi-mode medical device system that can be tracked, visualized, used to internally image internal structures and/or perform therapeutic procedures, in a single pass. Using multiple devices and multiple passes increase the complexity of the procedures, and ultimately, the associated health risk.

The present invention generally relates to multi-mode medical device systems that combine the functionalities of tracking, visualizing, internal imaging, and performing a therapeutic procedure. Although some embodiments of the present invention can be applied to endovascular devices and procedures, one of ordinary skill in the art will appreciate that any description herein relevant to endovascular devices is meant to be exemplary only and should not be viewed as restrictive of the full scope of the present invention.

A multi-mode medical device system of the present invention can include a medical device, a tracking device and an imaging device. The multi-mode medical device system can be tracked and used for internal imaging, all under MR guidance, without requiring multiple insertions and extractions of various medical devices. The multi-mode medical device system of the present invention can achieve a high spatial resolution MR image. High spatial resolution can be quantified as a spatial resolution of about 200 µm or less, particularly, less than about 100 µm, and more particularly, less than about 50 µm. In some embodiments, the multi-mode medical device system further includes a visualizing device, such that the multi-mode medical device system can also be visualized under MR guidance without requiring multiple insertions and extractions of medical devices. As a result, in some embodiments, the multi-mode medical device system can be tracked, visualized, and used to produce MR images from the point of view of the medical device, in a single pass of the medical device system.

In one aspect, the present invention may provide an MRI system (also referred to herein as an "MR scanner") for generating an MR image of a target object in an imaging region and, in some embodiments, a multi-mode medical device system for use with the target object in the imaging region.

Figure 31:
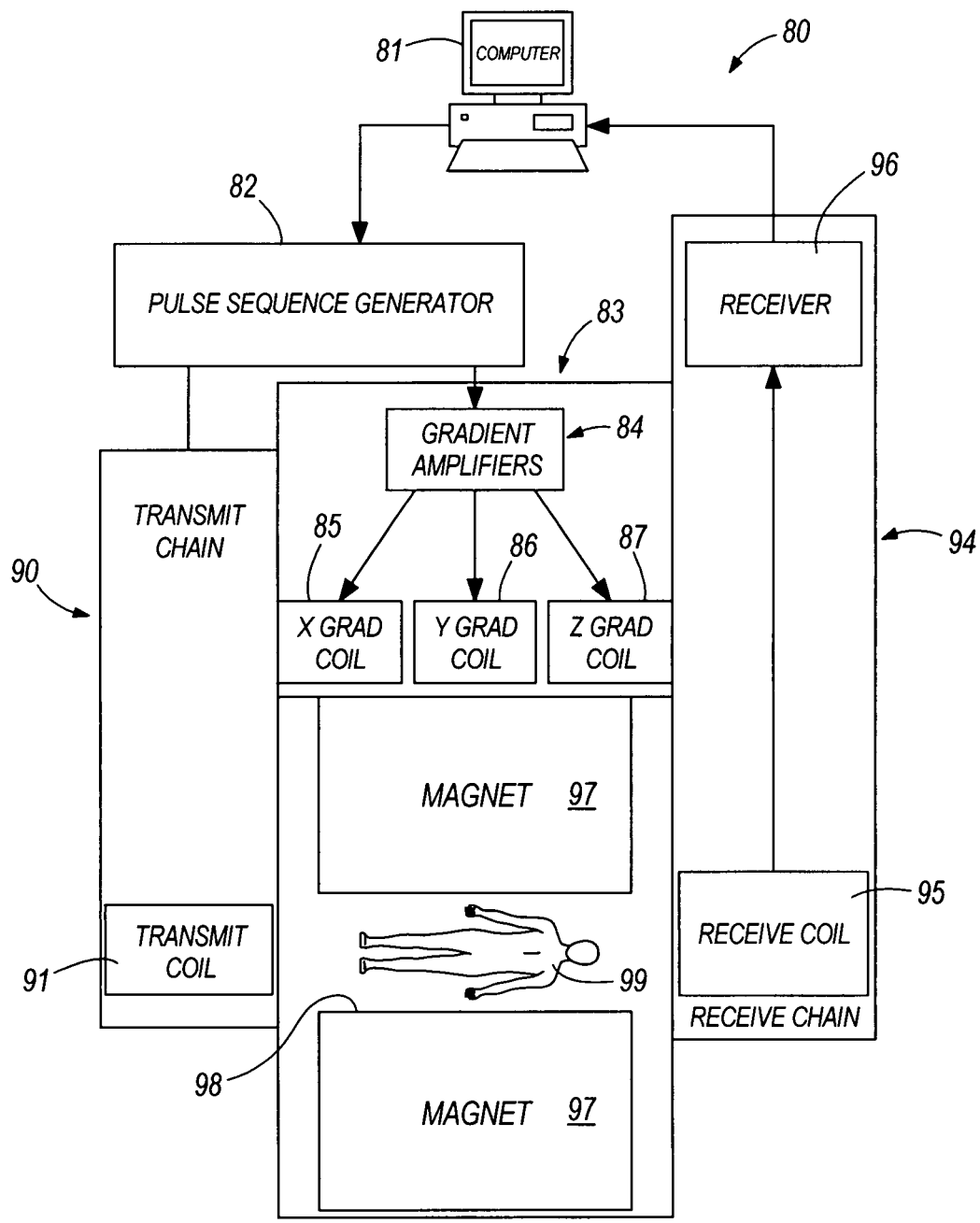
FIG. 31 is a schematic block diagram of a magnetic resonance imaging system and according to one embodiment of the present invention.

FIG. 31 illustrates one embodiment of an MRI system 80 according to the present invention. The MRI system 80 includes a computer 81; a pulse sequence generator 82; a gradient chain 83 having gradient amplifiers 84, an X gradient coil 85, a Y gradient coil 86 and a Z gradient coil 87; a transmit chain 90 including an RF transmit coil 91; a receive chain 94 including an RF receive coil 95 and a receiver 96; and one or more magnets 97 that define a main magnetic field and a bore or imaging region 98 within which a target object 99 can be positioned.

The magnet 97 can produce an intense homogeneous magnetic field around a target object 99 or portion of a target object 99. The magnet 97 can include a variety of types of magnets including one or more of the following magnet types: 1) permanent, 2) resistive, and 3) superconducting. Permanent magnets can be used for very low field MRI systems (0.02 to 0.4 T). Resistive magnets can also be used for low field systems (0.3 to 0.6 T). Many clinical MRI systems (0.7 to 3 T) are of the superconducting type. A superconducting magnet can include a wire that is wound into a solenoid, energized, and short circuited on itself. The superconducting magnet can be kept at temperatures near absolute zero (~4.2K) by immersing it in liquid helium. This can create a very homogeneous high magnetic field.

The computer 81 is the central processing/imaging system for the MRI system 80. The computer 81 can receive demodulated signals from the receive chain 94, and can process the signals into interpretable data, such as a visual image. The entire process of obtaining an MR image can be coordinated by the computer 81, which can include generating perfectly timed gradient and RF pulses and then post-processing the received signals to reveal the anatomical images.

The pulse sequence generator 82 generates timed gradient and RF pulse profiles based on communications from the computer 81. The pulse sequence generator 82 can route a gradient waveform to an appropriate gradient amplifier 85, 86 and/or 87 in the gradient chain 83, and an RF waveform to the transmit chain 90, as defined by the pulse sequence.

The gradient chain 83, also sometimes referred to as a "magnetic gradient system" or "magnetic gradient coil assembly," can localize a portion of the target object 99. The gradient chain 83 includes three gradient amplifiers 84 (X, Y and Z), and corresponding gradient coils 85, 86 and 87 that are placed inside the bore 98 of the magnet 97. The gradient coils 85, 86 and 87 can be used to produce a linear variation in the main magnetic field along one direction. The gradient amplifiers 84 can be housed in racks remote from the remainder of the MRI system 80.

Thus, the magnet 97 which produces a homogenous magnetic field is used in conjunction with the gradient chain 83. The gradient chain 83 can be sequentially pulsed to create a sequence of controlled gradients in the main magnetic field during an MRI data gathering sequence.

The transmit chain 90 can include frequency synthesizers, mixers, quadrature modulators, and a power amplifier that work together to produce an RF current pulse of appropriate frequency, shape and power, as specified by the computer 81. The RF transmit coil 91 can convert the RF current pulse into a transverse RF magnetic field, which in turn, generates magnetic moment spin flips responsible for MR signal generation.

The RF receive coil 95 senses the RF magnetic field emitted by the magnetic moment spins, and converts it into a voltage signal. The receiver 96 can include demodulators, filters, and analog to digital converters (ADC). The signal from the RF receive coil 95 can be demodulated down to base band, filtered and sampled. An anatomical image can be reconstructed from the samples using the computer 81. The RF transmit coil 91 and the RF receive coil 95 are sometimes referred to herein as an external RF coil or a whole body (RF) coil. In some embodiments, the MRI system 80 includes one external RF coil capable of functioning as the RF transmit coil 91 and the RF receive coil 95.

The magnet 97 and the gradient chain 83 can include the RF transmit coil 91 and the RF receive coil 95 on an inner circumferential side of the gradient chain 83. The controlled sequential gradients are effectuated throughout the bore or imaging region 98, which is coupled to at least one MRI (RF) coil or antenna. The RF coils and an RF shield can be located between the gradient chain 83 and the bore 98.

RF signals of suitable frequencies can be transmitted into the bore 98. Nuclear magnetic resonance (NMR) responsive RF signals are received from the target object 99 via the RF receive coil 95. Information encoded within the frequency and phase parameters of the received RF signals, can be processed to form visual images. These visual images represent the distribution of NMR nuclei within a cross-section or volume of the target object 99 within the bore 98.

As used herein and in the appended claims, the term "internal imaging" refers to viewing a target object, portions thereof or other objects within the target object from the point of a medical device positioned within the target object. For example, internal imaging can include viewing anatomical structures, medical devices and/or other items inside a target object from the point of view of a medical device. Internal imaging can be accomplished by coupling an imaging device to the medical device.

Internal imaging anatomical structures and/or pathologies using MRI can provide high-resolution imaging of a target region and its surroundings in order to diagnose and assess disease. In addition, internal imaging allows for identification of the location in which a therapeutic procedure or intervention may need to occur. Finally, internal imaging allows for evaluation of the outcome or efficacy of the therapeutic procedure.

Figure 32:
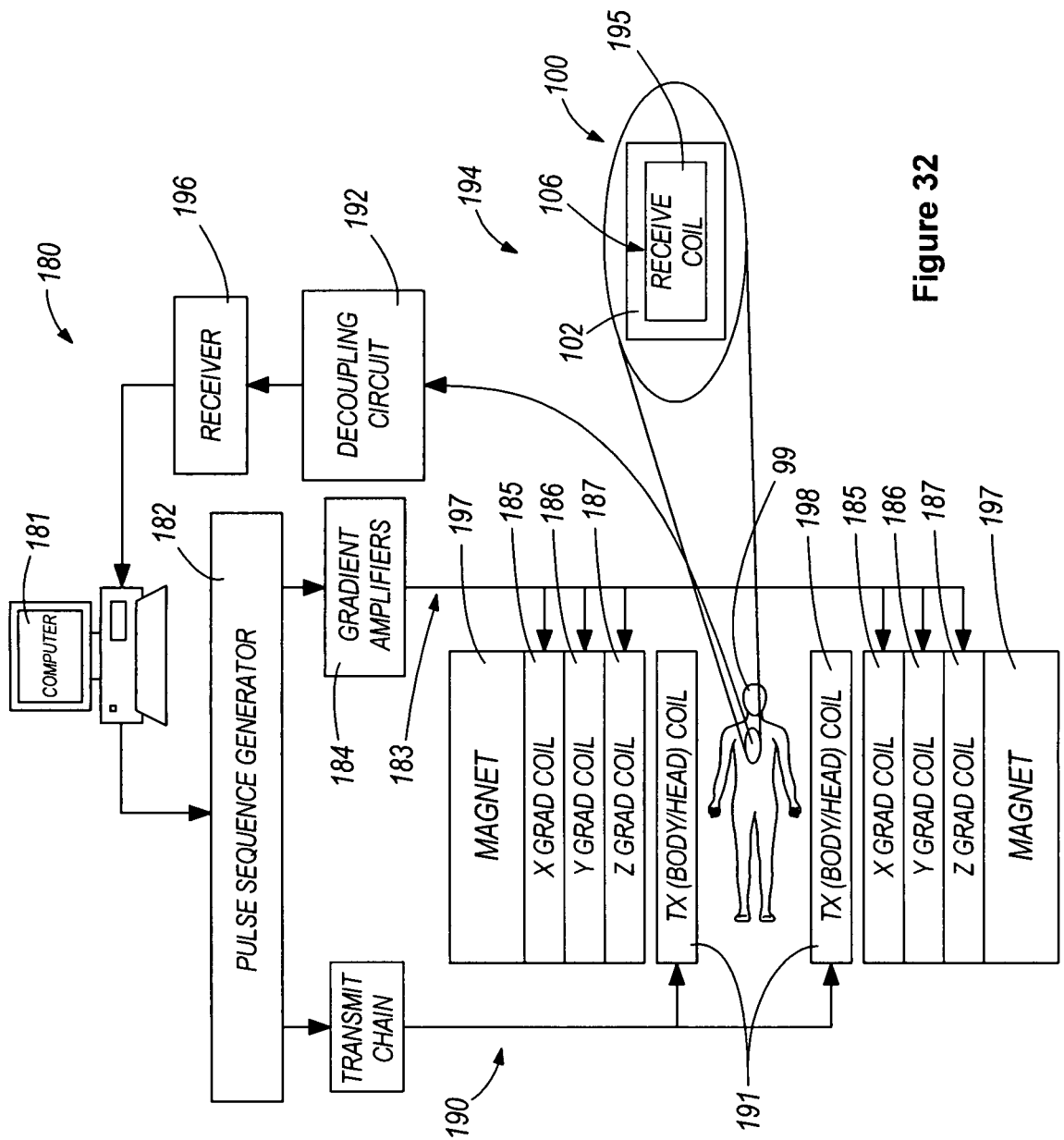
FIG. 32 is a schematic block diagram of a magnetic resonance imaging system and a multi-mode medical device system according to another embodiment of the present invention.

FIG. 32 illustrates another embodiment of an MRI system 180 according to the present invention, wherein like numerals represent like elements. The MRI system 180 shares many of the same elements and features described above with reference to the illustrated embodiment of FIG. 31. Accordingly, elements and features corresponding to elements and features in the illustrated embodiment of FIG. 31 are provided with the same reference numerals in the 100 series. Reference is made to the description above accompanying FIG. 31 for a more complete description of the features and elements (and alternatives to such features and elements) of the embodiment illustrated in FIG. 32.

As shown in FIG. 32, the MRI system 180 includes a computer 181; a pulse sequence generator 182; a gradient chain 183 having gradient amplifiers 184, an X gradient coil 185, a Y gradient coil 186 and a Z gradient coil 187; a transmit chain 190 including an RF transmit coil 191; a receive chain 194 including an RF receive coil 195 coupled to a medical device 102 that is positioned within a target object 99, a decoupling circuit 192, and a receiver 196; and one or more magnets 97 that define a main magnetic field and a bore or imaging region 98 within which a target object 99 can be positioned.

A multi-mode medical device system 100 shown in FIG. 32 includes the medical device 102, and an imaging device 106 coupled to the medical device 102. The imaging device 106, or a portion thereof, can function as the RF receive coil 195 for the MRI system 180. A variety of imaging devices 106 that are capable of acting as the RF receive coil 195 for the MRI system 180 can be used with the multi-mode medical device system 100, including, without limitation, a single loop, or particularly, a resonant loop (e.g., as described in Examples 16, 18 and 19 and shown in FIGS. 33-34, 43 and 52, respectively); a saddle coil; multiple loops; multiple solenoids connected either in series or in parallel; three-wire coils; or combinations thereof; or any other imaging device 106 suitable for receiving MR signals that can be manipulated by the computer 181 of the MRI system 180 to generate an MR image.

Unlike the RF receive coil 95 of the MRI system 80 illustrated in FIG. 31, the imaging device 106 of the MRI system 180 is coupled to the medical device 102 and positioned within the target object 99 to internally image the target object 99 from the point of view of the medical device 102. For example, if the medical device 102 includes a catheter positioned within vasculature, the imaging device 106 can sense the RF signal generated by nearby protons, and internally image the vasculature in a variety of orientations (e.g., sagittally, coronally, axially, obliquely, or in any other suitable orientation). The imaging device 106 senses the RF signal generated by the magnetic moment spins, and converts it into a voltage signal that can be sent to the decoupling circuit 192. The imaging device 106 receives similar signals that the external RF receive coil 95 receives, but from the point of view of the medical device 102 (e.g., from the point of view of a catheter being navigated within vasculature). Such internal imaging allows internal anatomical structures and pathologies to be located, observed, evaluated and/or further analyzed or treated.

As shown in FIG. 32, when the multi-mode medical device system 100 is in internal imaging mode, the decoupling circuit 192 receives the signal from the imaging device 106. The decoupling circuit 192 can include a matching network (also sometimes referred to as a "matching portion" of the decoupling circuit 192). The matching network can be used to match the impedance of the imaging device 106, which is typically relatively high, to that of the MRI system 180 (e.g., 50Ω) to achieve maximum transfer of signal from the imaging device 106 to the MRI system 180. The matching network can include a variety of components arranged in a variety of configurations, including, but not limited to, at least one of a pi configuration, a tee configuration, an "L" network, or a combination thereof. In some embodiments, as described in Example 16, the matching portion of the decoupling circuit 192 can be remote from the multi-mode medical device system 100. In some embodiments, as described in Example 18, the matching portion of the decoupling circuit 192 can be positioned at the terminals of the imaging device 106 and coupled to the medical device 102 of the multi-mode medical device system 100.

The decoupling circuit 192 can also include a decoupling network (also sometimes referred to as the "decoupling portion" of the decoupling circuit 192). The decoupling network can be used to decouple the RF signal transmitted by the RF transmit coil 191 during a transmit cycle of the MRI system 180 from that of the imaging device 106. During the transmit cycle, a large RF signal will be induced in the imaging device 106 by the RF transmit coil 191, and the decoupling circuit 192 can prevent this induced RF signal from reaching sensitive downstream circuits in the receive chain 194. A variety of components arranged in a variety of configurations can be used to accomplish this decoupling, including, but not limited to, at least one of an LC circuit, or a combination thereof.

In some embodiments, decoupling is accomplished by activating a switch to connect a capacitor across a series inductor when an appropriate DC bias is applied (e.g., to a PIN diode). The values of the inductor and the capacitor can be chosen to form a parallel resonant tank circuit that essentially acts as a high resistance in series with the signal path from the imaging device 106. The DC bias is generally applied only during the transmit cycle of the MRI system 180 to block the relatively large signal that is induced in the imaging device 106 by the RF transmit coil 191, and protect the sensitive downstream circuits in the receive chain 194. One example of a decoupling network is described in Example 16 and illustrated in FIGS. 38-39 and also in FIGS. 46-48.

In embodiments in which the matching portion is not located remotely from the multi-mode medical device system (e.g., is located at the terminals of the imaging device 106), the decoupling circuit 192 can include a lumped element transmission line section to further optimize the transfer of signal from the imaging device 106 to the MRI system 180. In such embodiments, the lumped element transmission line section can be included to provide the necessary components for the decoupling network while maintaining the appropriate impedance necessary to match the impedance of the MRI system 180. A variety of components arranged in a variety of configurations can be used to form a lumped element transmission line section that provides the appropriate components for the decoupling network, including, but not limited to, at least one of a pi configuration, a tee configuration, or a combination thereof. One example of a lumped element transmission line section is described in Example 18 and illustrated in FIGS. 46-48.

Figure 38:
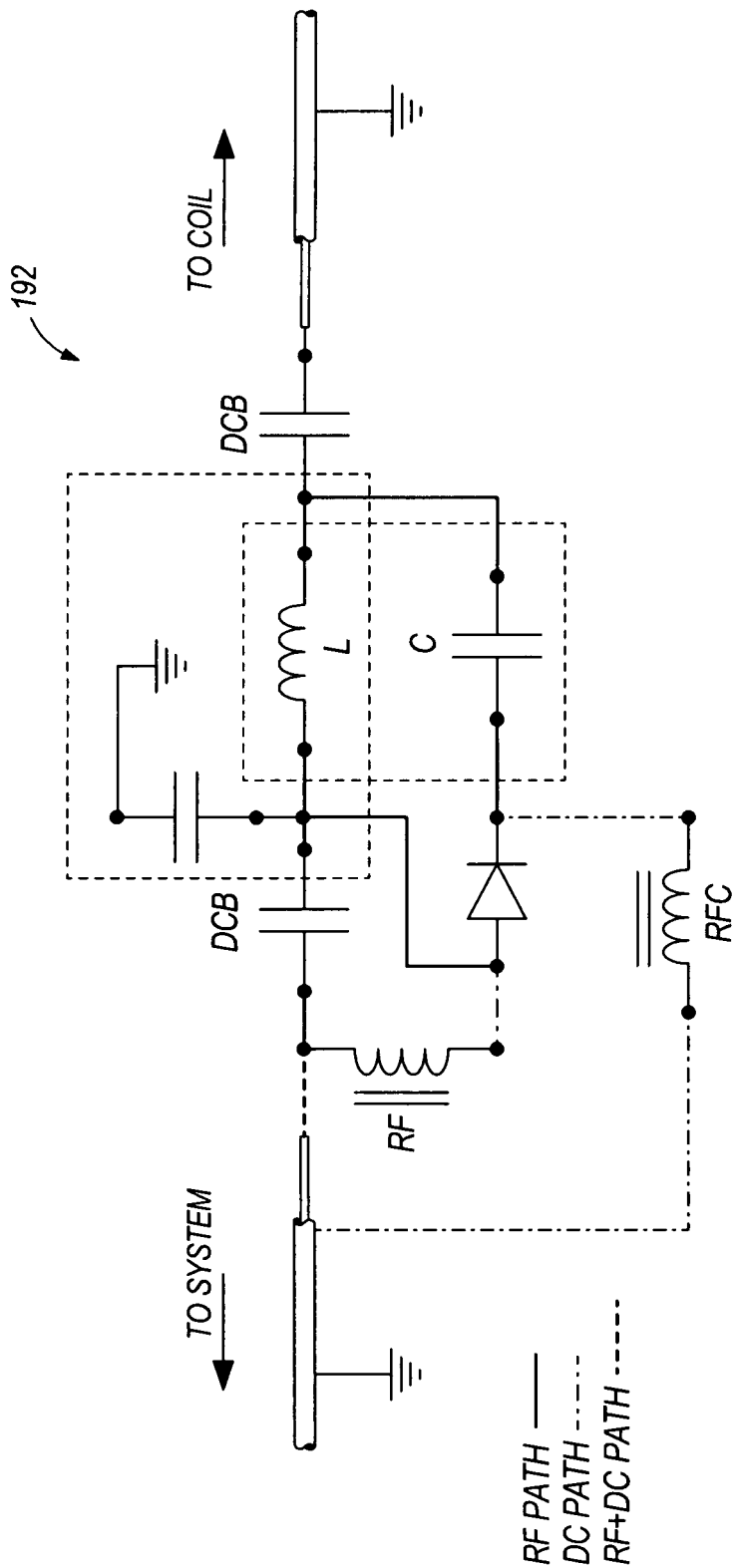
FIG. 38 a schematic representation of a decoupling circuit according to one embodiment of the present invention, described in Example 16.
Figure 39:
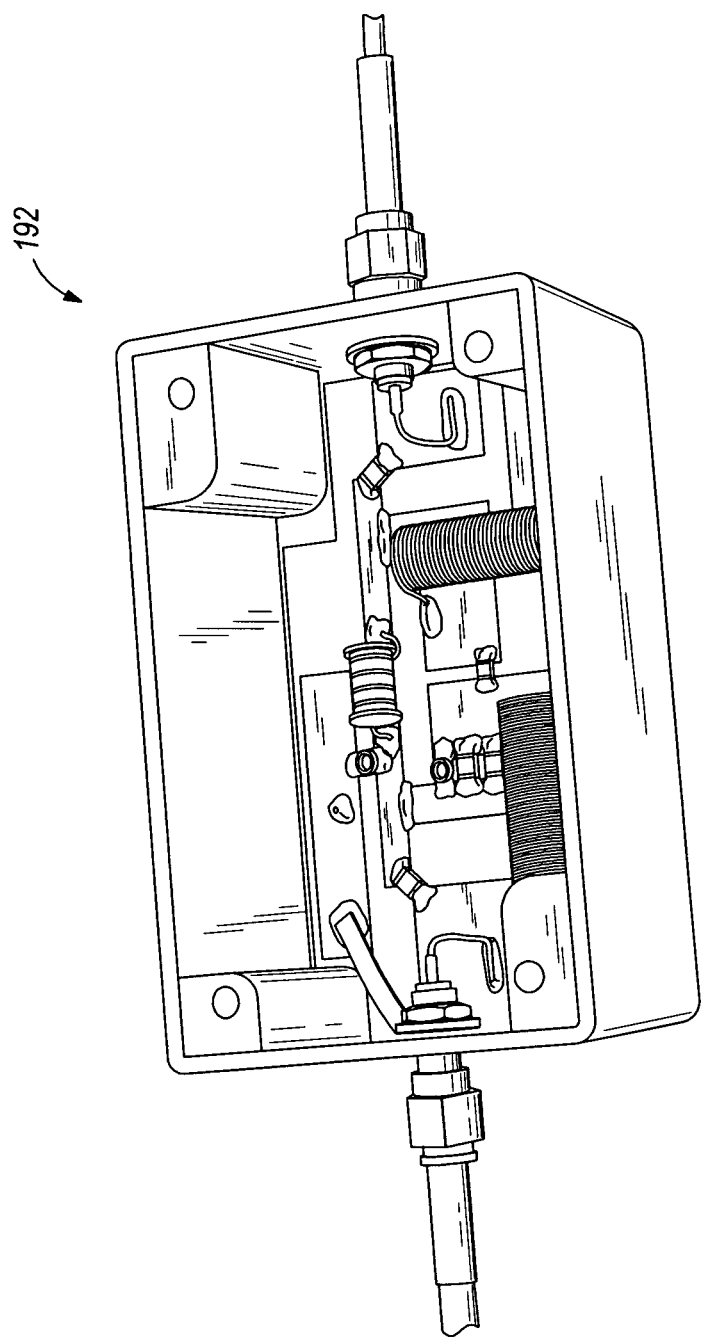
FIG. 39 is a perspective view of one embodiment of the decoupling circuit of FIG. 38.

A first embodiment of the decoupling circuit 192, namely decoupling circuit 192a, is described in Example 16 and illustrated in FIGS. 38 and 39. A second embodiment of the decoupling circuit 192, namely decoupling circuit 192b, is described in Example 18 and illustrated in FIGS. 46-48.

Some MRI systems of the present invention include components of both the MRI system 80 illustrated in FIG. 31 and the MRI system 180 illustrated in FIG. 32. For example, an MRI system of the present invention can include both the external RF coil 95, as shown in FIG. 31, and the imaging device 106, as shown in FIG. 32, to image a target object from outside and/or from within, either sequentially or simultaneously. Furthermore, in an MRI system that employs both the external RF coil 95 and the imaging device 106, the external RF coil 95 can be used to visualize the multi-mode medical device system 100, and the imaging device 106 can be used to acquire MR images from the point of view of the medical device 102.

As used herein and in the appended claims, the term "tracking" generally refers to identifying the location of a medical device, or a portion thereof, relative to a reference point, line, plane or volume in which the medical device is moved. For example, a medical device can be tracked as the medical device is moved relative to an imaging slice or volume (i.e., simultaneously or previously acquired) of a target object. Such an imaging slice or volume can be referred to as a "roadmap image" when used as a reference image for a tracking device. An imaging slice can be in any orientation of space. For example, an imaging slice can be taken in a coronal plane, a sagittal plane, an axial plane, an oblique plane, a curved plane, or combinations thereof.

A roadmap image can be acquired using a variety of imaging technologies, including, without limitation, X-ray, fluoroscopy, ultrasound, computed tomography (CT), MR imaging, positron emission tomography (PET), and the like, or combinations thereof. Tracking a medical device does not necessarily include acquiring an image of the medical device, but rather includes transmitting a signal, or feedback, indicative of the location of the medical device, or a portion thereof, to a receiver (e.g., the receiver 96 of the MRI system 80 shown in FIG. 31) capable of interpreting the signal. This information can be superimposed on an anatomical roadmap image of the area of the target object in which the medical device is being used. This type of tracking is sometimes referred to as "active tracking" among those of ordinary skill in the art. In some embodiments, the tracking can be accomplished in real time.

As used herein and in the appended claims, the term "field of view" is used to refer to the boundaries of an imaging slice (e.g., X and Y boundaries, if the imaging slice is in an X-Y plane). The field of view is essentially a window for imaging during MR imaging. If the imaging slice is a two-dimensional image, the imaging slice or the field of view of that imaging slice may need to be updated as a medical device is moved relative to the target object to account for the movement of the medical device in three-dimensional space. For example, a medical device may be imaged in an imaging slice that exists in a first coronal plane. A first field of view in the first coronal plane defines boundaries in the first coronal plane of what will be displayed during MR imaging (e.g., on a monitor or other display device). If a medical device is moved outside of the first field of view, but in the first coronal plane, a new field of view will be required to continue to follow the medical device as it moves in the first coronal plane. However, if the medical device is moved outside of the first coronal plane, a new imaging slice (i.e., in a second coronal plane parallel to the first coronal plane, either anterior or posterior to the first coronal plane) will be required to continue to follow the medical device. If the medical device is moved outside of the first coronal plane and the first field of view, a new field of view and a new imaging slice will be necessary to continue to follow the medical device as it moves.

To track a medical device, or a portion thereof, one or more tracking devices can be coupled to the medical device. When multiple tracking devices are used, they can be connected in series or in parallel. As used herein and in the appended claims, a "tracking device" (also sometimes referred to as an "active device") can include a variety of devices that are capable of being coupled to a medical device and of sending a signal that can be representative of their location. Thus, a tracking device can be tracked independently of being visualized. In some embodiments, the MR scanner can include the receiver (e.g., the receiver 96 of the MRI system 80 shown in FIG. 31) capable of receiving and interpreting the signal. For example, in some embodiments, the tracking device can be electrically coupled (i.e., wirelessly or via wires) to a receiver channel of an MR scanner. In such embodiments, the MR scanner can receive the feedback from the tracking device, and automatically update the imaging slice and/or the field of view relative to the tracking device to inhibit the tracking device from moving outside of the imaging slice and/or the field of view.

The MR scanner can adjust or update the field of view and/or the imaging slice based on the feedback from the tracking device in a variety of ways. For example, in some embodiments, the MR scanner can repeatedly re-center the field of view and/or the imaging slice on the tracking device. In some embodiments, the MR scanner can update the field of view and/or the imaging slice just as the tracking device approaches a boundary of the field of view and/or the imaging slice, respectively, to prevent the tracking device from moving outside of the field of view and/or the imaging slice. The location of the tracking device can be displayed in graphical form (e.g., as an icon) superimposed on a simultaneously or previously acquired roadmap image.

Figure 56:
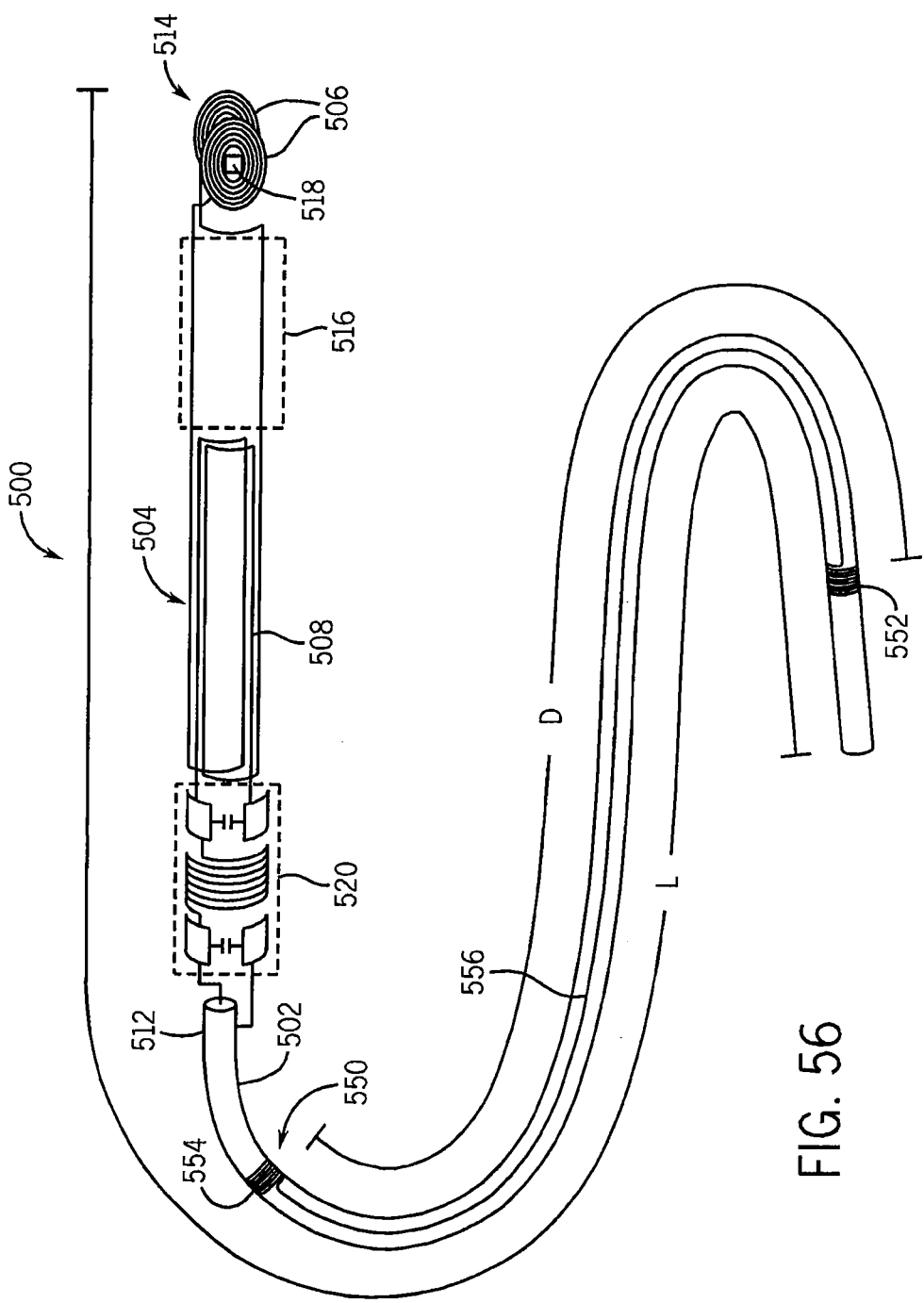
FIG. 56 is a schematic view of a multi-mode medical device system according to one embodiment of the present invention.
Figure 57:
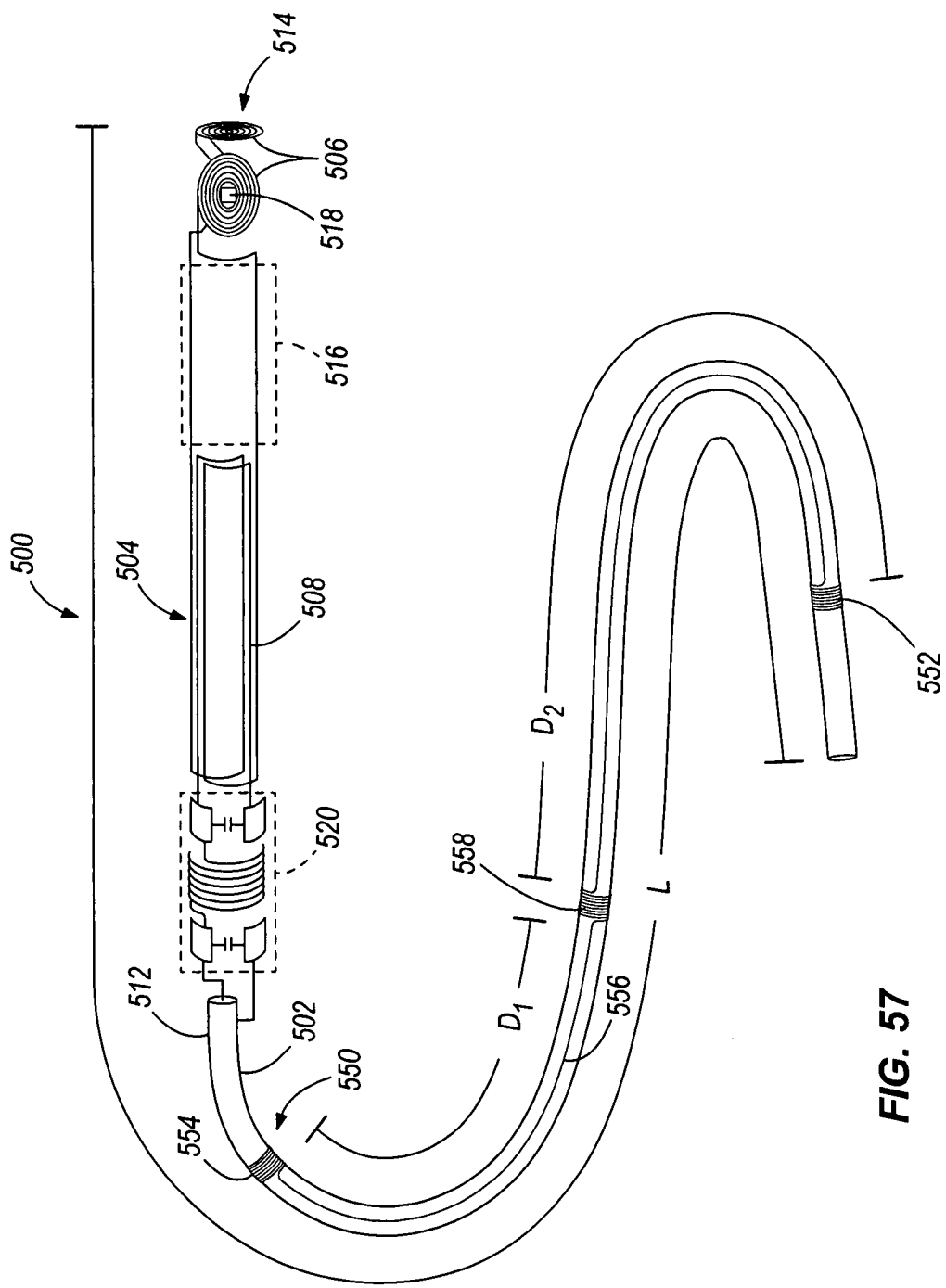
FIG. 57 is a schematic view of a multi-mode medical device system according to another embodiment of the present invention.

One example of a tracking device includes one or more solenoids or radio frequency (RF) coils coupled to the medical device. (If more than one RF coil is employed, they can be connected in series or in parallel.) For example, as shown in FIGS. 33-34, 43 and 52, one or more RF coils can be wound around and/or embedded onto a catheter. In addition, a Helmholtz pair can be positioned near the tip of the catheter as shown in FIGS. 56 and 57. To track an RF coil coupled to a medical device, a spatially non-selective RF pulse and a read-out gradient along a single axis give rise to a sharp peak in the Fourier-transformed signal due to the localized spatial sensitivity of the coil. The spectral position of this peak can be used to determine the coil position along the axis and if this is repeated for the remaining two axes, the 3-dimensional position of the coil can be obtained with a frequency up to 20 Hz. This coordinate information can then be superimposed as an icon on a roadmap image.

The advantages of tracking a medical device can include excellent temporal and spatial resolution. However, tracking methods typically allow visualization of only a discrete point(s) on the device. For example, in some cases, only the tip of the device is tracked. Although it is possible to incorporate multiple tracking devices (e.g., 4-8 on current clinical MR scanners) into a medical device, this allows for determination of the position of discrete points along the device. While this may be acceptable for tracking rigid biopsy needles, this can be a significant limitation for tracking flexible devices such as those used in endovascular therapy. For example, tracking discrete points along a catheter or guidewire can make it difficult to steer the long, flexible medical device in tortuous vessels.

As used herein and in the appended claims, the term "visualizing" or "visualization" refers to viewing a medical device, or a portion thereof, e.g., by using magnetic resonance imaging. For example, the use, manipulation and/or movement of a medical device within a target object can be observed, e.g., under MR guidance. Of course, visualizing a medical device also gives information regarding the location or position of the medical device, or a portion thereof. The acquisition of an image (e.g., an MR image), however, is necessary to visualize a medical device. Acquisition of an image is not necessary to track a medical device, or a portion thereof. In addition, tracking a medical device will usually not give any information about the size, shape or configuration of a medical device, whereas the size, shape, configuration, and other physical properties of a medical device can be evaluated by visualizing the medical device. Visualizing is sometimes referred to as "passive tracking" among those of ordinary skill in the art. When an object has been visualized, those skilled in the art may also refer to the object as having been imaged. Therefore, objects having MR-visibility or being MR-visible are sometimes referred to as having MR-imageability or being MR-imageable. To avoid confusion with internal imaging, which is defined in paragraph 87, an attempt has been made to use the terms visualization, MR-visibility and MR-visible, rather than imaging, MR-imageability or MR-imageable.

Some existing visualization methods exploit the fact that many medical devices, such as most endovascular devices, do not generally emit a detectable MR signal, which results in such a medical device being seen in an MR image as an area of signal loss or signal void. By observing and following the signal void, the position and motion of such a medical device can be determined. Since air, cortical bone and flowing blood are also seen in MR images as areas of signal voids, the use of signal void is generally not appropriate for visualizing devices used in interventional MR. In other words, signal voids are not the best method for medical device visualization since they can be confused with other sources of signal loss.

Another existing visualization technique utilizes the fact that some materials cause a magnetic susceptibility artifact (either signal enhancement or signal loss) that causes a signal different from the tissue in which they are located. In other words, the magnetic susceptibility can cause passive contrast between the device and surrounding tissues. Some catheters braided with metal, some stents and some guide-wires are examples of such devices. Susceptibility differences cause local distortions to the main magnetic field of an MRI system, and result in areas of signal loss surrounding the device. Susceptibility-induced artifacts depend on field strength, device orientation in the magnetic field, pulse sequence type and parameters, and device material. Another form of susceptibility-based visualization is the actively-controlled passive technique. This technique, which relies on artificially-induced susceptibility artifacts generated by applying a small direct current to a wire incorporated into the device, also suffers from shortcomings similar to those of the other aforementioned susceptibility-based techniques, even though it allows manipulation of artifact size by adjusting the amount of direct current to change the amount of local field inhomogeneity. One problem with the use of these techniques based on susceptibility artifacts is the fact that those used for localization of the device does not correspond precisely with the size of the device. This can make precise localization and visualization difficult.

A principal drawback of existing visualization techniques based on signal voids or susceptibility-induced artifacts is that visualization is dependent on the orientation of the device with respect to the main magnetic field of the MRI system.

Visualizing a medical device can be particularly useful for non-rigid or flexible medical devices, or for medical devices including a flexible portion. In some embodiments, a medical device includes a flexible portion that is capable of forming nonlinear configurations. As used herein and in the appended claims, the term "nonlinear configurations" refers to configurations of the medical device (particularly, of a flexible portion of the medical device) that cannot be defined by a straight line. For example, nonlinear configurations can include, but are not limited to, curves, loops, kinks, bends, twists, folds, and the like, or combinations thereof.

To visualize a medical device under MR guidance, at least a portion of the medical device can be capable of being imaged under MR guidance. For example, a "visualizing device" can be coupled to or applied to a surface of a medical device. As used herein, the term "coupling" or "coupled" is intended to cover visualizing devices that are coupled to and/or applied to a medical device. A variety of visualizing devices can be coupled to a medical device, including, without limitation, at least one of an MR-visible coating (e.g., as described in Example 17 and shown in FIG. 34), a wireless marker (e.g., a resonant loop, as described in Examples 16, 18 and 19 and shown in FIGS. 33-34, 43 and 52, respectively), and the like, and combinations thereof. As used herein and in the appended claims, the terms "MR-visible" and "MR-imageable," as well as the terms "MR-visibility" and "MR-imageability," can be used interchangeably. In some embodiments, the MR-visible coating is coupled to a medical device by filling the medical device with the MR-visible coating, rather than coating a portion of an outer surface of a medical device with the MR-visible coating.

The use of some visualizing devices can be limited due to the fact that no feedback is sent from the visualizing device to the MR scanner to allow the MR scanner to interactively adjust the imaging slice/volume to follow the medical device in real time. As a result, visualizing devices are sometimes referred to as "passive devices."

Endovascular interventional procedures performed under MR guidance can include not only the visualization of catheters/guidewires but also the acquisition of the relevant anatomical images that show the medical device in relation to its surroundings. These anatomical roadmap images can be obtained using contrast agents. Some visualizing devices can essentially disappear from view in the MR image when contrast agent is used, and cannot be visualized again until the contrast agent washes away. Therefore, until the contrast agent washes away, which can take about 20-30 minutes, the visualization of the visualizing devices can become very difficult, if not impossible. Other visualizing devices, however, can still be visualized in an MR image even when contrast agent is present. As a result, two or more types of visualizing devices can be coupled to or applied to the same medical device to enhance the visualization of the medical device throughout a procedure (i.e., during the presence and absence of contrast agents).

One example of a visualizing device that can be applied to a medical device includes an MR-visible coating capable of emitting magnetic resonance signals. The MR-visible coating can be used to coat at least a portion of a medical device so that the respective portion of the medical device is readily visualized in MR images. Such MR-visible coatings generally include paramagnetic ions. MR-visible coatings exploit the T1-shortening effect of MR contrast agents such as gadolinium-diethylene triamine pentaacetic acid (Gd3+-DTPA). MR-visible coatings allow visualization of the entire length of the device, independent of its orientation in the main magnetic field.

The MR-visible coatings are also of value for providing improved visibility in interoperative MR of surgical instruments after being coated with the signal-enhancing coatings of the present invention. The improved visualization of implanted devices so coated, e.g., stents, coils and valves, may find a whole host of applications in diagnostic and therapeutic MR. These attributes of the coating in accordance with the present invention are achieved through a novel combination of physical properties and chemical functionalities. The MR-visible coatings, methods of coating medical devices to allow them to be visualized under MR guidance, and examples thereof are described in greater detail below.

In some cases, MR-visible coatings can essentially disappear from view when contrast agents are present. Because MR-visible coatings and contrast agents use the same principle to allow visibility under MRI (i.e., the shortening of the T1 relaxation time of water protons in the vicinity), the presence of contrast agents can compete with the visibility of the MR-visible coatings under MRI. As a result, the ability to visualize an MR-visible coating under MRI generally depends on the concentration of the contrast agent used in the MR-visible coating as compared to the concentration of the contrast agent that is injected or otherwise administered. Increasing the concentration of the contrast agent, whether in the MR-visible coating or in the administrable contrast agent, decreases the T1 relaxation time. Thus, if the concentration of contrast agent in the MR-visible coating is different from that of the administrable contrast agent, the MR-visible coating may cause a different T1 relaxation time, and the MR-visible coating (and the portion of the medical device to which the MR-visible coating is applied) may still remain visible under MRI in the presence of the contrast agent. However, visualization of the MR-visible coating can be difficult, if not impossible, when contrast agents having concentrations similar to that of the MR-visible coating are present.

A synergistic effect can be observed when a tracking device (such as an RF coil) is coupled to a portion of a medical device to which an MR-visible coating has been applied. Particularly, the MR-visible coating can serve as an internal signal source for the tracking device. An MR-visible coating can cause the T1 relaxation time of water protons in its vicinity to be lower than those of surrounding tissue. This difference in T1 relaxation time can be observed during MRI. In addition, an MR-visible coating increases the number, and density, of protons in a region corresponding to the location of the MR-visible coating. Incorporation of an MR-visible coating onto a medical device further amplifies the signal in the vicinity of the tracking device, because the MR-visible coating causes a lowering of T1 relaxation time of the water protons in and around the vicinity of the tracking device, in addition to increasing the number of protons in the vicinity of the tracking device. The signal associated with the tracking device is amplified by the MR-visible coating by virtue of shortening T1 and increasing the number of protons in the vicinity of the tracking device. Thus, the signal-to-noise ratio of the signal associated with the tracking device is improved.

A similar synergistic effect may be observed when a tracking device is used in the presence of contrast agents. Because contrast agents cause a lowering of the T1 relaxation time of water protons in their vicinity, and increase the number of protons in their vicinity, a contrast agent used simultaneously with a tracking device will also amplify the signal associated with the tracking device. However, a medical device that includes a tracking device and an MR-visible coating will exhibit this synergistic effect throughout MR imaging, and not only temporarily, as is the case with contrast agents. Thus, a medical device system that includes a tracking device and a visualizing device, such as an MR-visible coating, is more robust, reliable and effective than simply using contrast agents simultaneously with tracking a tracking device.

Another example of a visualizing device that can be coupled to a medical device includes a wireless marker. The term "wireless marker" refers to a device that can be coupled to a medical device and which can become visible in an MR image because they cause an increase in the RF field in their vicinity and hence increase the magnetization of the neighboring nuclear spins due to strong coupling to a similarly tuned external or whole body RF coil in a MR scanner.

Accordingly, such a device can be used to visualize at least a portion of a medical device in an MR image. Wireless markers can include a variety of passive electrical devices that are capable of increasing the concentration of RF magnetic fields (i.e., amplifying the MRI signal) in its vicinity, including, without limitation, an inductively coupled resonator, which is also sometimes referred to as a "resonant circuit" or "resonant loop." Inductively coupled resonators can include resonant tuned circuits that include an inductor coil (or loop) and a capacitor connected together and designed to resonate at a certain frequency. The resonant frequency is determined by choosing the inductive (L) and capacitive (C) values so that the equation ($f=1/(2\pi LC)$) comes true. An inductively coupled resonator functions by strongly coupling to a similarly-tuned external/whole body RF coil (such as the RF transmit coil 91 and the RF receive coil 95 shown in FIG. 31), when placed and excited within the bore or imaging region 98 of the MRI system 80. The coupling results in a concentration of RF magnetic fields in the vicinity of the wireless marker. Hence, when the transmit power of the RF transmit coil 91 is adjusted to a certain low power, a small flip angle (1-10°) is induced in all parts of the sample except in the vicinity of the wireless marker, where a large flip angle (90°) is induced due to the concentration of the RF magnetic fields, therefore resulting in a bright region in the resulting MR image. The bright region in the resulting MR image results because signal that is generated or produced in MRI is proportional to the effective flip angle. Because this bright region is a result of signal amplification due to the increased effective flip angle, the visualization of wireless markers is not disturbed by the presence of contrast agents. As a result, wireless markers coupled to at least a portion of a medical device allow the respective portion of the medical device to be visualized under MR guidance, even in the presence of contrast agent, and thus, wireless markers obviate waiting until contrast agent is washed away.

An inductively coupled resonator can be tuned to resonate at the Larmor or processing frequency of the Hydrogen protons. For example, the Larmor frequency of Hydrogen protons at 1.5 T is 64 MHz.

In some embodiments of the present invention, the medical device is readily visualized under MR guidance throughout, or substantially throughout, a procedure because the medical device includes both an MR-visible coating applied to at least a portion of it, and one or more wireless markers coupled to at least a portion of it. In some embodiments, the entire medical device is coated with the MR-visible coating, and one or more wireless markers are coupled to the medical device. In such embodiments, the nonlinear configurations of the medical device can be readily visualized under MR guidance due to the MR-visible coating when contrast agent is not present, and, in the presence of contrast agent, the wireless marker(s) can be used to elucidate the size and configuration of the medical device. The wireless marker(s) can also be used to visualize at least a portion of the medical device when contrast agent is not present.

A synergistic effect can be observed when a wireless marker is coupled to a portion of a medical device to which an MR-visible coating has been applied. Particularly, the MR-visible coating can serve as an internal signal source for the wireless marker. Incorporation of an MR-visible coating onto a medical device further amplifies the signal inside the inductively coupled resonator because the MR-visible coating causes a lowering of T1 relaxation time of the water protons in and around the vicinity of the wireless marker, and also increases the number of protons in the vicinity of the wireless marker. These two different effects (i.e., the effects from each of the wireless marker and the MR-visible coating) act together to enhance the visibility in T1 weighted MR images beyond what is possible with either visualizing device alone. Because of the high signal caused by the MR-visible coating by virtue of shortening T1 and increasing the number of protons in the vicinity, the entirety of the wireless marker can be readily visualized. As a result, the signal associated with the wireless marker is amplified by the MR-visible coating, and the signal-to-noise ratio of the signal associated with the wireless marker is improved.

A similar synergistic effect can be observed when a wireless marker is used in the presence of contrast agents. Because contrast agents cause a lowering of the T1 relaxation time of water protons in their vicinity, and increase the number of protons in their vicinity, a contrast agent used simultaneously with visualization of a wireless marker will also amplify the signal associated with the wireless marker. Example 17 and FIG. 42 describe and illustrate a study that was performed to illustrate the synergistic effect between a wireless marker and an MR-visible coating. Although the study described in Example 17 includes filling a catheter with an MR-visible coating material, the effect would be substantially the same if the MR-visible coating was applied to the outer surface of a medical device. However, a medical device that includes a wireless marker and an MR-visible coating will exhibit this synergistic effect throughout MR imaging, and not only temporarily, as is the case with contrast agents. In addition, a wireless marker functions by appearing brighter than the surrounding tissue. When contrast agents are used, the background signal from the surrounding tissue is already enhanced, and the effects of the wireless marker are minimized. However, the effects of the wireless marker are not minimized in this way when used in combination with an MR-visible coating, because the MR-visible coating does not affect the background signal. Thus, a medical device system that includes both types of visualizing devices is more robust, reliable and effective than simply using contrast agents simultaneously with visualizing a wireless marker.

Figure 35:
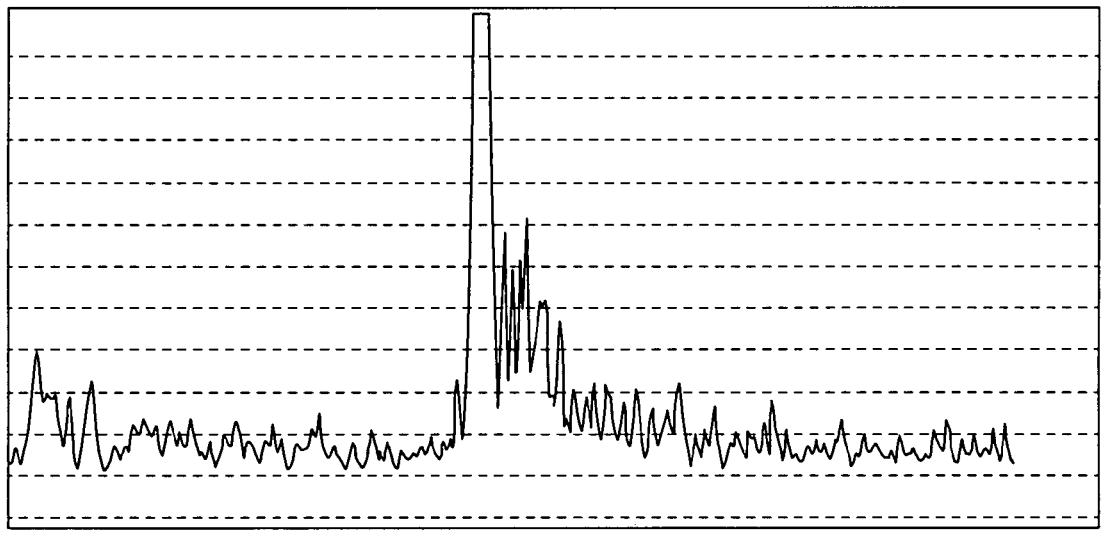
FIG. 35 is a one-dimensional Fourier transform of an RF signal induced by proton spins, described in Example 16.
Figure 36:
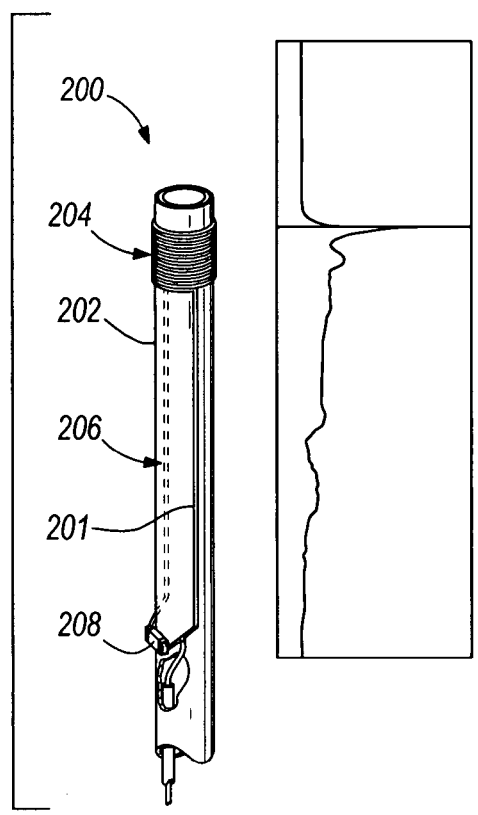
FIG. 36 is a representation of a profile of the multi-mode medical device system of FIGS. 33 and 34, described in Example 16.
Figure 37:
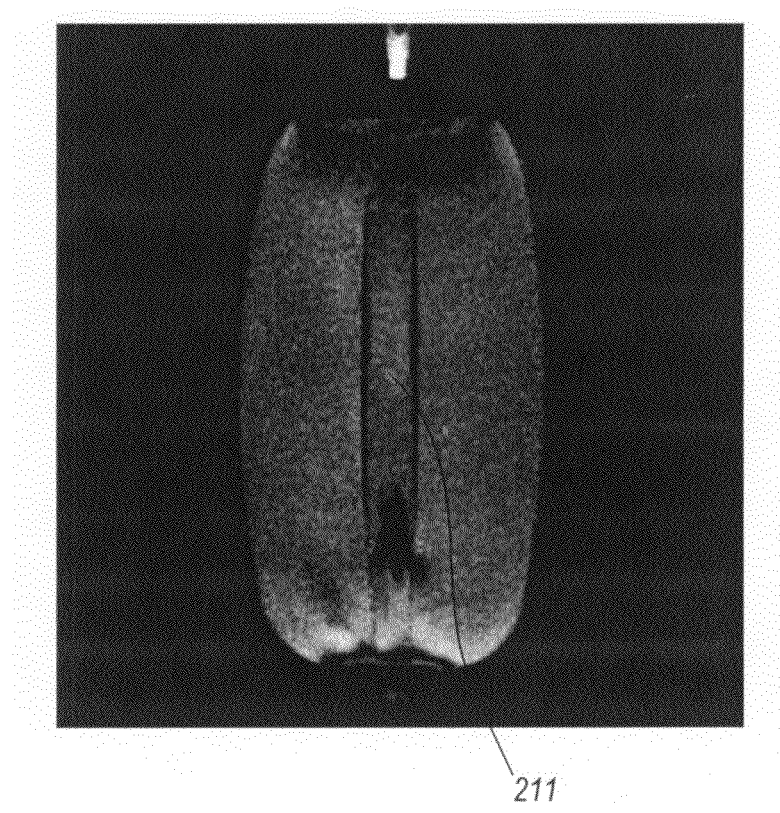
FIG. 37 is a temporal MR snapshot of the multi-mode medical device system of FIGS. 33 and 34 in tracking mode, in a phantom.
Figure 40:
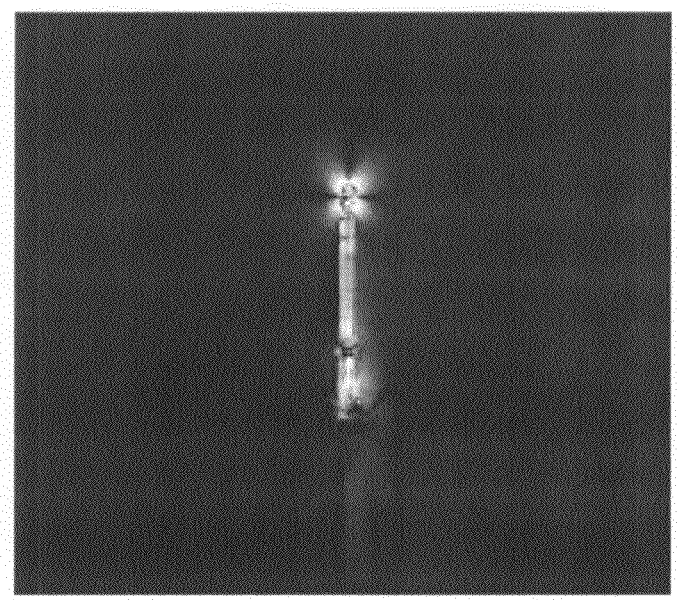
FIG. 40 is a sagittal image of a phantom, obtained using an imaging device during an internal imaging mode of the multi-mode medical device system of FIGS. 33 and 34, described in Example 16.
Figure 41:
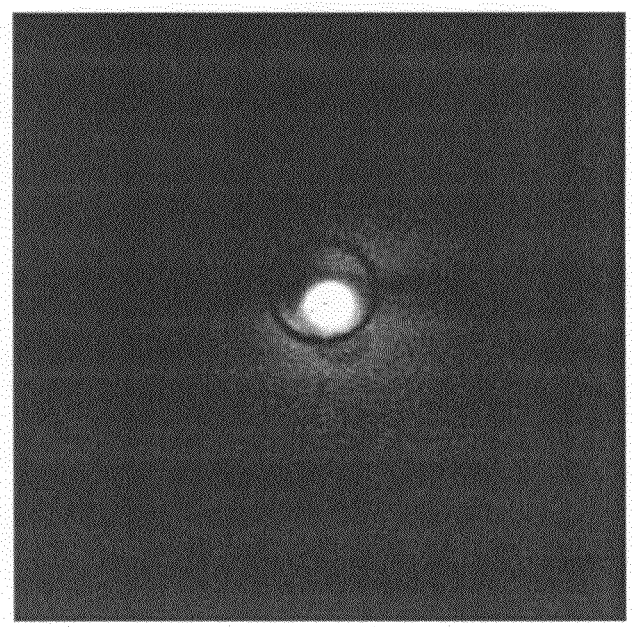
FIG. 41 is an axial image of a phantom, obtained using an imaging device during an internal imaging mode of the multi-mode medical device system of FIGS. 33 and 34, described in Example 16.
Figure 44:
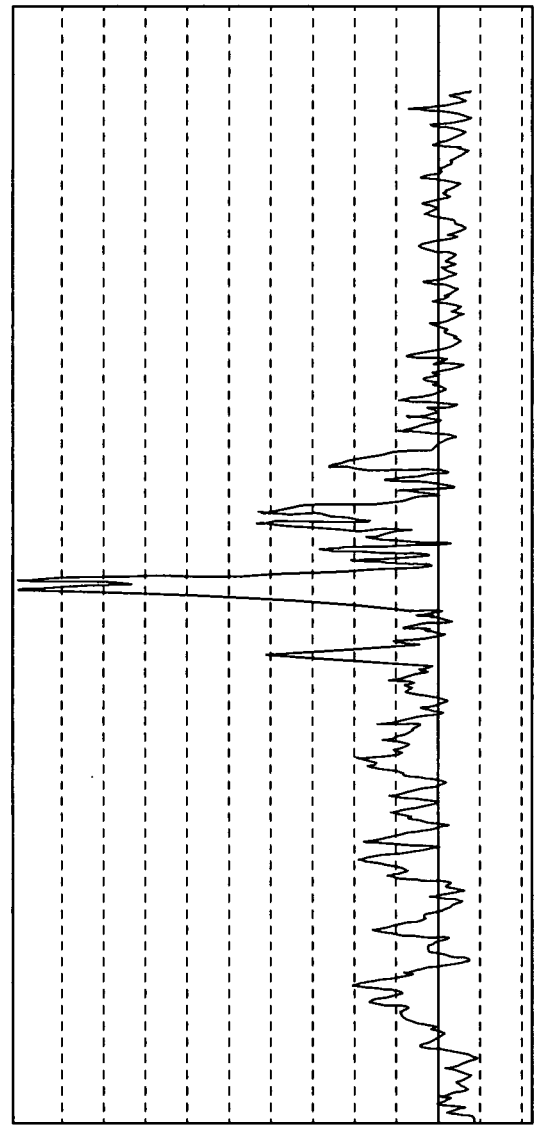
FIG. 44 is a one-dimensional Fourier transform of an RF signal induced by proton spins, described in Example 18.
Figure 45:
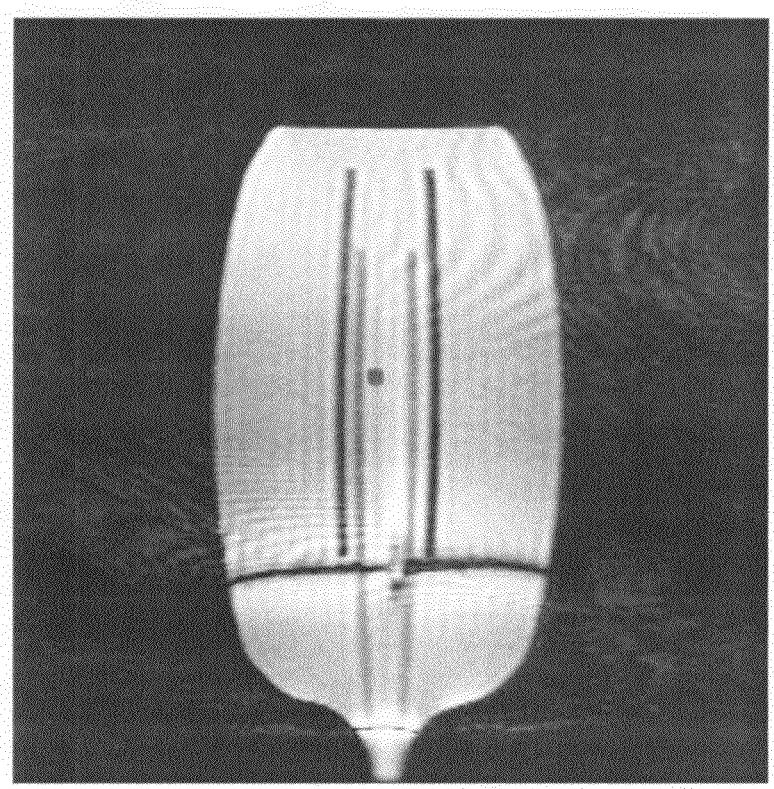
FIG. 45 is a temporal MR snapshot of the multi-mode medical device system of FIG. 43 in tracking mode, in a phantom.

Multi-mode medical device systems according to the present invention are capable of MR imaging and of being tracked under MR guidance. The multi-mode medical device systems can include a medical device and an electrical circuit coupled to the medical device. The electrical circuit can include a tracking device and an imaging device connected together and used in different operating modes of the multi-mode medical device system. The operating modes can be operated sequentially or simultaneously. The tracking device can be configured to transmit a signal to an MRI system that is representative of the location of the tracking device. An example of this is shown in FIGS. 35-37 and described in Example 16, under 'Tracking Mode'. Another example is shown in FIGS. 44-45 and described in Example 18, under 'Tracking Mode.' The imaging device can be configured to internally image anatomical structures from the point of the view of the medical device. Examples of images that can be obtained using an imaging device of a multi-mode medical device system according to the present invention are shown in FIGS. 40-41 (and described in Example 16, under 'Imaging Mode'), in FIGS. 49-50 (and described in Example 18, under 'Imaging Mode'), and in FIGS. 53-54 (and described in Example 19, under 'Imaging Mode'). The tracking device and the imaging device can be coupled to the medical device, can be electrically coupled to one another and integrated to form a multi-mode medical device system that can perform MR imaging of a target object, and can also be tracked.

The electrical circuit includes a tracking and imaging circuit, can comprise integrated tracking and imaging devices, and can be electrically coupled to a channel in a receiver of an MRI system (e.g., the receiver 196 of the MRI system 180 shown in FIG. 32). As described above, and depending on the type of tracking device used, the tracking device can send a signal indicative of the position or location of the tracking device relative to the roadmap image to a receiver in an MRI system. As described in Example 16 below, in some embodiments, the signal can be sent from the tracking device to a receiver via a coaxial cable positioned within a lumen of a medical device. When the location of the tracking device relative to the roadmap image has been determined, the location of the tracking device can be superimposed on the roadmap image as an icon to indicate the position of the tracking device relative to the roadmap image. Furthermore, the imaging device can send signals indicative of the localized magnetic fields in the vicinity of the imaging device to a decoupling circuit (e.g., the decoupling circuit 192 shown in FIG. 32) that includes a matching portion, which can then send signals to a receiver of an MRI system (e.g., the receiver 196 of the MRI system 180). The signals from the imaging device can be used to generate MR images from the point of view of the medical device.

Because the tracking device and imaging device can be integrated, and can each form part of the same electrical circuit, the tracking device and the imaging device can be connected to an MRI system (e.g., the MRI system 180 of FIG. 32), and particularly, to a receiver (e.g., the receiver 196 of the MRI system 180) via a pair of (or two) wires. In other words, the tracking device and the imaging device can be connected to the same receive channel of an MRI system. If, instead, the tracking device and the imaging device were not integrated, each device would need to be connected to the MRI system separately, which could require, at a minimum, two pairs of (or four) wires. As a result, the embodiments employing integrated tracking and imaging devices require fewer connections and take up fewer receive channels of an MRI system to perform similar functions as embodiments employing non-integrated tracking and imaging devices.

Some existing systems employ one or more coils that are capable of tracking or internal imaging, and require switching between these two operating modes. In contrast, the electrical circuit of the multi-mode medical device system can include a tracking portion and an internal imaging portion, such that the multi-mode medical device system can include integrated, but dedicated, tracking and imaging devices, and may not require switching between tracking and internal imaging. Furthermore, with the multi-mode medical device systems of the present invention, tracking and internal imaging can be performed simultaneously, if desired.

In addition, the multi-mode medical device systems can be visualized under MR guidance. In some embodiments, the imaging device can be configured to be visualized under MR guidance. In some embodiments, the multi-mode medical device system can further include a visualizing device. Such a visualizing device can be a part of the integrated circuit, or it can be separate therefrom. Thus, a third operating mode of the multi-mode medical device systems of the present invention can include visualizing. Furthermore, with the multi-mode medical device system of the present invention, tracking, visualizing and internal imaging can be performed simultaneously by using an external receive coil (e.g., the RF receive coil 95 shown in FIG. 31) simultaneously with the multi-mode medical device system, if desired.

Figure 42:
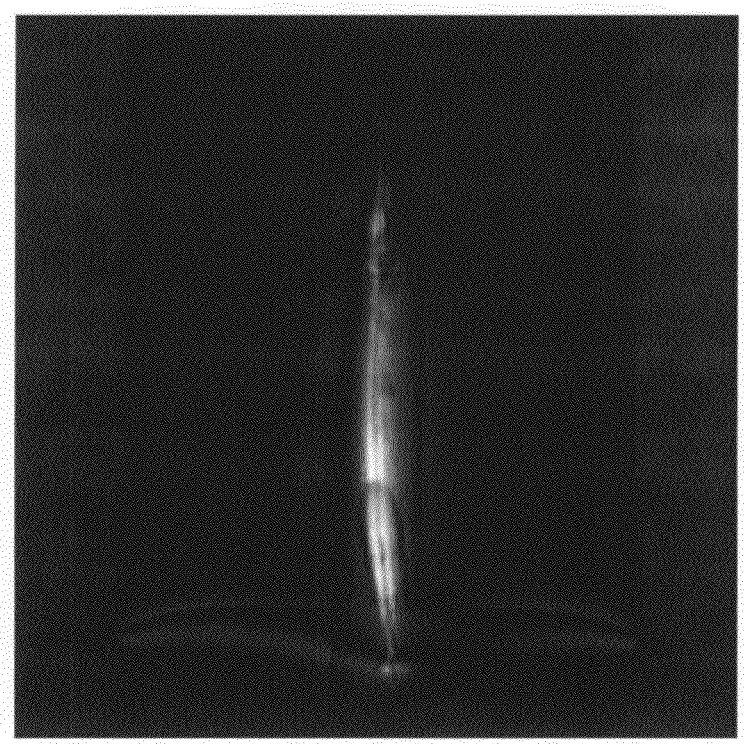
FIG. 42 is a temporal MR snapshot of the multi-mode medical device system of FIGS. 33 and 34 in visualizing mode, in a phantom.
Figure 51:
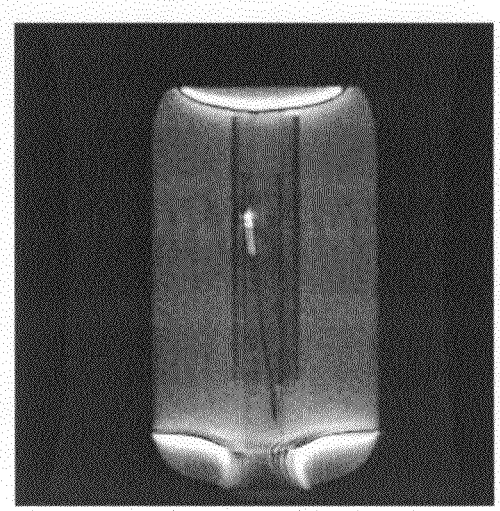
FIG. 51 is a temporal MR snapshot of the multi-mode medical device system of FIG. 43 in visualizing mode, in a phantom.
Figure 55:
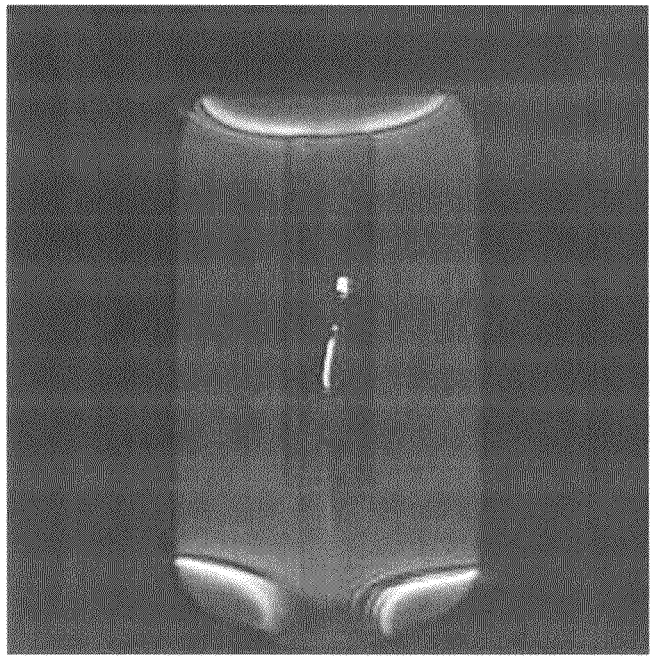
FIG. 55 is a temporal MR snapshot of the multi-mode medical device system of FIG. 52 in visualizing mode, in a phantom.

The electrical circuit of the multi-mode medical device systems of the present invention can be operated in three different modes, sequentially or simultaneously, to allow the multi-mode medical device system to be tracked and visualized under MR guidance, and to produce MR images of a target object from the point of view of the medical device. In a visualizing mode, the imaging device can function as a visualizing device, such as a wireless marker (e.g., an inductively-coupled resonator or resonant loop). Thus, the imaging device can also be referred to as an imaging/visualizing device. In embodiments in which the imaging device includes an inductively-coupled resonator, the imaging device can be disconnected from the receiver of the MRI system during visualizing mode, and inductively-coupled to an external RF coil, such as the RF transmit coil 91 and/or the RF receive coil 95 (which may or may not be the same as the RF transmit coil 91) of FIG. 31. The imaging device can receive RF signals from the external RF transmit coil and cause an increase in the RF field in the vicinity of the visualizing device to cause that region in the target object to appear brighter, or different, from the rest of the target region in an MR image. Examples of inductively-coupled resonators visualized under MR guidance are shown in FIGS. 42, 51 and 55 and described in Examples 16, 18 and 19, respectively, under 'Visualizing Mode.'

Figure 33:
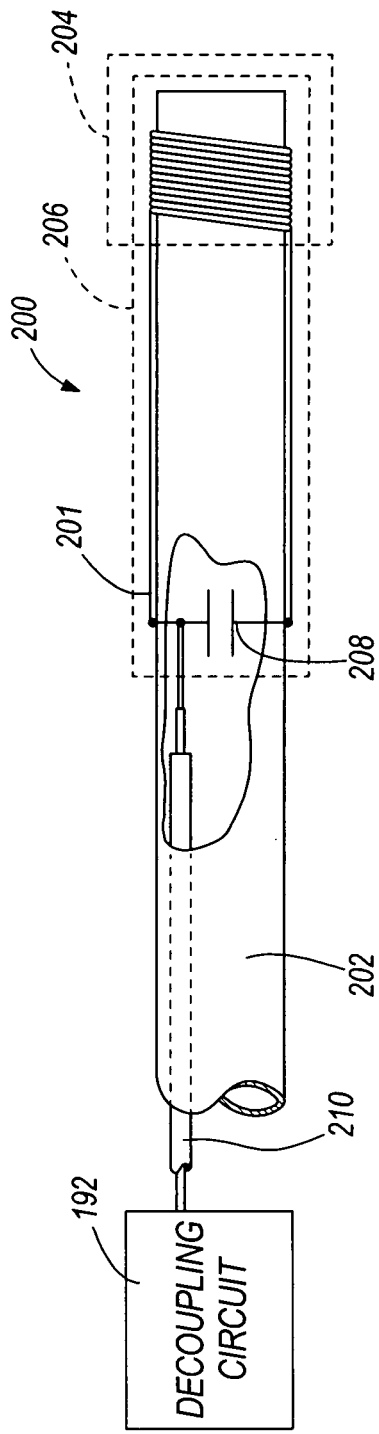
FIG. 33 is a partially schematic cut-away view of a multi-mode medical device system according to one embodiment of the present invention, described in Example 16, the multi-mode medical device system shown electrically coupled to a decoupling circuit.
Figure 34:
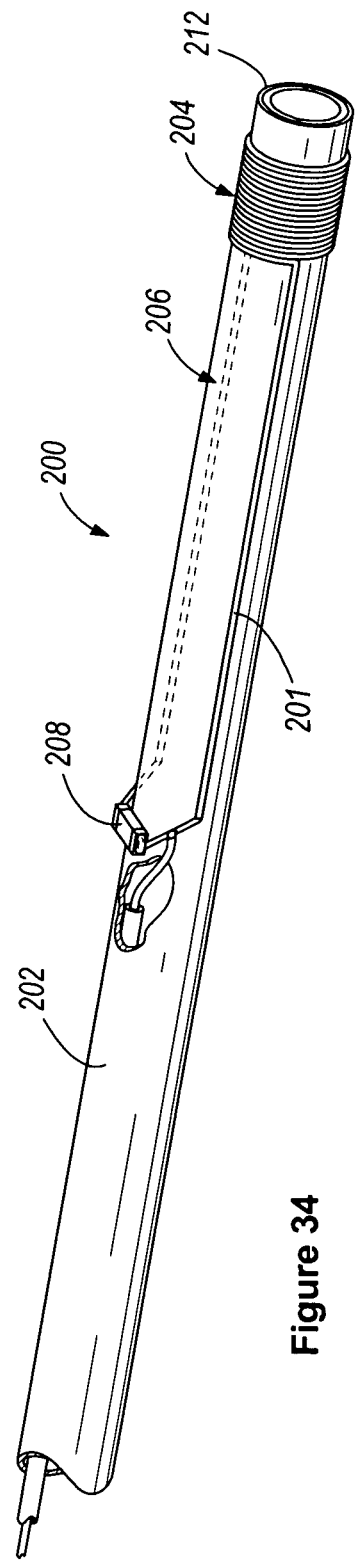
FIG. 34 is a perspective view of the multi-mode medical device system of FIG. 33.

In some embodiments, the electrical circuit of the multi-mode medical device system can be formed of wires (e.g., as described in Example 16 and shown in FIGS. 33-34). In some embodiments, the electrical circuit can be formed at least partially by a printed circuit board, or a flexible circuit. In some embodiments, the electrical circuit can be formed at least partially by a semiconductor integrated circuit (IC). In some embodiments, the electrical circuit can be formed at least partially by a microelectromechanical system (MEMS) that can include mechanical elements, sensors, actuators, and/or electronics on a common silicon substrate, made by microfabrication technology.

In some embodiments, the multi-mode medical device system can include a plurality of the above-described electrical circuits. For example, if the medical device employed is relatively long, a plurality of imaging and tracking electrical circuits may be coupled to the medical device along the length of the medical device to allow tracking, internal imaging and/or visualizing at a variety of positions along the length of the medical device.

In some embodiments, the multi-mode medical device system can include more than one visualizing device to improve the visualization of the medical device under MR guidance. For example, in some embodiments, the multi-mode medical device system can include an additional visualizing device applied to a substantial portion of the medical device to allow a substantial portion of the medical device to be visualized, at least, when contrast agent is not present. For example, the multi-mode medical device system can include an MR-visible coating applied to a surface of the medical device. Such multi-mode medical device systems can be visualized in the presence of contrast agents (e.g., by using the imaging device of the above-described electrical circuit in visualizing mode) and in the absence of contrast agents (e.g., by using the imaging device in visualizing mode or via the MR-visible coating). The synergistic effects described above between an MR-visible coating and a tracking device, or between an MR-visible coating and a wireless marker can also be observed between an MR-visible coating and the tracking device of the electrical circuit or between an MR-visible coating and the imaging device/visualizing device of the electrical circuit. Specifically, the MR-visible coating can act as an internal signal source and increase the amplitude of the resulting signal from the tracking device and/or the imaging/visualizing device. The multi-mode medical device system can include a plurality of additional visualizing devices.

In addition, in some embodiments, the multi-mode medical device system can include one or more additional tracking devices coupled to a portion of the medical device. Such multi-mode medical device systems can be tracked using the tracking device of the above-described electrical circuit, or using one of the additional tracking devices. For example, the electrical circuit can be positioned near a tip of a relatively long medical device, and additional tracking devices can be coupled to the medical device at various positions along the length of the medical device.

In some embodiments of the present invention, the following exemplary procedure can be performed using the multi-mode medical device system: 1) A multi-mode medical device system according to present invention can be tracked and/or visualized as it progresses (e.g., through the vasculature) towards a target region by detecting MR signals to determine and/or monitor the position of the multi-mode medical device system. 2) When the multi-mode medical device system has reached the target region, the same multi-mode medical device system may then be used to obtain high resolution images of the region and its surroundings, which may assist an interventional radiologist in accurately assessing disease and planning an appropriate therapeutic strategy. 3) Using the same multi-mode medical device system, a therapeutic procedure, such as the treatment of an aneurysm could be carried out, for example, by deploying coils or stents, delivering an embolic agent, or combinations thereof. 4) When the therapeutic procedure has been completed, the outcome of the therapeutic procedure can be assessed using the same multi-mode medical device system by acquiring high resolution images of the treated region. 5) Finally, after the above steps 1-4 have been performed, the multi-mode medical device system could be removed, such that all of the steps necessary to perform the therapeutic procedure under MR guidance were performed in a single-pass.

Examples 16-19 below further illustrate examples of multi-mode medical device systems according to the present invention, and methods of manufacturing and using such multi-mode medical device systems.

MR-Visible or MR-Imageable Coatings

Examples of suitable coatings for use with the invention can be found in U.S. Pat. Nos. 6,896,873 and 6,896,874, which are both hereby fully incorporated by reference. The present invention generally provides a process for coating medical devices so that the devices are readily visualized, particularly, in T1 weighted magnetic resonance images. Because of the high contrast signal caused by the coating, the entirety of the coated devices may be readily visualized during, e.g., an endovascular procedure.

In one aspect, the present invention provides a method of coating the surface of medical devices with a coating which is a polymeric material containing a paramagnetic ion, which coating is generally represented by formula (I):

P—X-L-Mn+     (I)

wherein P represents a polymer surface of a device such as a catheter or guide-wire, X is a surface functional group, L is a ligand, M is a paramagnetic ion and n is an integer that is 2 or greater. The polymer surfaces P may be that of a base polymer from which a medical device is made such as a catheter or with which a medical device is coated such as guide-wires. It is understood that a medical device may be suitably constructed of a polymer whose surface is then functionalized with X, or a medical device may be suitably coated with a polymer whose surface is then appropriately functionalized. Such methods for coating are generally known in the art.

To allow a sufficient degree of rotational freedom of the chelated complex, L-Mn+, the coating optionally contains a linker or spacer molecule J, and is generally represented by the formula (II):

P—X-J-L-Mn+     (II)

wherein P, X, L and M are as described above and J is the linker or spacer molecule which joins the surface functional group X and the ligand L, i.e., J is an intermediary between the surface functional group X and the ligand L. The polymer P may be a base polymer from which a medical device is made.

P is suitably any polymer substrate including, but not limited to, polyethylene, polypropylene, polyesters, polycarbonates, polyamides such as Nylon™, polytetrafluoroethylene (Teflon™) and polyurethanes that can be surface functionalized with an X group. Other polymers include, but are not limited to, polyamide resins (more particularly, 0.5 percent), polyamino undecanoic acid, polydimethylsiloxane, polyethylene glycol (200, 600, 20,000), polyethylene glycol monoether, polyglycol nitroterephthalate, polyoxyethylene lauryl ether, polyoxyl castor oil, polypropylene glycol, polysorbate 60, a mixture of stearate and palmitate esters of sorbitol copolymerized with ethylene glycol, polytetrafluoroethylene, polyvinyl acetate phthalate, polyvinyl alcohol and polystyrene sulfonate. It is noted that some polymer surfaces may need to be coated further with hydrophilic polymer layers. P may be a solid polymer. For example, P in the above formula represents a base solid polymer substrate which may stand for an extant medical device such as a catheter.

J is suitably a bifunctional molecule, e.g., a lactam having an available amino group and a carboxyl group, an α,ω-diamine having two available amino groups or a fatty acid anhydride having two available carboxyl groups. J may also be a cyclic amide. J covalently connects ligand L to surface functional group X.

X is suitably an amino or carboxyl group.

L is suitably any ligand or chelate which has a relatively high (e.g., >1020) stability constant, K, for the chelate of ligand-paramagnetic ion coordination complex. Such ligands include but are not limited to diethylenetriaminepentaacetic acid (DTPA), 1,4,7,10-tetracyclododecane-N,N',N'',N'''-tetraacetic acid (DOTA) and 1,4,8,11-tetraazacyclotradecane-N,N',N'',N'''-tetraacetic acid (TETA). Other ligands or chelates may include diethylenetriaminepentaacetic acid-N,N'-bis(methylamide) (DTPA-BMA), diethylenetriaminepentaacetic acid-N,N'-bis(methoxyethylamide) (DTPA-BMEA), s-4-(4-ethoxybenzyl)-3,6,9-tris[(carboxylatomethyl)]-3,6,9-triazaundecanedionic acid (EOB-DTPA), benzyloxypropionictetraacetate (BOPTA), (4R)-4-[bis(carboxymethylamino]-3,6,9-triazaundecanedionic acid (MS-325), 1,4,7-tris(carboxymethyl)-10-(2'-hydroxypropyl)-1,4,7,10-tetraazacyclododecane (HP-DO3A), and DO3A-butrol.

The structures of some of these chelates follow:

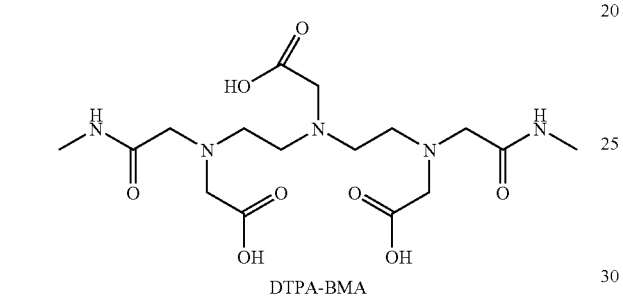

DTPA-BMA

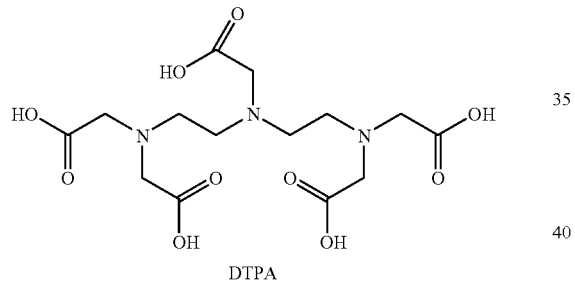

DTPA

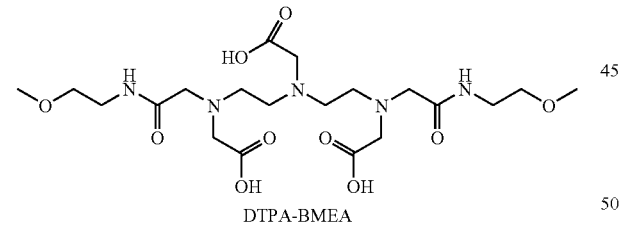

DTPA-BMEA

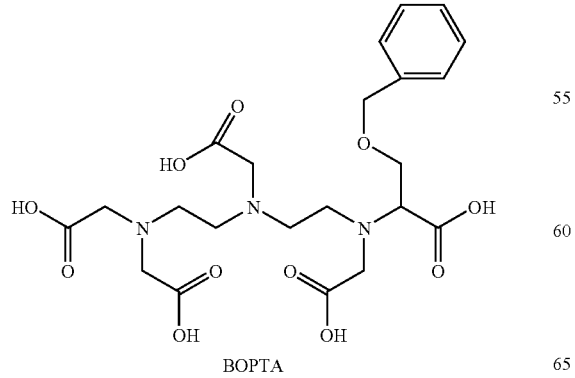

BOPTA

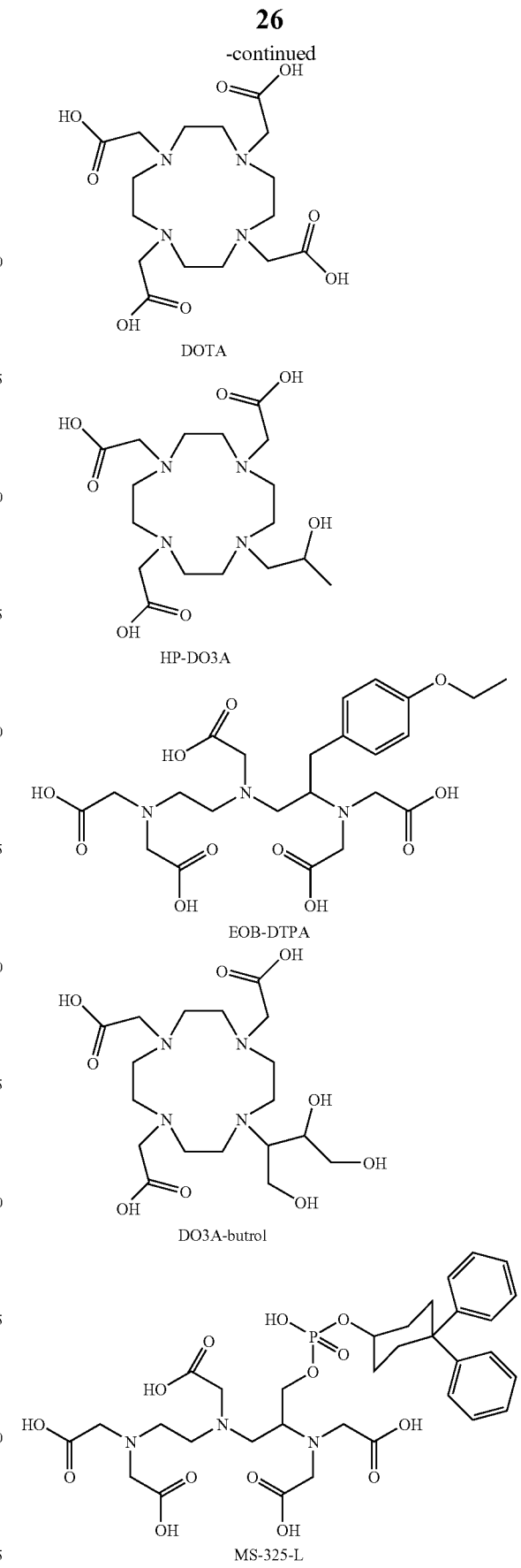

As used herein, the term "paramagnetic-metal-ion/ligand complex" is meant to refer to a coordination complex comprising one paramagnetic-metal ion (Mn+) chelated to a ligand L. Such a complex is commonly called a chelate, and hence a ligand is sometimes called a chelating agent. The paramagnetic-metal-ion/ligand complex may comprise any of the paramagnetic-metal ions or ligands discussed above and below. The paramagnetic-metal-ion/ligand complex may be designated by the following in the formulas described above and below: L-Mn+ where n is an integer that is 2 or greater The paramagnetic metal ion is suitably a multivalent ion of paramagnetic metal including but not limited to the lanthanides and transition metals such as iron, manganese, chromium, cobalt and nickel. Preferably, Mn+ is a lanthanide which is highly paramagnetic, most preferred of which is the gadolinium(III) ion having seven unpaired electrons in the 4f orbital. It is noted that the gadolinium(III) [Gd (III)] ion is often used in MR contrast agents, i.e., signal influencing or enhancing agents, because it is highly paramagnetic and has a large magnetic moment due to the seven unpaired 4f orbital electrons. In such contrast agents, gadolinium(III) ion is generally combined with a ligand (chelating agent), such as DTPA. The resulting complex [DTPA-Gd(III)] or Magnevist (Berlex Imaging, Wayne, N.J.) is very stable in vivo, and has a stability constant of 1023, making it safe for human use. Similar agents have been developed by chelating the gadolinium(III) ion with other complexes, e.g., MS-325, Epix Medical, Cambridge, Mass. The gadolinium (III) causes a lowering of T1 relaxation time of the water protons in its vicinity, giving rise to enhanced visibility in T1 weighed MR images. Because of the high signal caused by the coating by virtue of shortening of T1, the entirety of the coated devices can be readily visualized during, e.g., an endovascular procedure.

As used herein, the terms "bonded," "covalently bonded," "linked" or "covalently linked" are meant to refer to two entities being bonded, covalently bonded, linked or covalently linked, respectively, either directly or indirectly to one another.

As used herein, the term "applying" and "application" are meant to refer to application techniques that can be used to provide a coating on a medical device or substrate. Examples of these techniques include, but are not limited to, brushing, dipping, painting, spraying, overcoating, chill setting, and other viscous liquid coating methods on solid substrates.

As used herein, the term "mixing" is meant to refer to techniques that may result in homogenous or heterogeneous mixtures containing one or more components.

As used herein, the term "chain" is meant to refer to a group of one or more atoms. The chain may be a group of atoms that are part of a polymer or a strand between a pair of adjacent cross-links of a hydrogel. The chain may also be a part of a solid-base polymer, or a part of a polymer that is not covalently linked to a medical device or to hydrogel strands (e.g. a second hydrogel).

Figure 13:
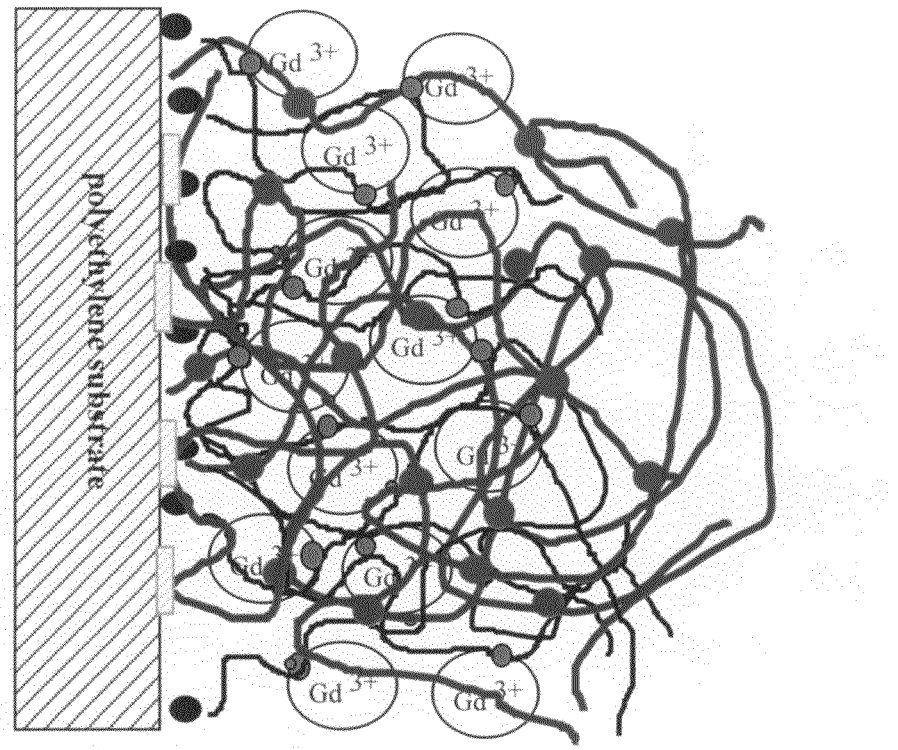
FIG. 13 is a schematic representation of one example of the second embodiment of the present invention, wherein a polyethylene rod surface coated with amine-linked polymers is chemically linked with DTPA, which is coordinated with Gd(III). The rod, polymer, DTPA and Gd(III) are encapsulated with a soluble gelatin, which is cross-linked with glutaraldehyde to form a hydrogel overcoat.
Figure 16:
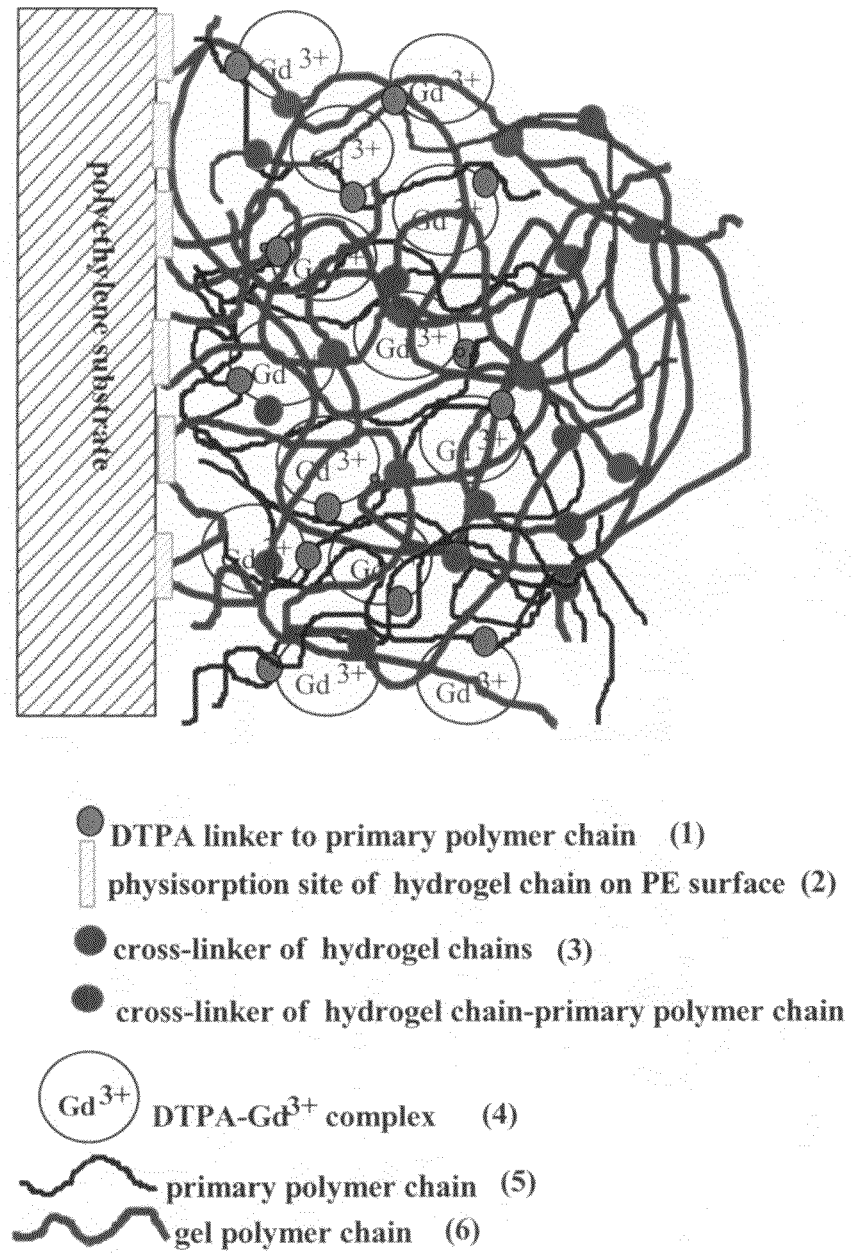
FIG. 16 is a schematic representation of one example of the third embodiment of the present invention, wherein a polymer with an amine functional group is chemically linked with DTPA, coordinated with Gd(III) and mixed with soluble gelatin. The resulting mixture is applied onto a medical device surface without prior treatment and cross-linked with glutaraldehyde to form a hydrogel overcoat. In other words.
Figure 19:
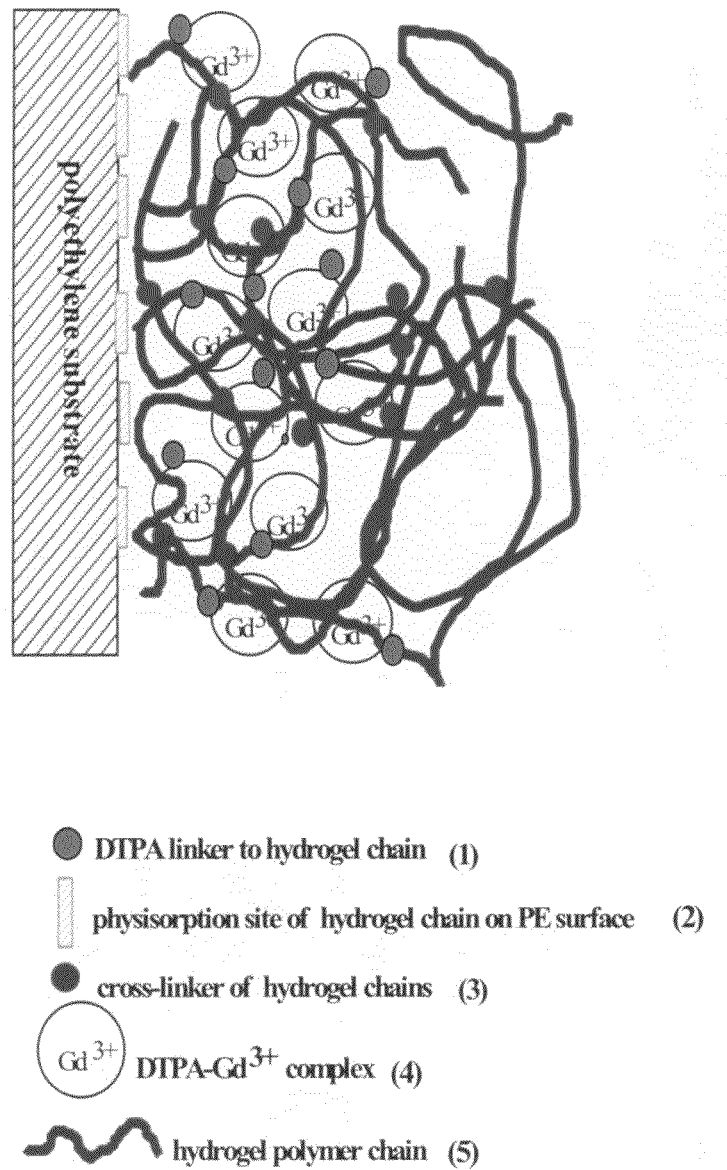
FIG. 19 is a schematic representation of one example of the fourth embodiment of the present invention, wherein gelatin is chemically linked with DTPA, which is coordinated with Gd(III) and mixed with soluble gelatin. The resulting mixture of gelatin and DTPA[Gd(III)] complex coats the surface of a medical device, and is then cross-linked with glutaraldehyde to form a hydrogel coat with DTPA[Gd(III)] dispersed therein.

As used herein, the term "encapsulated" is meant to refer to an encapsulator (e.g. a hydrogel) entangling and/or enmeshing an encapsulatee (e.g. a complex). Encapsulated implies that the encapsulatee is bonded to another entity. Examples of entities to which the encapsulatee or complex may be covalently linked include, but are not limited to, at least one of functional groups on the polymer surface of the medical device, polymers having functional groups (either covalently linked to the medical device's substrate or not covalently linked to the medical device's substrate), or hydrogels. For example, if a hydrogel encapsulates a complex, chains in the hydrogel may entangle and enmesh the complex, but the complex is also covalently linked to at least one hydrogel chain. FIGS. 13, 16 and 19 show examples of hydrogels encapsulating complexes.

Figure 23:
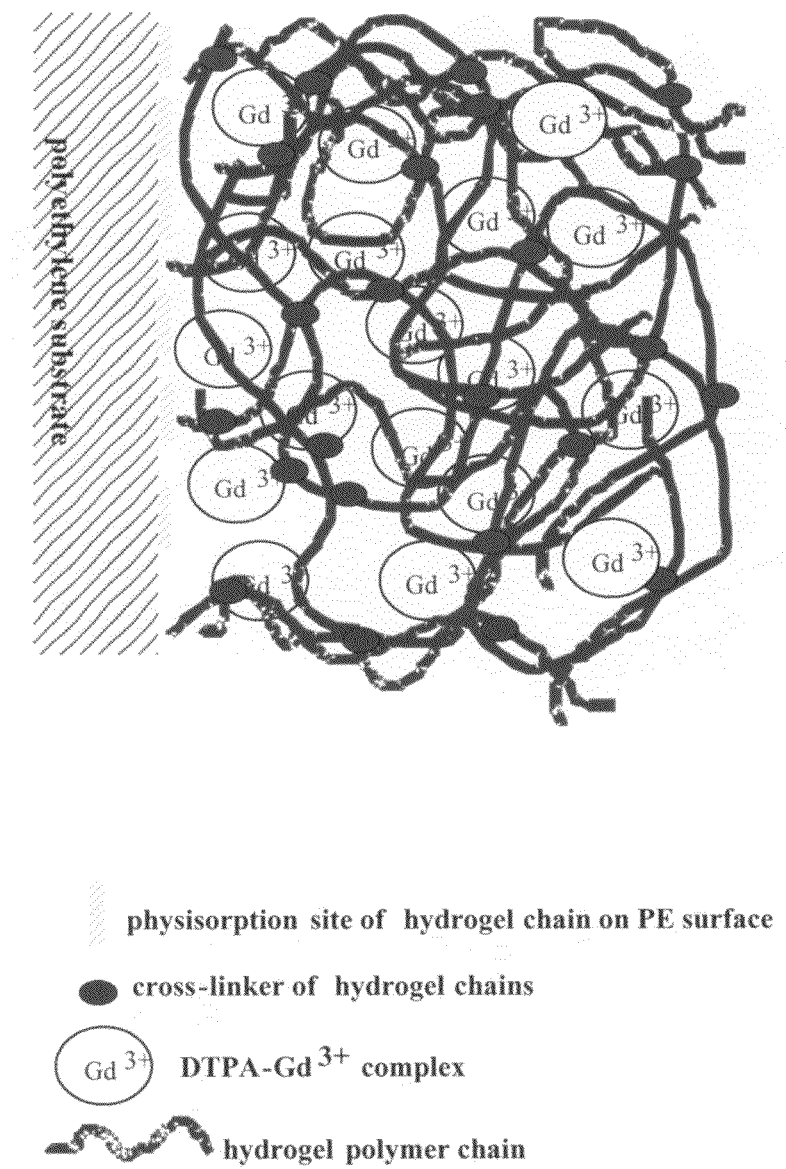
FIG. 23 is a schematic representation of one example of the fifth embodiment of the present invention, wherein DTPA[Gd(III)] complex is mixed with soluble gelatin. The resulting mixture of gelatin and DTPA[Gd(III)] complex coats the surface of a medical device and is then cross-linked with glutaraldehyde to form a hydrogel with DTPA[Gd(III)] complex stored and preserved therein. In other words.

As used herein, the term "sequestered" is meant to refer to a sequesteree (e.g. a complex) being "stored and preserved within" a sequesteror (e.g. a hydrogel). For example, if a hydrogel sequesters a complex, the hydrogel stores and preserves the complex, but the complex is not covalently linked to the hydrogel chains or any other polymer chains. The hydrogel chains may or may not be cross-linked to one another. One difference between encapsulating a complex with a hydrogel, and sequestering a complex with a hydrogel, is that the encapsulated complex is covalently linked, either directly or indirectly, to the surface of the medical device, a polymer or a hydrogel, while the sequestered complex is not covalently linked to any of these entities. FIG. 23 shows an example of a hydrogel sequestering a complex.

Some, but not all, of the additional aspects of the present invention are briefly discussed in the following paragraphs before being more fully developed in the subsequent paragraphs that follow.

A medical device of the present invention can include a body sized for use in a target object and a polymeric-paramagnetic ion complex coating in which the complex is represented by formula (I) through (VI) as set forth above and below.

In another aspect, methods are provided for visualizing medical devices in magnetic resonance imaging which includes the steps of (a) coating the medical device with a polymeric-paramagnetic complex of formula (I) through (VI) as set forth below in the detailed description; (b) positioning the device within a target object; and (c) visualizing the target object and coated device.

In a further aspect, the present invention provides several methods of making a medical device magnetic-resonance visible. The method may comprise providing a coating on the medical device in which a paramagnetic-metal ion/chelate complex is encapsulated by a first hydrogel. A chelate of the paramagnetic-metal-ion/chelate complex may be linked to a functional group, and the functional group may be an amino group or a carboxyl group. The paramagnetic-metal ion may, but need not be, designated as Mn+, wherein M is a lanthanide or a transition metal which is iron, manganese, chromium, cobalt or nickel, and n is an integer that is 2 or greater. In one embodiment, at least a portion of the medical device may be made from a solid-base polymer, and the method further comprises treating the solid-base polymer to yield the functional group thereon. Accordingly, the complex is covalently linked to the medical device. In another embodiment, the complex may be covalently linked to a functional group of a polymer that is not covalently linked to the medical device. In a different embodiment, the functional group to which the complex is linked may be a functional group of a second hydrogel. The functional group may also be a functional group of a first hydrogel or a crossed-linked hydrophilic polymer constituting a second hydrogel. The first and second hydrogels may be the same or different. A cross-linker may also be used to cross-link the first hydrogel with the solid-base polymer, the polymer not covalently linked to the medical device or the second hydrogel, depending upon the embodiment. The methods may or may not further comprise chill-setting the coating after applying the coating to the medical device. In another method, a coating comprising a paramagnetic-metal-ion/ligand complex and a hydrogel is applied to a medical device, but the complex is not covalently bonded with the hydrogel. In other words, the complex sequesters the hydrogel. A cross-linker may be used to cross-link the hydrogel chains.

In another aspect, the present invention provides several medical devices that are capable of being magnetic-resonance visualized. The device may comprise a chelate linked to a functional group. The functional group may be an amino or a carboxyl group. The device may also comprise a paramagnetic-metal ion that is coordinated with the chelate to form a paramagnetic-metal-ion/chelate complex. The device may further comprise a first hydrogel that encapsulates the paramagnetic-metal-ion/chelate complex. The paramagnetic-metal ion may, but need not be, designated as Mn+, wherein M is a lanthanide or a transition metal which is iron, manganese, chromium, cobalt or nickel, and n is an integer that is 2 or greater. In one embodiment, at least a portion of the medical device may be made from a solid-base polymer, and the functional group may be a functional group on the solid-base polymer. Accordingly, the complex is covalently linked to the medical device. In another embodiment, the functional group may be a functional group of a polymer (e.g. hydrophilic polymer) that is not covalently linked to the medical device. The functional group may be encapsulated by the hydrogel such that diffusion outward is completely blocked. In a different embodiment, the functional group may be a functional group of a second hydrogel. The second hydrogel may be well entangled with the first to form interpenetrating networks. The first and second hydrogels may be the same or different. A cross-linker may also be used to cross-link the first hydrogel with the solid-base polymer, depending upon the embodiment. In another aspect, the coating comprises a hydrogel sequestering a paramagnetic-metal-ion/ligand complex. The hydrogel is not covalently bonded with the complex. A cross-linker may also cross-link the hydrogel chains.

In yet another aspect, the present invention generally provides a method of reducing the mobility of paramagnetic metal ion/chelate complexes covalently linked to a solid polymer substrate of a medical device. This method may include providing a medical device having paramagnetic metal ion/chelate complexes covalently linked to the solid polymer substrate of the medical device. The method also includes encapsulating at least a portion of the medical device having at least one of the paramagnetic metal ion/chelate complexes covalently linked thereto with a hydrogel. The hydrogel reduces the mobility of at least one of the paramagnetic metal ion/chelate complexes, and thereby enhances the magnetic resonance visibility of the medical device. Other methods may comprise sequestering the complex using a hydrogel.

In a further aspect, the present invention generally provides a method of manufacturing a magnetic-resonance-visible medical device. The method comprises providing a medical device and cross-linking a chain with a first hydrogel to form a hydrogel overcoat on at least a portion of the medical device. The paramagnetic-metal-ion/chelate complex may be linked to the chain. The paramagnetic-metal ion may, but need not be, designated as Mn+, wherein M is a lanthanide or a transition metal which is iron, manganese, chromium, cobalt or nickel, and n is an integer that is 2 or greater. The chain may be a polymer chain (e.g. a hydrophilic polymer chain) or a hydrogel (e.g. a hydrogel strand). In one embodiment, the medical device has a surface, and the surface may be at least partially made from a solid-base polymer or coated with the polymer chain. The complex is thereby covalently linked to the medical device. In another embodiment, the complex is not linked directly to the medical device, but rather linked to the hydrogel strands. In yet another embodiment, the complex may be linked to another polymer chain, which is in turn linked to a second hydrogel. The complex may also not be linked to the device, a polymer chain or a hydrogel.

These aspects and embodiments are described in more detail below. In the following description of coating methods, coating-process steps are carried out at room temperature (RT) and atmospheric pressure unless otherwise specified.

In a first embodiment of the present invention, the MR signal-emitting coatings in accordance with the present invention are synthesized according to a three or four-step process. The three-step method includes: (i) plasma-treating the surface of a polymeric material (or a material coated with a polymer) to yield surface functional groups, e.g., using a nitrogen-containing gas or vapor such as hydrazine (NH2NH2) to yield amino groups; (ii) binding a chelating agent, e.g., DTPA, to the surface functional group (e.g. through amide linkage); and (iii) coordinating a functional paramagnetic metal ion such as Gd(III) with the chelating agent. Alternatively, the surface may be coated with amino-group-containing polymers which can then be linked to a chelating agent. Generally, the polymeric material is a solid-base polymer from which the medical device is fabricated. It is noted that the linkage between the surface functional groups and the chelates is often an amide linkage. In addition to hydrazine, other plasma gases which can be used to provide surface functional amino groups include urea, ammonia, a nitrogen-hydrogen combination or combinations of these gases. Plasma gases which provide surface functional carboxyl groups include carbon dioxide or oxygen.

The paramagnetic-metal-ion/ligand complex may be covalently bonded to the medical device such that the complex is substantially non-absorbable by a living organism upon being inserted therein. The complex is also substantially non-invasive within the endovascular system or tissues such that non-specific binding of proteins are minimized. The complex of the present invention differs substantially from other methods in which a liquid contrasting agent is merely applied to a medical device. In other words, such a liquid contrasting agent is not covalently linked to the device, and therefore, is likely to be absorbed by the tissue into which it is inserted.

A schematic reaction process of a preferred embodiment of the present invention is shown in FIG. 1. As seen specifically in FIG. 1, polyethylene is treated with a hydrazine plasma to yield surface functionalized amino groups. The amino groups are reacted with DTPA in the presence of a coupling catalyst, e.g., 1,1'-carbonyldiimidazole, to effect an amide linkage between amino groups and DTPA. The surface amino-DTPA groups are then treated with gadolinium trichloride hexahydrate in an aqueous medium, coordinating the gadolinium (III) ion with the DTPA, resulting in a complex covalently linked to the polyethylene substrate.

The MR-signal-emitting coatings are suitably made via a four-step process which is similar to the three-step process except that prior to step (ii), i.e., prior to reaction with the chelating agent, a linker agent or spacer molecule, e.g., a lactam, is bound to the surface functional groups, resulting in the coating is of formula (II).

Figure 2:
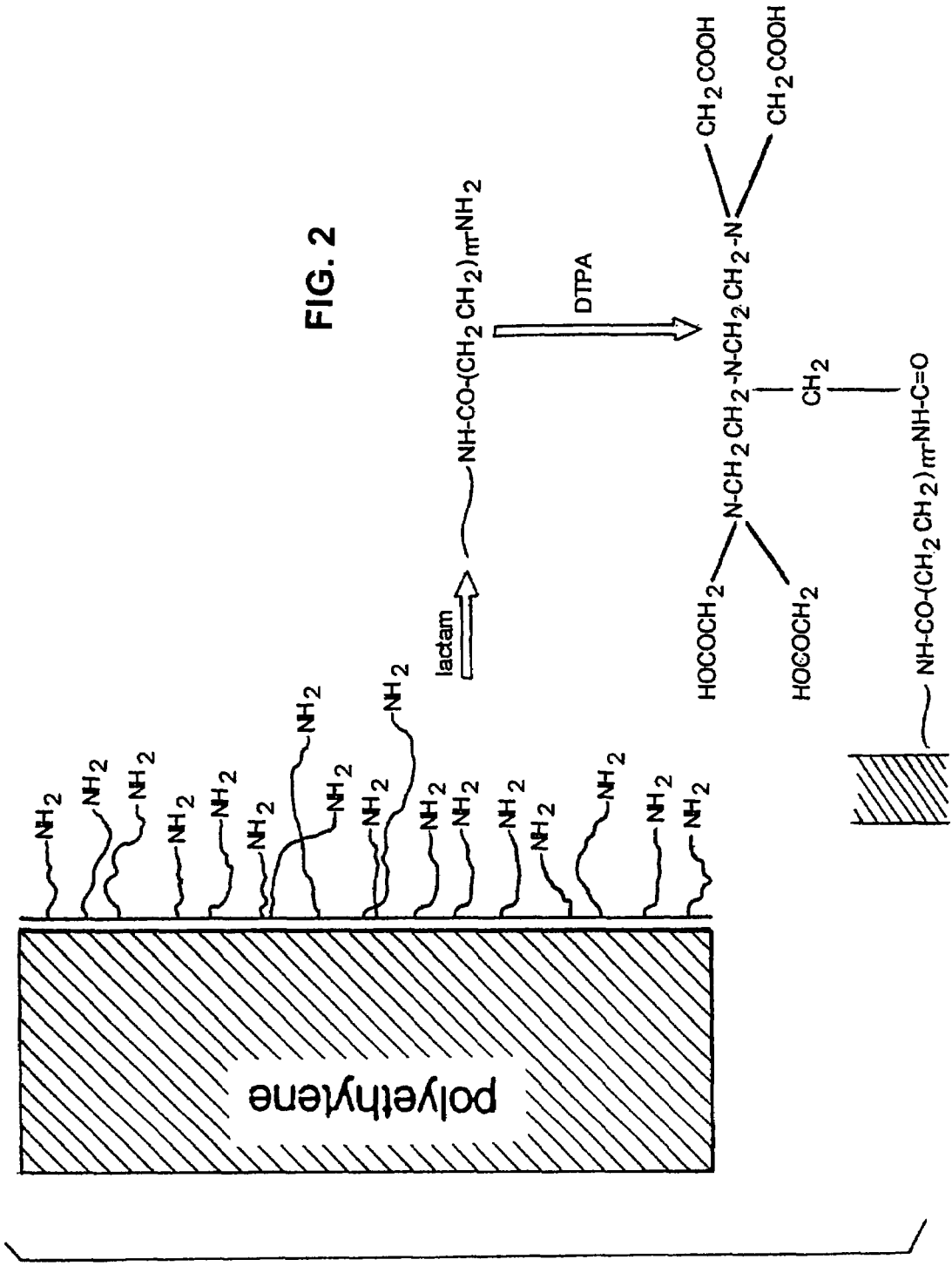
FIG. 2 is a schematic representation of the four-step coating method using a linker agent.

An illustrative schematic reaction process using a lactam or cyclic amide is shown in FIG. 2. As seen in FIG. 2, a polyethylene with an amino functionalized surface is reacted with a lactam. The amino groups and lactam molecules are coupled via an amide linkage. It is noted that "m" in the designation of the amino-lactam linkage is suitably an integer greater than 1. The polyethylene-amino-lactam complex is then reacted with DTPA which forms a second amide linkage at the distal end of the lactam molecule. The last step in the process, coordinating the gadolinium (III) ion with the DTPA (not shown in FIG. 2), is the same as shown in FIG. 1.

Specific reaction conditions for forming a coating in accordance with the present invention, which utilizes surface functionalized amino groups, include plasma treatment of a polymeric surface, e.g., a polyethylene surface, at 50 W power input in a hydrazine atmosphere within a plasma chamber, schematically represented in FIG. 3, for 5-6 min. under 13 Pa to 106 Pa (100 mT-800 mT).

As seen in FIG. 3, an exemplary plasma chamber, designated generally by reference numeral 20, includes a cylindrical stainless steel reaction chamber 22 suitably having a 20 cm diameter, a lower electrode 24, which is grounded, and an upper electrode 26, both suitably constructed of stainless steel. Electrodes 24 and 26 are suitably 0.8 cm thick. Upper electrode 26 is connected to an RF-power supply (not shown). Both electrodes are removable which facilitates post-plasma cleaning operations. Lower electrode 24 also forms part of a vacuum line 28 through a supporting conical-shaped and circularly-perforated stainless steel tubing 30 that has a control valve 31. The evacuation of chamber 22 is performed uniformly through a narrow gap (3 mm) existing between lower electrode 24 and the bottom of chamber 22. Upper electrode 26 is directly connected to a threaded end of a vacuum-tight metal/ceramic feedthrough 32 which assures both the insulation of the RF-power line from the reactor and the dissipation of the RF-power to the electrodes. A space 34 between upper electrode 26 and the upper wall of chamber 22 is occupied by three removable 1 cm thick, 20 cm diameter Pyrex™ glass disks 36. Disks 36 insulate upper electrode 26 from the stainless steel top of the reactor 20 and allow the adjustment of the electrode gap. The reactor volume located outside the perimeter of the electrodes is occupied by two Pyrex™ glass cylinders 38 provided with four symmetrically located through-holes 40 for diagnostic purposes.

This reactor configuration substantially eliminates the non-plasma zones of the gas environment and considerably reduces the radial diffusion of the plasma species, consequently leading to more uniform plasma exposure of the substrates (electrodes). As a result, uniform surface treatment and deposition processes (6-10% film thickness variation) can be achieved.

The removable top part of the reactor 20 vacuum seals chamber 22 with the aid of a copper gasket and fastening bolts 42. This part of the reactor also accommodates a narrow circular gas-mixing chamber 44 provided with a shower-type 0.5 mm diameter orifice system, and a gas- and monomer supply connection 46. This gas supply configuration assures a uniform penetration and flow of gases and vapors through the reaction zone. The entire reactor 20 is thermostated by electric heaters attached to the outside surface of chamber 22 and embedded in an aluminum sheet 48 protecting a glass-wool blanket 50 to avoid extensive loss of thermal energy.

For diagnostic purposes, four symmetrically positioned stainless steel port hole tubings 51 are connected and welded through insulating blanket 50 to the reactor wall. These port holes are provided with exchangeable, optically smooth, quartz windows 52. A vapor supply assemblage 54, as seen in FIG. 3A, includes a plasma reservoir 56, valves 58, VCR connectors 60 and connecting stainless steel tubing 62. Assemblage 54 is embedded in two 1 cm thick copper jackets 64 20 provided with controlled electric heaters to process low volatility chemicals. Assemblage 54 is insulated using a glass-wool blanket coating. The thermostatic capabilities of reactor 20 are in the range of 25-250° C.

Once the device to be coated is surface functionalized, it is then immersed in a solution of the ligand, e.g., DTPA, in, e.g., anhydrous pyridine, typically with a coupling catalyst, e.g., 1,1'-carbonyldiimidazole, for a time sufficient for the ligand to react with the amine groups, e.g., 20 hours. The surface is washed sequentially with at least one of the following solvents: pyridine, chloroform, methanol and water. The ligand-linked surface is then soaked in an aqueous solution of $GdCl3.6H2O$, for a time sufficient for the paramagnetic ion to react with the ligand, e.g., 12 hours, to form the complex, e.g., [DTPAGd(III)]. The surface is then washed with water to remove any uncoordinated, physisorbed Gd(III) ion.

In test processes, each step has been verified to confirm that the bonding and coordination, in fact, occurs. For example, to verify the amino group functionalization, x-ray photoelectron spectroscopy (XPS) was used. A XPS spectrum of the polyethylene surface was taken prior to and after plasma treatment. The XPS spectrum of polyethylene before the treatment showed no nitrogen peak. After treatment, the nitrogen peak was 5.2% relative to carbon and oxygen peaks of 63.2% and 31.6%, respectively.

To determine whether the amino groups were accessible for chemical reactions after step (i), the surface was reacted with p-trifluorobenzaldehyde or p-fluorophenone propionic acid and rinsed with a solvent (tetrahydrofuran). This reactant, chosen because of good sensitivity of fluorine atoms to XPS, produces many photoelectrons upon x-ray excitation. The result of the XPS experiment showed a significant fluorine signal. The peaks for fluorine, nitrogen, carbon and oxygen were: 3.2%, 1.5%, 75.7% and 19.6%, respectively. This demonstrated that the amino groups were accessible and capable of chemical reaction.

Because the coatings in accordance with the present invention are advantageously applied to catheters and because a catheter surface is cylindrical, it is noted that to coat commercial catheters, the plasma reaction must be carried out by rotating the catheter axis normal to the plasma sheath propagation direction. Such rotational devices are known and can be readily used in the plasma reactor depicted in FIG. 3. To verify that surface amination occurs for such surfaces, atomic force microscopy (AFM) is used to study the surface morphology because XPS requires a well-defined planar surface relative to the incident X-ray. The coating densities (e.g., nmol $Gd^{3+}/m^2$) are determined using NMR and optimal coating densities can be determined.

It is also understood that metallic surfaces can be treated with the coatings in accordance with the present invention. Metallic surfaces, e.g., guide-wires, can be coated with the polymers set forth above, e.g., polyethylene, by various known surface-coating techniques, e.g., melt coating, a well known procedure to overcoat polymers on metal surfaces. Once the metallic surfaces are overcoated with polymer, all other chemical steps as described herein apply. In an example to be described below, we used commercial guide-wires that were previously coated with hydrophilic polymers.

In a second embodiment of the present invention, the magnetic resonance visibility of medical devices is enhanced or improved by encapsulating the medical device, or paramagnetic-metal-ion/chelate complexes linked thereto, with a hydrogel. As discussed above, catheters and other medical devices may be at least partially made or coated with a variety of polymers. The polymer surfaces of the existing medical devices are functionalized by plasma treatment or by melt coating with a hydrophilic polymer as discussed above or precoating with a hydrophilic polymer containing primary amine groups. Through amide linkage or α,ω-diamide linkage via a linker molecule, a ligand may be covalently bonded to the functionalized polymer surface through amide linkage. Subsequently, any of the paramagnetic-metal ions discussed above, e.g. Gd(III), can be complexed to the ligand. The necessary contrast for MRI is the result of interactions of water protons in body fluid (e.g., blood) or bound within the encapsulating hydrogel with the highly magnetic ion, causing shortening of T1 relaxation time of the proton. It has been discovered that the MR-visibility of the medical device is enhanced and improved by reducing the mobility of the paramagnetic-metal-ion/ligand complex without affecting the exchange rate of the inner sphere water that coordinates with the paramagnetic metal ion with the outer sphere water that is free in the bulk. In other words, if the movement of these complexes is restricted, the MR-visibility of a device with the complex covalently linked thereto is greatly improved.

Therefore, it has been found that one way to reduce the mobility of the complex for visualizing is to encapsulate or sequester the complex with a polymeric network, and more particularly, with a hydrogel. Encapsulating is discussed with respect to embodiments 2-4, while sequestering is discussed in more detail with respect to embodiment 5. The hydrogel reduces the mobility, and more particularly, rotational mobility of the paramagnetic-metal-ion/ligand complexes without significantly affecting the exchange rate of the inner sphere water molecule and those of the outer sphere, thereby enhancing the magnetic-resonance visibility of the medical devices. The mobility may be reduced without affecting one molecule of water that participates in coordination. The water molecule on the coordination sphere of paramagnetic metal is often referred to as the inner sphere waters. There is a delicate balance between slowing of the rotational relaxation time of the paramagnetic-metal-ion/ligand complexes and retardation of the exchange rate of the inner sphere and outer sphere water molecules. The reason for MR visibility for free paramagnetic-metal-ion/ligand complexes without being bonded to polymer surface comes about because of a much greater concentration of the complex in solution compared with that bound to the surface. Thus, hydrogel encapsulation arises from the inherently low concentration of the complex on the surface.

Examples of suitable hydrogels include, but are not limited to, at least one of collagen, gelatin, hyaluronate, fibrin, alginate, agarose, chitosan, poly(acrylic acid), poly(acrylamide), poly(2-hydroxyethyl methacrylate), poly(N-isopropylacrylamide), poly(aminoalkylmethacylamide), poly(ethylene glycol)/poly(ethylene oxide), poly(ethylene oxide)-block-poly(lactic acid), poly(vinyl alcohol), polyphosphazenes, polypeptides and combinations thereof. Any hydrogel or similar substance which reduces the mobility of the paramagnetic-metal-ion/ligand complex can also be used, such as physical hydrogels that can be chill-set without chemical cross-linking. In addition, overcoating of high molecular weight, hydrophilic polymers can be used, e.g., poly(acrylic acid), poly(vinyl alcohol), polyacrylamide, having a small fraction of functional groups that can be linked to residual amino groups, are suitable for use with the present invention. The MR-visibility of other MR-visible devices made by methods other than those described herein may also be improved by coating such devices with the hydrogels described above.

The devices can be encapsulated using a variety of known encapsulating techniques in the art. For example, a gel may be melted into a solution, and then the device dipped into the solution and then removed. More particularly, the gel may be dissolved in distilled water and heated. Subsequently, the solution coating the device is allowed to dry and physically self assemble to small crystallites therein that may adsorb to the polymer surface of the medical device and at the same time play the role of cross-links. Such a phenomenon is commonly referred to as "chill-set" since it arises from thermal behavior of gelling systems indicated in the above.

The gel may also be painted onto the medical device. Alternatively, the medical device may be encapsulated by polymerization of a hydrophilic monomer with a small fraction of cross-linker that participates in the polymerization process. For example, a medical device may be immersed in a solution of acrylamide monomer with bisacrylamide as the cross-linker and a photo-initiator, and the polymerization is effected with ultra-violet (UV) irradiation to initiate the polymerization in a cylindrical optical cell.

Alternatively, the medical device may be dipped into a gelatin solution in a suitable concentration (e.g., 5%), and mixed with a cross-linker such as glutaraldehyde. As used herein, the term "cross-linker" is meant to refer to any multi-functional chemical moiety which can connect two or a greater number of polymer chains to produce a polymeric network. Other suitable cross-linkers include, but are in no way limited to, BVSM (bis-vinylsulfonemethane), BVSME (bis-vinylsulfonemethane ether), and glutaraldehyde. Any substance that is capable of cross-linking with the hydrogels listed above is also suitable for use with the present invention. Upon removing the device from the gelatin solution and letting it dry, the cross-linking takes place to encapsulate the entire coated assembly firmly with a sufficient modulus to be mechanically stable.

Encapsulation may be repeated until the desired thickness of the gel is obtained. The thickness of the encapsulated-hydrogel layer may be greater than about 10 microns. Generally, the thickness is less than to about 60 microns for the mechanical stability of the encapsulating hydrogel upon reswelling in the use environment. In other words, the surface may be "primed" and then subsequently "painted" with a series of "coats" of gel until the desired thickness of the gel layer is obtained. Alternatively, the gel concentration is adjusted to bring about the desired thickness in a single coating process. In order to test the effectiveness of coating these devices with hydrogels to enhance the MR-visibility of the medical device, three samples were prepared and tested as set forth and fully described in Example 10 below.

These same techniques may be used to sequester the complex, except, as stated above, sequestering implies that the complex is not covalently bonded to another functional group, polymer chain, functional group of a polymer or a hydrogel. Again, sequestering is discussed in more detail with respect to the fifth embodiment.

Example 11 below also describes in more detail how one example of the second embodiment of the present invention can be made. Moreover, FIG. 13 is a schematic representation of one example of the second embodiment of the present invention, wherein a polyethylene rod, surface coated with polymers with pendant amine groups, is chemically linked with DTPA, which is coordinated with Gd(III). The rod, polymer, DTPA and Gd(III) are encapsulated with a soluble gelatin, which is cross-linked with glutaraldehyde to form a hydrogel overcoat. FIG. 14 shows the chemical details for the example schematically represented in FIG. 13.

The second embodiment of MR-visible coatings may be summarized as a coating for improving the magnetic-resonance visibility of a medical device comprising a complex of formula (III). The method includes encapsulating at least a portion of the device having a paramagnetic-metal-ion/ligand complex covalently linked thereto with a hydrogel. The complex of formula (III) follows:

(P—X-L-Mn+)gel     (III), wherein P is a base polymer substrate from which the device is made or with which the device is coated; X is a surface functional group; L is a ligand; M is a paramagnetic ion; n is an integer that is 2 or greater; and subscript "gel" stands for a hydrogel encapsulate.

In a third embodiment of the present invention, a polymer having functional groups is chemically linked with one or more of the ligands described above. More particularly, the polymer having a functional group (e.g. an amino or a carboxyl group) is chemically linked to the chelate via the functional group. In addition to the polymers set forth above, an example of a suitable polymer having functional groups is, but should not be limited to, poly(N[3-aminopropyl]methacrylamide).

The third embodiment alleviates the need for a precoated polymer material on the medical device, or a medical device made from a polymer material. In other words, the third embodiment alleviates the need to link the paramagnetic-metal-ion/ligand complex to the surface of the medical device, when the medical device is made from or coated with a polymer. Instead, the carrier polymer having functional groups, e.g., amine, can be synthesized separately and then covalently linked to the ligand (e.g. DTPA) through the functional groups (e.g. amine groups) on the polymer. Instead of linking the complex to the surface of the medical device, the polymer linked with the ligand is added to a hydrogel. Thus, the polymer with the functional groups is called a carrier polymer. The ligand may be coordinated with the paramagnetic-metal ion (e.g. Gd(III)), and then mixed with soluble gelatin, and the binary mixture is used to coat a bare (i.e. uncoated) polyethylene rod. Subsequently, the gelatin is chill-set and then the binary matrix of gelatin and polymer may then be cross-linked with a cross-linker such as glutaraldehyde. The carrier polymer used in connection with this embodiment may be a poly(N[3-aminopropyl]methacrylamide), the ligand may be DTPA and the paramagnetic-metal ion may be Gd(III). In addition, the hydrogel may be gelatin and the cross-linker may be glutaraldehyde. Typically, the surface of the medical device may be polyethylene. Again, in addition to these specific compounds, any of the polymers, ligands, paramagnetic-metal ions, hydrogels and cross-linkers discussed above are also suitable for use with this embodiment of the present invention.

Example 12 below describes in more detail how one example of the third embodiment of the present invention can be made. FIG. 16 is a schematic representation of one example of the third embodiment of the present invention, wherein a polymer is chemically linked with DTPA, coordinated with Gd(III) and mixed with soluble gelatin. The resulting mixture is applied to a bare (i.e. uncoated) polyethylene surface and cross-linked with glutaraldehyde to form a hydrogel overcoat. FIG. 17 shows the chemical details for the example schematically represented in FIG. 16.

The third embodiment may be summarized as a coating for visualizing medical devices in magnetic resonance imaging comprising a complex of formula (IV). The method includes encapsulating a complex, and therefore at least a portion of the medical device, with a hydrogel, wherein one of the paramagnetic-metal-ion/ligand complexes covalently linked to a polymer is dispersed in the hydrogel. The complex of formula (IV) follows:

(S ... P'—X-L-Mn+)gel       (IV)

wherein S is a medical device substrate not having functional groups on its surface; P' is a carrier polymer with functional groups X which is not being linked to the surface of the medical device; L is a ligand; M is a paramagnetic ion; n is an integer that is 2 or greater; and subscript "gel" stands for a hydrogel encapsulate.

In a fourth embodiment of the present invention, a hydrogel having functional groups can be used instead of a carrier polymer. For example, gelatin may be used instead of the carrier polymers discussed above. Accordingly, the gelatin or hydrogel rather than the carrier polymer may be covalently linked with a ligand. The gelatin, e.g., may be covalently linked to a ligand such as DTPA through the lysine residues of gelatin. In addition, hydrogels that are modified to have amine groups in the pendant chains can be used instead of the carrier polymer, and can be linked to ligands using amine groups. The ligand is coordinated with a paramagnetic-metal ion such as Gd(III) as described above with respect to the other embodiments to form a paramagnetic-metal ion/ligand complex, and then mixed with a soluble hydrogel such as gelatin. The soluble hydrogel may be the same or may be different from the hydrogel to which the paramagnetic-metal ion/chelate complex is linked. The resulting mixture is used to coat a substrate or, e.g., a bare polyethylene rod. More particularly, the mixture is used to coat a medical device using the coating techniques described above with respect to the second embodiment. The coated substrate or medical device may then be chill-set. Subsequently, the hydrogel matrix or, for example, the gelatin-gelatin matrix may then be cross-linked with a cross-linker such as glutaraldehyde. The cross-linking results in a hydrogel overcoat, and a substance which is MR-visible.

Example 13 below describes in more detail how one example of the fourth embodiment of the present invention can be made. FIG. 19 is a schematic representation of one example of the fourth embodiment of the present invention, wherein gelatin is chemically linked with DTPA, which is coordinated with Gd(III), and mixed with free soluble gelatin without any DTPA linked. The resulting mixture of gelatin and DTPA[Gd(III)] complex coats a bare polyethylene surface, and is then cross-linked with glutaraldehyde to form a stable hydrogel coat with DTPA[Gd(III)] dispersed therein. FIG. 20 shows the chemical details for the example schematically represented in FIG. 19.

The fourth embodiment can be summarized as a coating for visualizing medical devices in magnetic resonance imaging comprising a complex of formula (V). The method includes encapsulating at least a portion of the medical device with a hydrogel, wherein the hydrogel is covalently linked with at least one of the paramagnetic-metal-ion/ligand complexes. The complex of formula (V) follows:

(S ... G-X-L-Mn+)gel       (V)

wherein S is a medical device substrate which is made of any material and does not having any functional groups on its surface; G is a hydrogel polymer with functional groups X that can also form a hydrogel encapsulate; L is a ligand; M is a paramagnetic ion; n is an integer that is 2 or greater; and subscript "gel" stands for a hydrogel encapsulate.

In a fifth embodiment of the present invention, the need to covalently link the hydrogel to the paramagnetic-metal-ion/ligand complex may be obviated. In the fifth embodiment, a ligand (such as DTPA) is coordinated with a paramagnetic-metal ion (such as Gd(III)) to form a paramagnetic-metal ion/ligand complex as set forth above with respect to the other embodiments. The paramagnetic-metal-ion/ligand complexes are then mixed with at least one of the hydrogels (e.g. gelatin) discussed above to form a mixture for coating. A cross-linker (such as bis-vinyl sulfonyl methane (BSVM) or one or more of the other cross-linkers set forth above) may or may not be added, to this mixture. Subsequently, the resultant mixture or coating formulation is applied to a medical device or other substrate which is meant to be made MR-visible. In other words, for the fifth embodiment, the hydrogel sequesters the complex that is not covalently bonded to the hydrogel. Any of the application methods discussed above may be used to apply the resultant mixture to the device or substrate. After application of the mixture to the device or substrate, the device or substrate may or may not be allowed to chill-set and dry. When utilizing a cross-linker, the cross-linker will cross-link the hydrogel during and after the chill-set period. The device or substrate may or may not then be rinsed or soaked in distilled water in order to remove paramagnetic-metal ion/ligand complexes that were not physically or chemically constrained by the hydrogel or cross-linked hydrogel network.

Alternatively, as set forth in Example 15, a ligand and a hydrogel may be mixed, and then applied to a substrate or medical device. The applied coating may or may not be cross-linked using a cross-linker. Subsequently, a paramagnetic metal ion may be coordinated to the ligand. The device may or may not then be rinsed or soaked in distilled water, depending on excess cross-linkers to be removed.

Any of the hydrogels, paramagnetic metal ions, ligands and cross-linkers discussed herein may be used in conjunction with the fifth embodiment. More than one overcoat may be used. The overall thickness of the overcoat is generally greater than about 10 microns. The thickness is generally less than to about 60 microns to ensure the mechanical stability of reswollen hydrogels.

Examples 14 and 15 below describe in more detail how several examples of the fifth embodiment of the present invention can be made. FIGS. 23-30 also relate to the fifth embodiment and are discussed in more detail above.

The fifth embodiment may be summarized as a coating for visualizing medical devices and substrates in magnetic imaging comprising a complex of formula (VI). The method includes coating a portion of the medical device with a hydrogel that sequesters one or more paramagnetic-metal ion/ligand complexes. The complex of formula (VI) follows:

(S . . . L-Mn+)gel    (VI)

wherein S is a medical device or substrate; L is a ligand; M is a paramagnetic ion; n is an integer that is 2 or greater; and subscript "gel" stands for a hydrogel. The complex is not covalently bonded to a hydrogel, a polymer or the substrate.

The present invention is further explained by the following examples which should not be construed by way of limiting the scope of the present invention. A description of the preparation and evaluation of MR-visible PE polymer rods follows.

A multi-mode medical device system of the present invention integrates forward-looking capability, and at least one of tracking, imaging, and visualizing and combinations thereof in a medical device as described above and in the Examples below. The multi-mode medical device systems that incorporate the forward-looking capability retain some or all of the features and operability as the multi-mode medical device systems described above and in the Examples below.

FIG. 56 illustrates one embodiment of a multi-mode medical device system 500 according to the present invention. More specifically, FIG. 56 illustrates a multi-mode medical device system with tracking, imaging, and forward-looking capabilities. The multi-mode medical device system 500 illustrated in FIG. 56 includes a medical device 502 including an electrical circuit 504 coupled to the medical device 502. The electrical circuit 504 includes an integrated tracking device 506 (e.g., a Helmholtz pair) and an imaging/visualizing device 508 (e.g., an imaging loop). The multi-mode medical device system 500 is described in U.S. patent application Ser. No. 11/728,873 titled "System and Method of Performing Therapeutic Endovascular Interventions" filed on an even date herewith, the entire disclosure of which is incorporated herein by reference.

The multi-mode medical device system 500 further includes a voltage standing wave suppression device 550. Voltage standing waves may form on the exterior surface 512 of the medical device 502 as a length L of the medical device 502 approaches a wavelength WL of the imaging signal. The voltage standing waves can generate a common mode signal on the outer surface 512 of the medical device 502. These common mode signals can cause undesired tissue heating in localized regions surrounding the exterior surface 512 of the medical device 502. The voltage standing wave suppression device 550 serves to reduce or prevent the formation of voltage standing waves, thereby reducing common mode signals on the exterior surface 512 of the medical device 502 and reducing localized tissue heating.

The voltage standing wave suppression device 550 includes a proximal cable trap 552 located near the proximal end of the medical device 502 and a distal cable trap 554 located near the distal end of the medical device 502. The proximal and distal cable traps 552, 554 are each formed of small regions of tightly packed coils of a conductive member 556 extending from the distal end of the medical device 502 to the proximal end of the medical device 502. The cable traps 552, 554 can be formed on the exterior surface 512 of the medical device 502. The conductive member 556 is connected in series with the tracking device 506 and/or the imaging/visualization device 508. In the illustrated embodiment, the cable traps 552, 554 are formed in the imaging loop of the imaging/visualization device 508. In other embodiments, however, the imaging loop may be excluded such that the conductive member 556 is merely a conductor connected in series with the tracking device 506.

The cable traps 552, 554 present a high impedance to common mode signals generated on the exterior surface 512 of the medical device 502. This phenomena is accomplished by each cable trap creating a balun for broadband blocking over a very short length of the medical device 502 where the turns of the cable trap are located. The cable traps 552, 554 present a low impedance, however, to differential mode signals induced in the conductive member (i.e., the imaging signal). The cable traps 552, 554 therefore suppress the formation of common mode voltage standing waves without interfering with the transmission of the differential mode imaging signal through the medical device 502.

A distance between the cable traps 552, 554 is selected to prevent the formation of voltage standing waves. The cable traps 552, 554 effectively "shorten" the length of the imaging device 502 into segments (i.e., from the distal end of the medical device 502 to the distal cable trap 554, between the cable traps 552, 554, and from the proximal cable trap 552 to the proximal end of the medical device 502) such that the length of each segment is significantly shorter than the wavelength WL of the imaging signal. This prevents the formation of voltage standing waves at high potential nodes along the medical device 502.

In one embodiment, a distance D between the cable traps 552, 554 is approximately one half the length L of the medical device 502. Thus, the spacing between the proximal and distal cable traps 552, 554 can vary depending upon the length L of the medical device 502. In another embodiment, the distance D between the cable traps 552, 554 is from about one tenth to about one fifth of the wavelength WL of the imaging signal. Thus, the spacing between the proximal and distal cable traps 552, 554 can vary depending upon the wavelength WL, and thus frequency F, of the imaging signal. The imaging signal wavelength WL and frequency F can vary depending upon the magnetic field generated by the imaging device (i.e., 1.5 T-3 T).

FIG. 57 shows another embodiment of the voltage standing wave suppression device 550 including additional cable traps. In the illustrated embodiment, the voltage wave suppression device 550 include an intermediate cable trap 558 located evenly spaced between the proximal cable trap 552 and the distal cable trap 554. The cable traps 552, 554 and 558 are spaced apart by a distance D1 and D2. The voltage standing wave suppression device 550 can include additional cable traps, such as, for example, four, five or six cable traps.

Each cable trap 552, 554 is formed of tightly packed coils of the conductive member 556. In one embodiment, each cable trap 552, 554 can be formed of from about 60 to about 90 coil turns. In another embodiment, each cable trap 552, 554 can be formed of from about 70 to about 75 coil turns. In one embodiment, each cable trap 552, 554 can be formed of from about 60, about 65, about 70, about 75 cable turns. In another embodiment, each cable trap 552, 554 can be formed from less than 90 cable turns. Because each cable trap 552, 554, is relatively short in length compared to the length L of the medical device 502, the voltage standing wave suppression device 550 has a reduced impact on the mechanical properties of the medical device 502, including, for example, at least one of flexibility, stiffness, bending radius and torquability. The medical device 502 therefore retains those mechanical properties as desired for facilitating insertion of the medical device 502 into the patient's body and maneuvering the distal end of the medical device 502 to desired locations for imaging and for performing intervention procedures.

It should be appreciated that the voltage standing wave suppression device 550 is capable of being used with a variety of implantable medical devices and is not limited to use with the multi-mode medical device system 500 as illustrated in FIGS. 56 and 57. In general, any implantable medical device that has a co-axial construction may be susceptible to the formation of voltage standing waves during an MR procedure. While such implantable medical device may not necessarily transmit a differential mode signal, the formation of voltage standing waves can still cause undesired localized heating of the tissue near the device. Therefore, in other embodiments, the voltage standing wave suppression device 550 is incorporated into any other implantable medical device susceptible to the formation of voltage standing waves. This can include, for example, implantable medical devices such as catheters, guidewires, and endovascular delivery devices for balloons, stents and/or coils, etc. or any other device adapted to be used within an external field as would be generated by an MR device during an interventional procedure. The distance D between the cable traps 552, 554 may be approximately one half the length L of the medical device 502. In another embodiment, the distance D between the cable traps 552, 554 can vary depending upon the magnetic field generated by the imaging device (i.e., 1.5 T-7 T).

Examples 1-20 below further illustrate various embodiments of MR-visible/imageable coatings, medical devices including MR-visible coatings applied thereto, and methods for manufacturing such medical devices.

EXAMPLES

Example 1

Preparation of Coated Polyethylene Sheets

Polyethylene sheets were coated in the three-step process referred in the above and described herein in detail.

Surface Amination. A polyethylene sheet (4.5 in diameter and 1 mil thick) was placed in a capacitively coupled, 50 kHz, stainless steel plasma reactor (as shown schematically in FIGS. 3 and 3A) and hydrazine plasma treatment of the polyethylene film was performed. The substrate film was placed on the lower electrode. First, the base pressure was established in the reactor. Then, the hydrazine pressure was slowly raised by opening the valve to the liquid hydrazine reservoir. The following plasma conditions were used: base pressure=60 mT; treatment hydrazine pressure=350 mT; RF Power=25 W; treatment time=5 min; source temperature (hydrazine reservoir)=60° C.; temperature of substrate=40° C. Surface atomic composition of untreated and plasma-treated surfaces were evaluated using XPS (Perkin-Elmer Phi-5400; 300 W power; Mg source; 15 kV; 45° takeoff angle).

DTPA Coating. In a 25 mL dry flask, 21.5 mg of DTPA was added to 8 mL of anhydrous pyridine. In a small vessel, 8.9 mg of 1,1'-carbonyldiimidazole (CDI), as a coupling catalyst, was dissolved in 2 mL of anhydrous pyridine. The CDI solution was slowly added into the reaction flask while stirring, and the mixture was further stirred at room temperature for 2 hours. The solution was then poured into a dry Petri dish, and the hydrazine-plasma treated polyethylene film was immersed in the solution. The Petri dish was sealed in a desiccator after being purged with dry argon for 10 min. After reaction for 20 hours, the polyethylene film was carefully washed in sequence with pyridine, chloroform, methanol and water. The surface was checked with XPS, and the results showed the presence of carboxyl groups, which demonstrate the presence of DTPA.

Gadolinium (III) Coordination. 0.70 g of GdCl3.6H2O was dissolved in 100 mL of water. The DTPA-treated polyethylene film was soaked in the solution for 12 hr. The film was then removed from the solution and washed with water. The surface was checked with XPS, showing two peaks at a binding energy (BE)=153.4 eV and BE=148.0 eV, corresponding to chelated Gd3+ and free Gd3+, respectively. The film was repeatedly washed with water until the free Gd3+ peak at 148.0 eV disappeared from the XPS spectrum.

The results of the treatment in terms of relative surface atomic composition are given below in Table 1.

TABLE 1

Relative Surface Atomic Composition of untreated and treated PE surfaces

|  | % Gd | % N | % O | % C |
| --- | --- | --- | --- | --- |
| Untreated PE | 0.0 | 0.0 | 2.6 | 97.4 |
| Hydrazine plasma treated PE | 0.0 | 15.3 | 14.5 | 70.2 |
| DTPA linked PE substrate | 0.0 | 5.0 | 37.8 | 57.2 |
| Gd coordinated PE substrate | 1.1 | 3.7 | 35.0 | 60.3 |

Example 2

Preparation of Coated Polyethylene Sheets Including a Linker Agent

Coated polyethylene sheets were prepared according to the method of Example 1, except that after surface amination, the polyethylene sheet was reacted with a lactam, and the sheet washed before proceeding to the coordination (chelation) step. The surface of the film was checked for amine groups using XPS.

Example 3

Visualizing of Coated Polyethylene and Polypropylene Sheets

Figure 4:
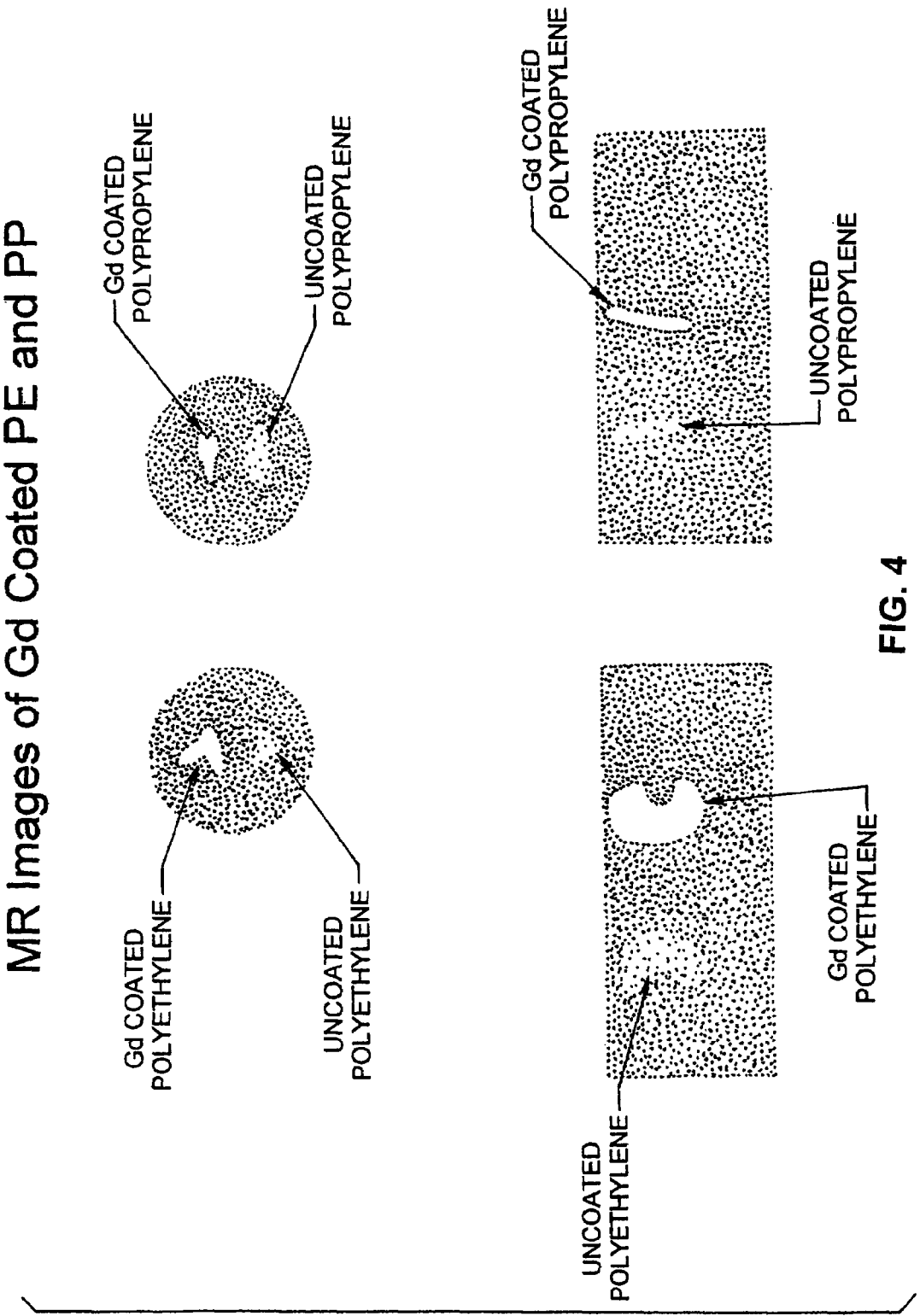
FIG. 4 is several MR images of coated devices in accordance with the present invention.

MR signal enhancement was assessed by visualizing coated sheets of polyethylene and polypropylene, prepared as described in Example 1, with gradient-recalled echo (GRE) and spin-echo (SE) techniques on a clinical 1.5 T scanner. The sheets were held stationary in a beaker filled with a tissue-mimic, fat-free food-grade yogurt, and the contrast-enhancement of the coating was calculated by normalizing the signal near the sheet by the yogurt signal. The T1-weighed GRE and SE MR images showed signal enhancement near the coated polymer sheet. The T1 estimates near the coated surface and in the yogurt were 0.4 s and 1.1 s, respectively. No enhancement was observed near the control sheet without the coating. The MR images acquired are shown in FIG. 4.

Example 4

In Vitro Testing of DTPA[Gd(III)] Filled Catheter Visualization

The following examples demonstrated the utility of DTPA [Gd(III)] in visualizing a catheter under MR guidance.

A DTPA[Gd(III)] filled single lumen catheter 3-6 French (1-2 mm) was visualized in an acrylic phantom using a conventional MR Scanner (1.5T Signa, General Electric Medical Systems) while it was moved manually by discrete intervals over a predetermined distance in either the readout direction or the phase encoding direction. The phantom consisted of a block of acrylic into which a series of channels had been drilled. The setup permitted determination of the tip position of the catheter with an accuracy of ±1 mm (root-mean-square). Snapshots of the catheter are shown in FIG. 5.

Example 5

In Vivo Testing of DTPA[Gd(III)] Filled Catheter Visualization

Figure 6:
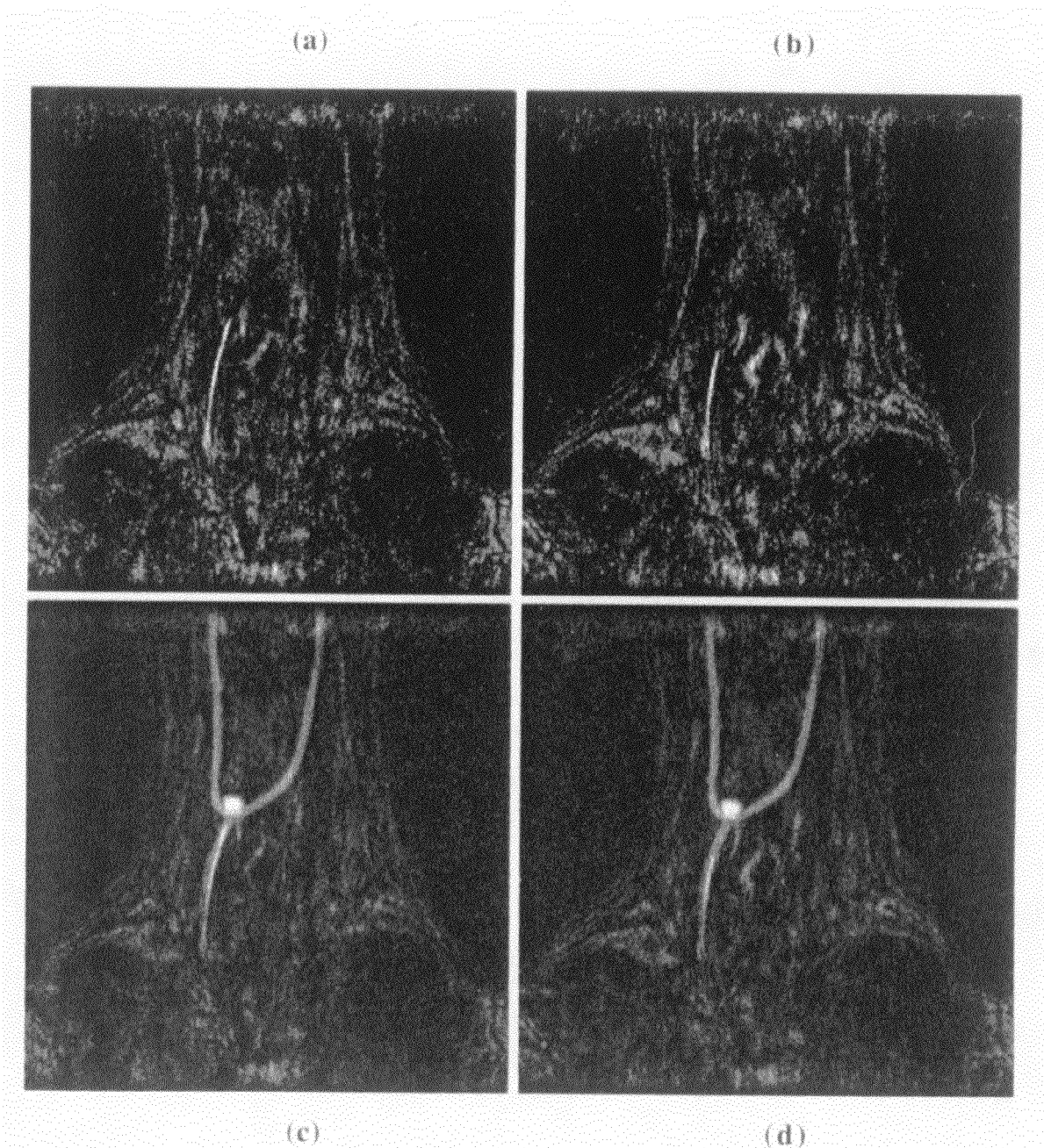
FIG. 6 is temporal MR snapshots of a Gd-DTPA-filled catheter moving in the common carotid of a canine.
Figure 7:
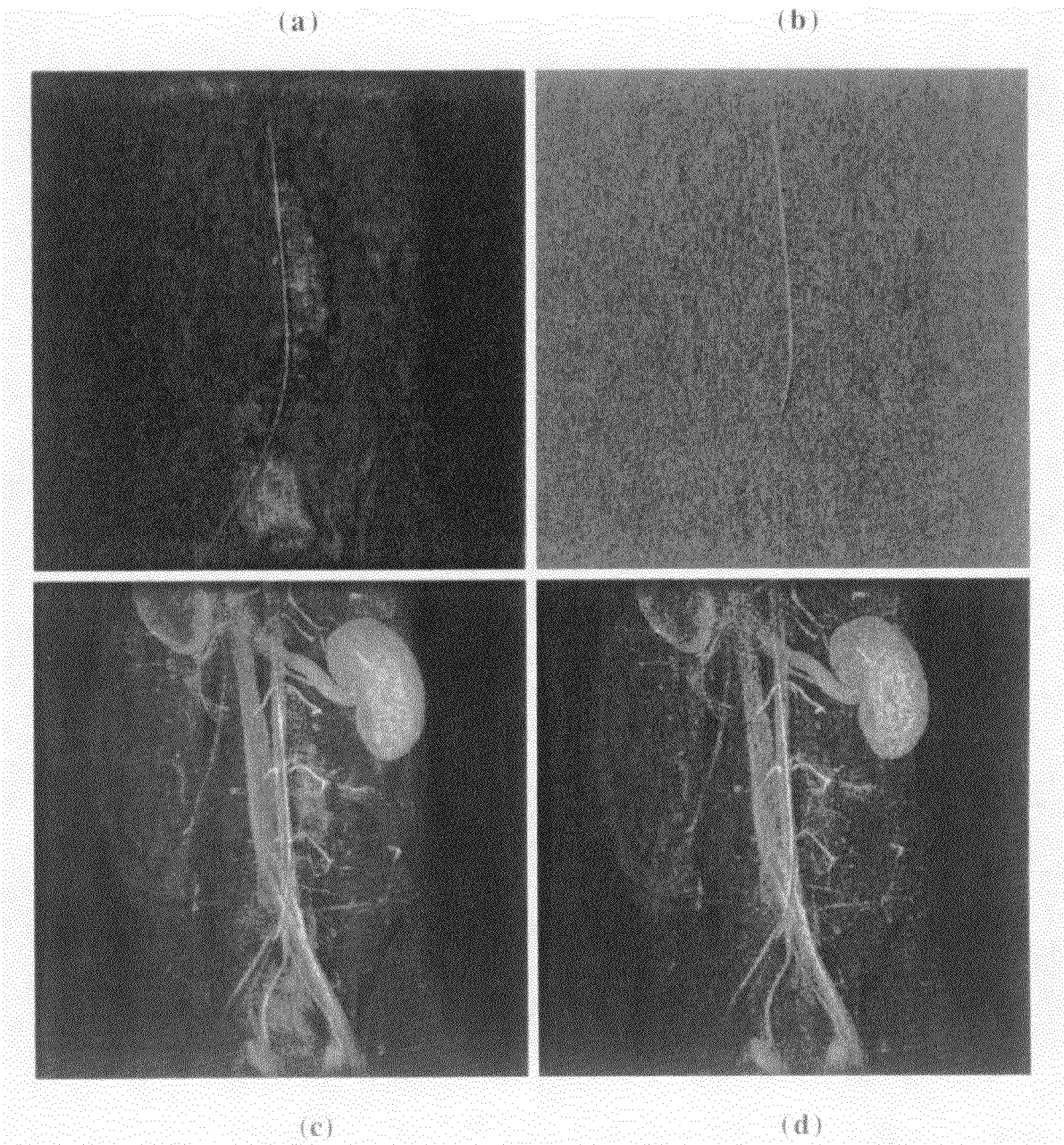
FIG. 7 is temporal MR snapshots of a Gd-DTPA-filled catheter in a canine aorta.

For in vivo evaluation, commercially-available single lumen catheters filled with DTPA[Gd(III)] (4-6% solution), ranging in size between 3 and 6 French (1-2 mm), and catheter/guide-wire combinations were visualized either in the aorta or in the carotid artery of four canines. All animal experiments were conducted in conjunction with institution-approved protocols and were carried out with the animals under general anesthesia. The lumen of the catheter is open at one end and closed at the other end by a stopcock. This keeps the DTPA[Gd(III)] solution in the catheter lumen. The possibility of DTPA[Gd(III)] leaking out of the catheter lumen through the open end was small and is considered safe because the DTPA[Gd(III)] used in these experiments is commercially available and approved for use in MR. Reconstructed images made during catheter tracking were superimposed on previously acquired angiographic "roadmap" images typically acquired using a 3D TRICKS imaging sequence (F. R. Korosec, R. Frayne, T. M. Grist, C. A. Mistretta, Magn. Reson. Medicine. 1996, 36 345-351, incorporated herein by reference) in conjunction with either an intravenous or intra-arterial injection of DTPA[Gd(III)] (0.1 mmol/kg). On some occasions, subtraction techniques were used to eliminate the background signal from the catheter images prior to superimposing them onto a roadmap image. Snapshots of the canine carotids and aortas are shown in FIGS. 6 and 7, respectively.

Example 6

In Vivo Catheter MR Visualization

Using canines, a catheter coated with the formulation in accordance with the present invention/guide-wire combination is initially positioned in the femoral artery. Under MR guidance, the catheter is moved first to the aorta, then to the carotid artery, then to the circle of Willis, and on to the middle cerebral artery. The catheter movement is clearly seen in the vessels. The length of time to perform this procedure and the smallest vessel successfully negotiated is recorded.

Example 7

Paramagnetic Ion Safety Testing

A gadolinium leaching test is performed to ascertain the stability of the DTPA[Gd(III)] complex. Polyethylene sheets coated with the formulation in accordance with the present invention are subjected to simulated blood plasma buffers and blood plasma itself. NMR scans are taken and distinguish between chelated $Gd^{3+}$ and free $Gd^{3+}$. The results indicate that the $Gd^{3+}$ complex is stable under simulated blood conditions.

Example 8

Biocompatibility Testing

A biocompatibility test, formulated as non-specific binding of serum proteins, is carried out on polymeric surfaces coated in accordance with the present invention using an adsorption method of serum albumin labeled with fluorescent dyes. If the albumin is irreversibly adsorbed as detected by fluorescence of coated catheter surfaces, the coat is adjudged to be not biocompatible by this criterion.

Example 9

Determination of Coating Signal Intensities

A clinical 1.5 T scanner (Signa, General Electric Medical Systems) is used to determine the optimal range of coating densities (in mmol $Gd^{3+}$/m2) for producing appreciable signal enhancement on a series of silicon wafers coated with a polyethylene-Gd-containing coating in accordance with the present invention. The wafers are placed in a water bath and scanned cross-sectionally using a moderately high-resolution fast gradient-recalled echo (FGRE) sequence with TR≈7.5 ms/TE≈1.5 ms, 256×256 acquisition matrix and a 16 cm×16 cm field-of-view (FOV). The flip angle is varied from 10° to 90° in 10° increments for each coating density. A region of interest (ROI) is placed in the water adjacent to the wafer and the absolute signal is calculated.

For calibration of signal measurements obtained in different imaging experiments, a series of ten calibration vials is also imaged. The vials contain various concentrations of DTPA[Gd(III)], ranging from 0 mmol/mL to 0.5 mmol/mL.

This range of concentrations corresponds to a range of T1 relaxation times (from <10 ms to 1000 ms) and a range of T2 relaxation times. The signals in each vial are also measured and used to normalize the signals obtained near the wafers. Normalization corrections for effects due to different prescan settings between acquisitions and variable image scaling are applied by the scanner. A range of concentrations in the vials facilitates piece-wise normalization. An optimal range of coating densities is determined.

Example 10

Comparison Testing of MR-Visibility of Three Differently Coated Samples

Because many medical devices are made of polyethylene (PE), PE rods were used in a variety of tests in order to mimic the surface of a catheter or other medical devices. In this specific example (as fully set forth in the preparation of Sample 2), the PE rods (2 mm diameter) were functionalized or precoated with a hydrophilic polymer containing primary amine groups. Through amide linkage, diethylenetrimaminepentaacetic acid (DTPA) was covalently attached to the rods. Subsequently, Gd(III) was coordinated to the DTPA. The necessary contrast for MRI is the result of interactions of proton of water in body fluid (e.g., blood) with the highly magnetic Gd(III) ion, and the resulting shortening of T1 relaxation time of the water protons. To reduce the mobility of the DTPA[Gd(III)] complex linked to the carrier polymer for visualizing in accordance with the present invention, agarose gel was used to encapsulate the entire assembly. Such a rod was used as Sample 2 in the testing as further described below.

To test the effectiveness of agarose gel in reducing the mobility of the DTPA[Gd(III)] complex, and accordingly, enhancing the MR-visibility of the medical device, two other samples were tested in parallel. Sample 1 was a blank sample, i.e. a PE rod encapsulated with agarose gel but having no DTPA[Gd(III)] coordinated; Sample 2 was a PE rod with covalently linked DTPA[Gd(III)] with agarose gel encapsulation; Sample 3 was a PE rod encapsulated with agarose gel containing a DTPA[Gd(III)] complex, but the complex was not covalently linked to the PE rods. MRI tests were carried out in three media: 1) a fat-free food-grade yogurt (a tissue mimic); 2) a physiological saline (a serum mimic); and 3) human blood. In summary, the following three agarose-encapsulated samples were tested in each media: the blank sample having no DTPA[Gd(III)] complex, but encapsulated in agarose (Sample 1); the chemically-bound or covalently linked DTPA[Gd(III)] complex encapsulated in agarose (Sample 2); and the unbound DPTA[Gd(III)] encapsulated in agarose (Sample 3). Sample 1, the blank, gave no detectable MRI signal. Sample 2 gave clearly detectable signals up to ten hours. Sample 3 lost signal intensity with time, thereby indicating a slow leaching of DTPA[Gd(III)] complex out of the agarose gel matrix because it was not covalently bound to the polymer substrate of the medical device. Given the observed MR images of Samples 2 and 3, the agarose encapsulation is adjudged to be optimal.

Specific Preparation and Evaluation of MR-Visible PE Polymer Rods is as Follows

Preparation of Sample 1

Sample 1 was prepared by coating blank PE rods with agarose gel. The PE rods for Sample 1 and all samples were obtained from SurModics, Inc. (Eden Prairie, Minn.). Agarose (type VI-A) was purchased from Sigma, St. Louis, Mo., with gel point (1.5% gel) at 41.0°±1.5° C., gel strength (1.5%) expressed in units of elastic modulus larger than 1200 g/cm2, and melting temperature 95.0°±1.5° C. 0.60 g agarose was dissolved in 40 mL distilled water in a flask maintained at 100° C. for 5 min. The solution was kept in a water bath at 50-60° C. The PE rods were then dipped into the agarose solution. After removing the rods from the solution, the rods were cooled to room temperature in order to allow chill-set of a gel-coating to form on the rod surface. The same procedure was repeated to overcoat additional layers of agarose, and it was repeated for 5 times for each rod. Thus, all rods were expected to have about the same gel-coating thickness.

Preparation of Sample 2

Polyethylene (PE) rods with an amine-containing-polymer coating were provided by SurModics, Inc. PE surface of the rods is functionalized by a photochemical attachment of poly (N[2-aminopropyl]methacrylate) or poly(N[2-aminoethyl] methacrylate) in order to provide functional groups, more specifically, amine groups, on the functionalized surface of the rods. Again, the PE rods in the example were meant to mimic the surface of existing medical devices made from a wide variety of polymers. Diethylenetriaminepentaacetic acid (DTPA), gadolinium trichloride hexahydrate, GdCl3.6H2O (99.9%), dicyclohexylcarbodiimide (DCC), and 4-(dimethylamino)-pyridine (DMAP) were all purchased from Aldrich (Milwaukee, Wis.), and used without further purification. Agarose (type VI-A) was purchased from Sigma located at St. Louis, Mo., with gel point (1.5% gel) at 41.0°±1.5° C., gel strength (1.5%) larger than 1200 g/cm2, and melting temperature 95.0°±1.5° C. Human blood used in the MRI experiments were obtained from the University of Wisconsin Clinical Science Center Blood Bank.

Figure 8:
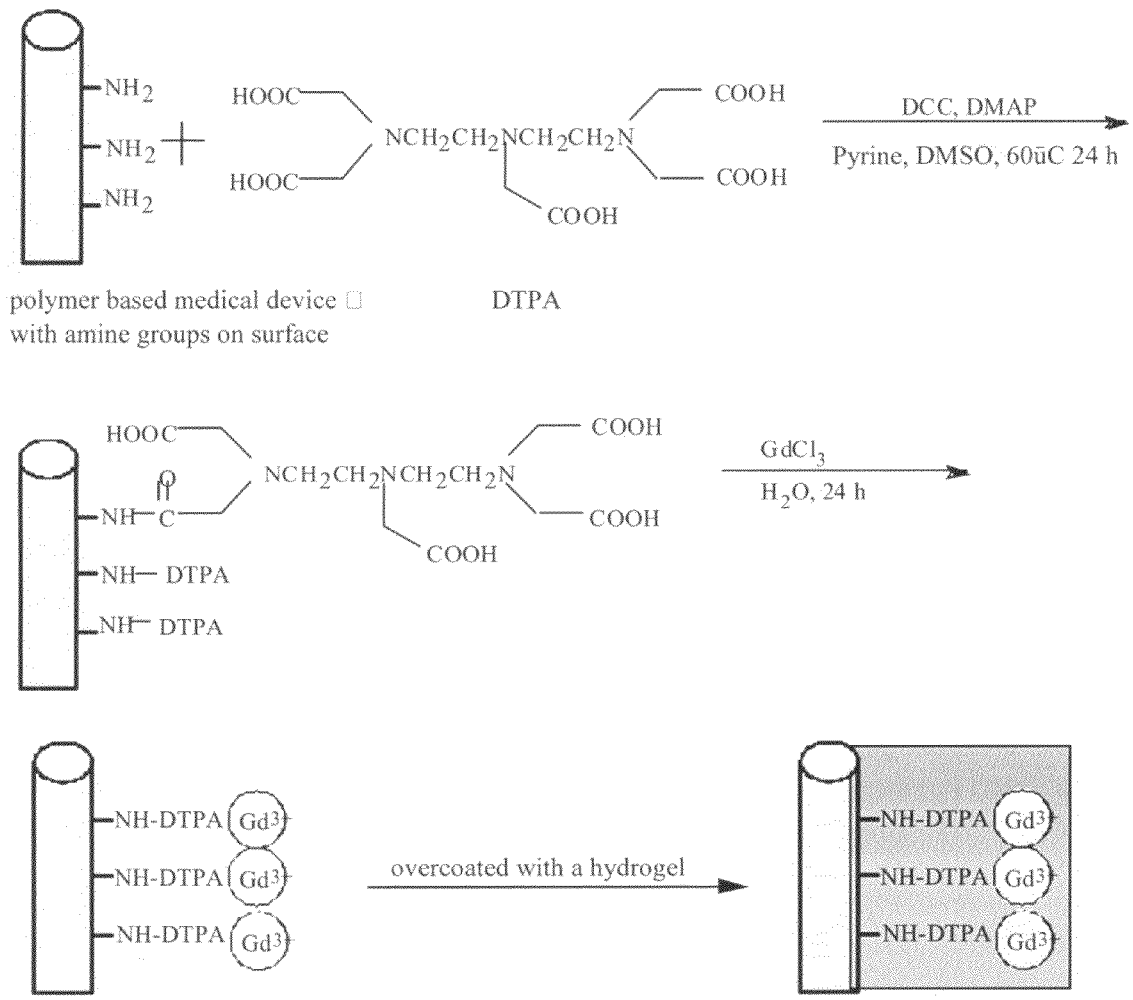
FIG. 8 is a schematic showing one example of a chemical synthesis of the present invention by which an existing medical device can be made MR-visible. More particularly.

The MRI-signal-emitting coatings were prepared on the PE rods, i.e. the pre-existing rods were made MR-visible, by the chemical synthesis depicted in FIG. 8. The individual steps of the chemical synthesis are explained in detail below.

To attach the DTPA (i.e. ligand) to the PE rods by amide linkage, 0.165 g DTPA (0.42 mmol) was dissolved in 30 mL of 1:1 (by volume) mixture of pyridine and DMSO in a flask and stirred at 80° C. for 30 min. Subsequently, 5-cm long PE rods having the amine-containing-polymer coating were immersed in the solution. After stirring for 2 hours at room temperature, 0.090 g DCC (0.43 mmol) and 0.050 g DMAP (0.41 mmol) solution in pyridine (4 mL) was slowly added to the solution while stirring. Then the reaction mixture was kept in an oil bath at 60° C. for 24 hours while stirring. Subsequently, the PE rods were removed from the solution and washed three times—first with DMSO and then with methanol, respectively.

To coordinate Gd(III) with the DTPA, now linked to the PE rods, 0.140 g GdCl3-6H2O (0.38 mmol) was dissolved in 15 mL of distilled water in a test tube. The DTPA-linked-PE rods were soaked in this solution at room temperature for 24 hours while stirring. The rods were then washed with distilled water several times and soaked in distilled water for an additional hour to remove any residual GdCl3.

To encapsulate the PE rods in the final step of the chemical synthesis as shown in FIG. 8, 0.60 g agarose was dissolved in 40 mL distilled water in a flask maintained at 100° C. for 5 min. The agarose solution so obtained was then kept in a water bath at 50-60° C. The DTPA[Gd(III)] linked rods were then dipped into the agarose solution. After removing the rods from the agarose solution, the rods were cooled down to room temperature in order to allow for encapsulation, i.e., to allow the gel coating to chill-set and cover the rod surface. The same procedure was repeated 5 times to coat additional layers of agarose gel on the rods. Thus, all rods, having undergone the same procedure, were expected to have about the same gel-coating thickness.

Preparation of Sample 3

Sample 3 was prepared by coating PE rods with agarose gel and a DTPA[Gd(III)] mixture. 0.45 g agarose (also obtained from Sigma) was dissolved in 30 mL distilled water in a flask maintained at 100° C. for 5 min. Then, 3 mL of 0.4% solution of DTPA[Gd(III)] was added to the agarose solution. The solution was kept in a water bath at 50-60° C. The rods were dipped into the agarose solution, and then were removed. The adsorbed solution on the rod was cooled to room temperature to allow a gel-coating to form. The same procedure was repeated to coat additional layers of agarose, and it was repeated for 5 times altogether for each rod. Thus, all rods were expected to have about the same gel coating thickness. Sample 3 differed from Sample 2 in that the DTPA[Gd(III)] complex was not covalently bonded to the PE rod using the methods of the present invention. Instead, a DTPA[Gd(III)] mixture was merely added to the agarose solution, resulting in dispersion of the same in the gel upon encapsulation in 5-layer coating.

Testing

The samples were then subjected to characterization by x-ray photoelectron spectroscopy (XPS) and magnetic resonance (MR) measurements. XPS measurements were performed with a Perkin-Elmer Phi 5400 apparatus. Non-monochromatized MgKα X-ray has been utilized at 15 W and 20 mA, and photoelectrons were detected at a take-off angle of 45°. The survey spectra were run in the binding energy range 0-1000 eV, followed by high-resolution spectra of C(1s), N(1s), O(1s) and Gd(4d).

MR evaluation of the signal-emitting rods was performed on a clinical 1.5T scanner. The PE rods were each visualized in the following medium: 1) yogurt as a suitable tissue mimic; 2) saline as an electrolyte mimic of blood serum; and 3) and human blood. Spin echo (SE) and RF spoiled gradient-recalled echo (SPGR) sequences were used to acquire images.

Results

The surface chemical composition of the rods was determined by the XPS technique. Table 2, below, lists the relative surface atomic composition of the untreated rods as provided by SurModics (Eden Prairie, Minn.). Table 3 shows the relative surface composition of the treated (DTPA[Gd(III)] linked) rods. After the chemical treatment outlined in FIG. 8, the relative composition of oxygen increased from 10.8% to 25.9% as seen in Tables 2 and 3. This indicates that DTPA is indeed attached to the polymer surface. Furthermore, it is clear that Gd(III) was complexed to the DTPA on the polymer surface, thus giving rise to the surface Gd composition of 3.2%.

TABLE 2

Surface compositions in % of 3 elements, C, N and O, of PE rods coated with the $NH_2$-containing polymer (SurModics).

| Location | C(1s) | N(1s) | O(1s) |
|---|---|---|---|
| 1 | 80.7 | 8.6 | 10.7 |
| 2 | 80.2 | 8.3 | 11.5 |
| 3 | 80.4 | 9.3 | 10.3 |
| average | 80.4 (±0.3) | 8.7 (±0.5) | 10.8 (±0.6) |

TABLE 3

Surface composition in % of 4 elements of the PE rods linked with DTPA[Gd(III)]

| Location | C(1s) | N(1s) | O(1s) | Gd(4d) |
|---|---|---|---|---|
| 1 | 65.2 | 5.8 | 25.9 | 3.1 |
| 2 | 63.2 | 7.2 | 26.5 | 3.1 |
| 3 | 63.6 | 7.8 | 25.2 | 3.3 |
| average | 64.0 (±1.0) | 6.9 (±1.0) | 25.9 (±0.7) | 3.2 (±0.1) |

The polymer rods linked with DTPA[Gd(III)] and encapsulated by agarose gel (Sample 2) were visualized in yogurt, saline and human blood. At the same time, the control rods, i.e., the PE rods having no chemical treatment but having only the gel overcoat (Sample 1) as well as PE rods coated with the gel in which DTPA[Gd(III)] is dispersed but not covalently linked (Sample 3) were also visualized in yogurt, saline and blood using spin echo (SE) and RF spoiled gradient-recalled echo (SPGR) sequences. Typical scan parameters for 2D SE sequence were: TR=300 ms, TE=9 ms, acquisition matrix=256×256, FOV=20 cm×20 cm, slice thickness=3 mm, flip angle=30°. Typical scan parameters for 3D SPGR sequence were: TR=18 ms, TE=3.7 ms. acquisition matrix=256×256, FOV=20 cm×20 cm, slice thickness=3 mm, flip angle=30°. The three kinds of samples and the MRI imaging set-up are illustrated in FIG. 9.

Figure 10:
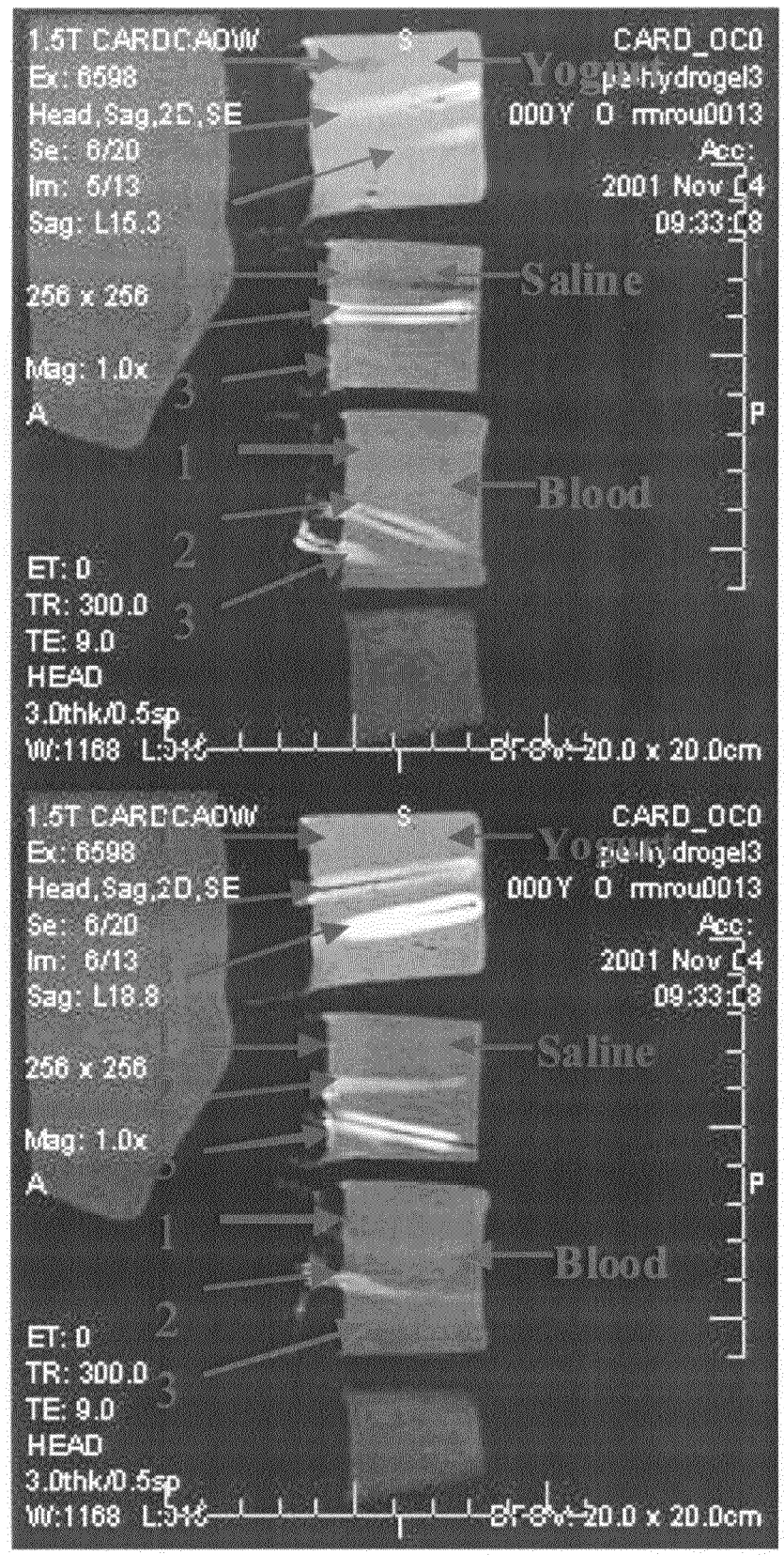
FIG. 10 is a temporal MR snapshot showing the MR-visibility of three samples in three different media (namely yogurt, saline and blood) after being introduced therein for 15+ minutes, wherein 1 is polyethylene ("PE")/agarose; 2 is PE-DTPA[Gd(III)]/agarose; and 3 is PE/(DTPA[Gd(III)]+agarose) in yogurt, saline, and blood 15 minutes later. The upper and lower frames represent different slices of the same image.
Figure 11:
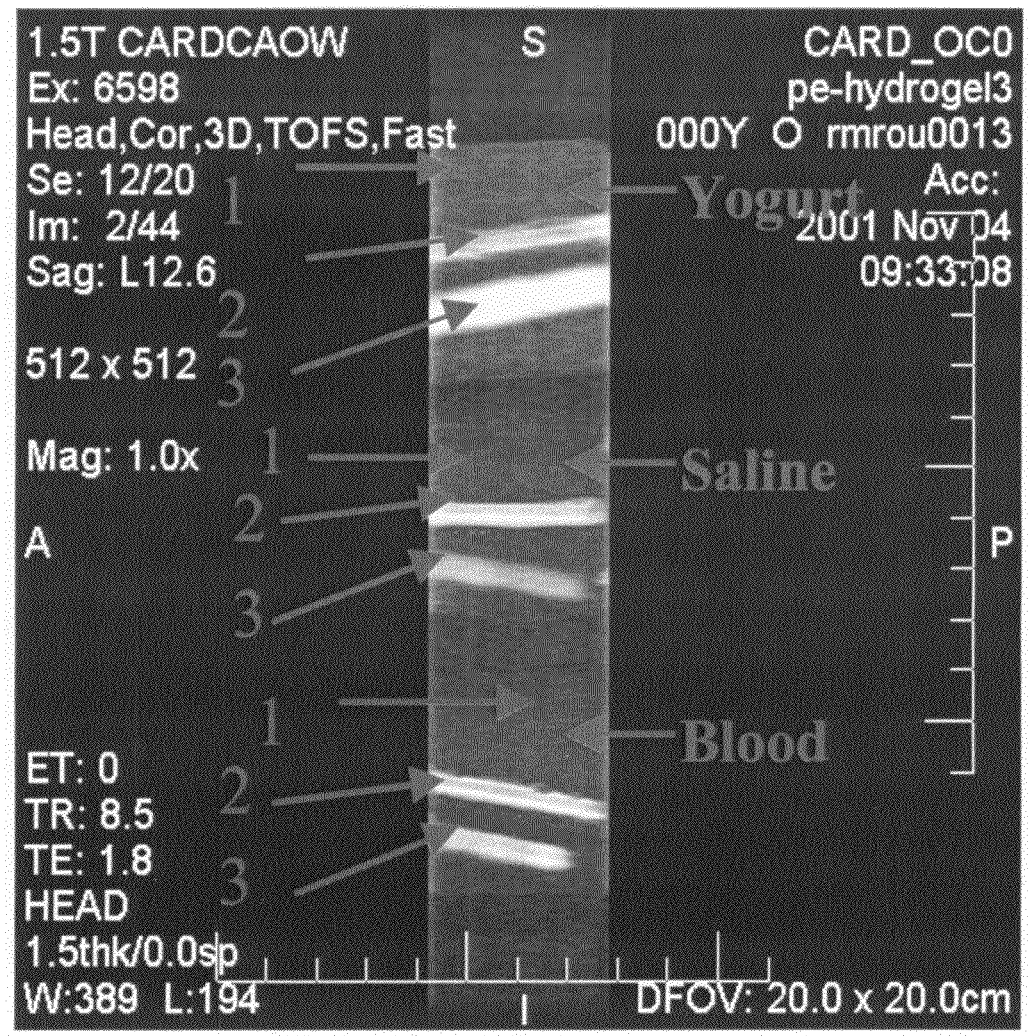
FIG. 11 is a temporal MR snapshot showing the MR-visibility of three samples in three different media (namely yogurt, saline and blood) after being introduced therein for 60+ minutes, wherein 1 is PE/agarose; 2 is PE-DTPA[Gd(III)]/agarose; and 3 is PE/(DTPA[Gd(III)]+agarose); in yogurt, saline, and blood 60+ minutes later.
Figure 12:
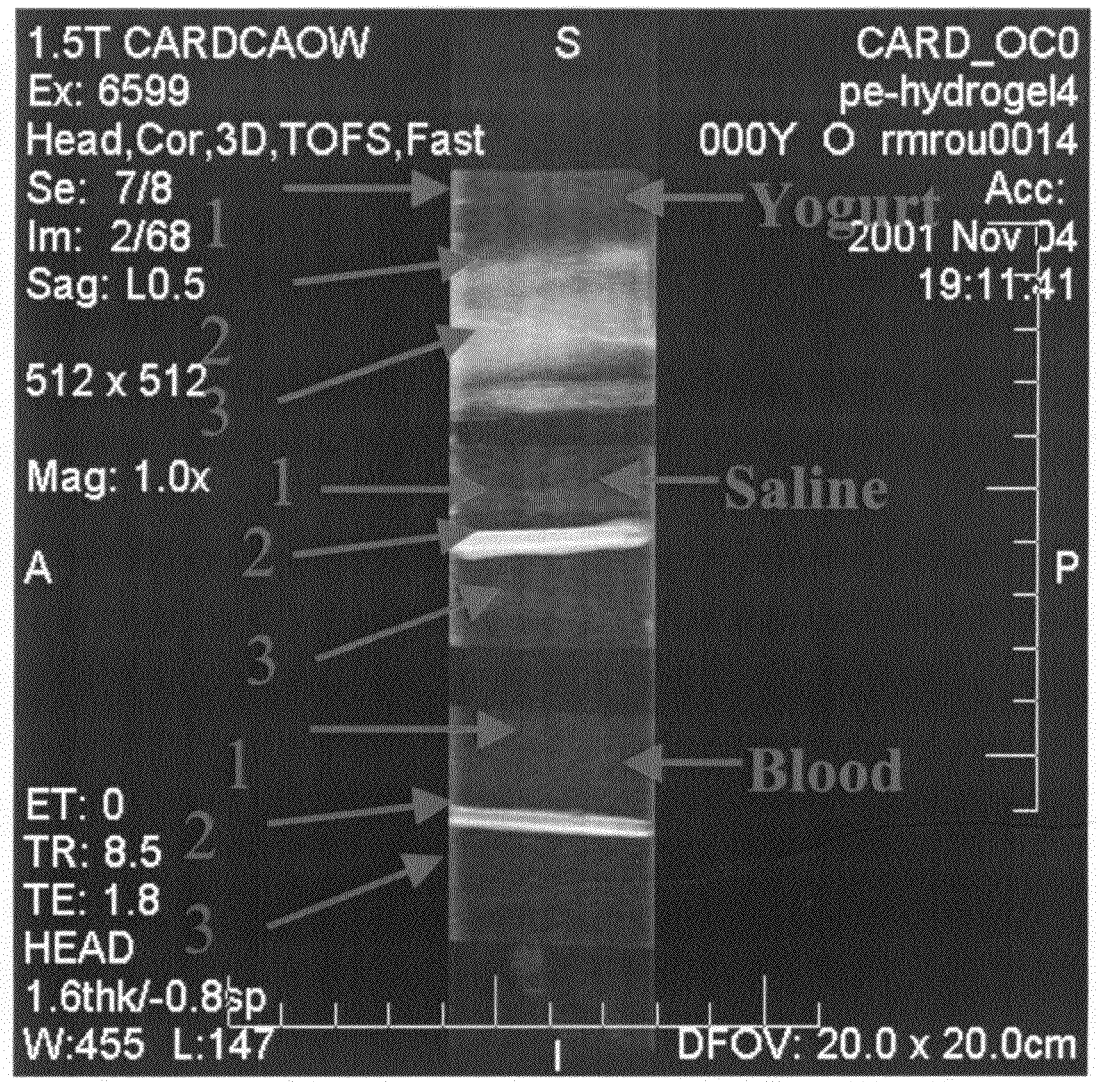
FIG. 12 is a temporal MR snapshot showing the MR-visibility in a longitudinal configuration of three samples in three different media (namely yogurt, saline and blood) after being introduced therein for 10+ hours, wherein 1 is PE/agarose; 2 is PE-DTPA[Gd(III)]/agarose; and 3 is PE/(DTPA[Gd(III)]+agarose); in yogurt, saline, and blood 10+ hours later.

The rods were visualized, and the results are shown in FIGS. 10-12. More particularly, FIG. 10 shows the longitudinal MR image of each sample in each medium after 15+ minutes; FIG. 11 shows the longitudinal MR images after 60+ minutes; and FIG. 12 shows the longitudinal MR images of each sample in each medium after 10+ hours. As these figures illustrate, Sample 1 (i.e. PE rods coated only with the gel and without DTPA[Gd(III)]) is not visible in all three media, i.e., yogurt, saline, or blood. Sample 2 (i.e. PE rods covalently-linked with DTPA[Gd(III)] with overcoats of the gel) is visible in yogurt, saline, and blood and was clearly visible even after 10 hours as shown in FIG. 12. Sample 3 is also visible in yogurt, saline, and blood; however, DTPA[Gd(III)] appears to leach and diffuse out of the gel overcoat with time presumably because it is not covalently bonded to the polymer rod. For example, after 10 hours, sample 3 is not visible in saline or blood.

The summary of the MR experiments is presented in Table 4. Consequently, Sample 2 (having DTPA[Gd(III)] covalently linked to polyethylene) exhibits better MR-visibility for longer periods of time compared to Sample 3. In addition, it appears that encapsulating rods or medical devices having the paramagnetic-metal-ion/ligand complex covalently linked thereto with a hydrogel encapsulation improves or enhances the MR-visibility thereof. In Table 4, a "+" indicates that the sample was visible, while "−" indicates that the sample was not visible.

TABLE 4

MR signals of the samples in yogurt, saline and blood

|  |  | 20 mins | 2 hours | 10 hours | 10 hours and replace the yogurt and blood |
|---|---|---|---|---|---|
| In yogurt | 1 | − | − | − | − |
|  | 2 | + | + | + | + |
|  | 3 | + | +, but the signal diffused and became larger in size | +, but the signal diffused much | + |
| In saline | 1 | − | − | − | − |
|  | 2 | + | + | +, and the signal as strong as that of 20 mins | +, and the signal as strong as that of 20 mins |
|  | 3 | + | +, but decreased | − | − |
| In blood | 1 | − | − | − | − |
|  | 2 | + | + | + | + |
|  | 3 | + | +, but decreased | − | − |

Example 11

Attaching DTPA to PE Rods Via Amide Linkage; Complexing Gd(III) with DTPA Linked PE Rods; Gelatin Encapsulating on DTPA[Gd(III)] Attached PE Rods; and Cross-Linking the Gel-Coating on PE Rods. The Schematic Structure of the Coating and Chemistry in Detail are Illustrated in FIGS. 13 and 14

Diethylenetriaminepentaacetic acid (DTPA), gadolinium trichloride hexahydrate, GdCl3.6H2O (99.9%), dicyclohexylcarbodiimide (DCC), 4-(dimethylamino)-pyridine (DMAP), dimethyl sulfoxide (DMSO), and pyridine were all purchased from Aldrich, and used without further purification. Gelatin type (IV) was provided by Eastman Kodak Company as a gift. Glutaraldehyde (25% solution) was purchased from Sigma. These materials were used in Example 11, as well as Examples 12-13.

Attachment of DTPA on PE Rods Via Amide Linkage 0.165 g DTPA (0.42 mmol) was dissolved in 30 mL of 2:1 (by volume) mixture of pyridine and DMSO in a flask and stirred at 80° C. for 30 min. Then, a 40-cm long polyethylene (PE) rod (diameter 2 mm) with the amine containing polymer precoating were immersed in the solution. The PE rods with an amine containing-polymer coating were provided by SurModics, Inc. They are functionalized by a photochemical attachment of poly(N[2-aminoethy 1]methacrylate).

3-aminopropyl]methacrylamide) in order to provide functional groups, more specifically, amino groups, on the functionalized surface of the rods. Again, the PE rods were meant to mimic the surface of existing medical devices made from a wide variety of polymers. After stirring for 2 hours at room temperature, a pyridine solution (4 mL) containing an amidation catalyst, 0.090 g DCC (0.43 mmol) in 0.050 g DMAP (0.41 mmol), was slowly added to the PE rod soaked solution with stirring. Subsequently, the reaction mixture was kept in an oil bath at 60° C. for 24 hours with stirring to complete the bonding of DTPA to the amine groups on the precoated polymer via amide linkage. Subsequently, the PE rods were removed from the solution and washed three times first with DMSO and then with methanol.

Complexation of Gd(III) with DTPA Linked PE Rods 0.50 g GdCl3.6H2O (0.38 mmol) was dissolved in 100 mL distilled water in a test tube. The DTPA linked PE rods (40-cm long) were soaked in the solution at room temperature for 24 hours while stirring, then the rods were washed with distilled water several times to remove the residual GdCl3.

Gelatin Coating on DTPA[Gd(III)] Attached PE Rods

A sample of gelatin weighing 20 g was dissolved in 100 mL of distilled water at 60° C. for 1 hour with stirring. The solution was transferred to a long glass tube with a jacket and kept the water bath through the jacket at 35° C. DTPA[Gd(III)] attached PE rods (40-cm long) were then dipped into the solution, and the rods upon removing from the solution were cooled to room temperature in order to allow a gel-coating to chill-set, i.e., to form as a hydrogel coating on the rod surface. The final dry thickness of gel-coating was around 30 µm. The same procedure may be repeated to overcoat additional layers of the gel. When it was repeated twice, the final dry thickness of gel-coating was around 60 µm.

Cross-Linking of the Gel-Coating on PE Rods.

Several minutes after the gel-coating, the coated PE rods was soaked in 0.5% glutaraldehyde 300 mL for 2 hours to cross-link the gelatin coating. Then the rods were washed with distilled water and further soaked in distilled water for one hour to remove any residual free glutaraldehyde and GdCl3. Finally the gel-coated rods were dried in air.

Results

The surface chemical composition of the rods was determined by the XPS technique. The results are similar to that in Example 10. After the chemical treatment, DTPA is indeed attached to the polymer surface and Gd(III) was complexed to the DTPA on the polymer surface with the surface Gd composition around 3%.

The polymer rods linked with DTPA[Gd(III)] and encapsulated by cross-linked gelatin visualized in a canine aorta using 2D and 3D RF spoiled gradient-recalled echo (SPGR) sequences. Typical scan parameters for 2D SPGR sequence were: TR=18 ms, TE=3.7 ms. acquisition matrix=256×256, FOV=20 cm×20 cm, slice thickness=3 mm, and flip angle=30°. Typical scan parameters for 3D SPGR sequence were: TR=8.8 ms, TE=1.8 ms. acquisition matrix=512×192, FOV=20 cm×20 cm, slice thickness=2 mm, and flip angle=60°.

Figure 15:
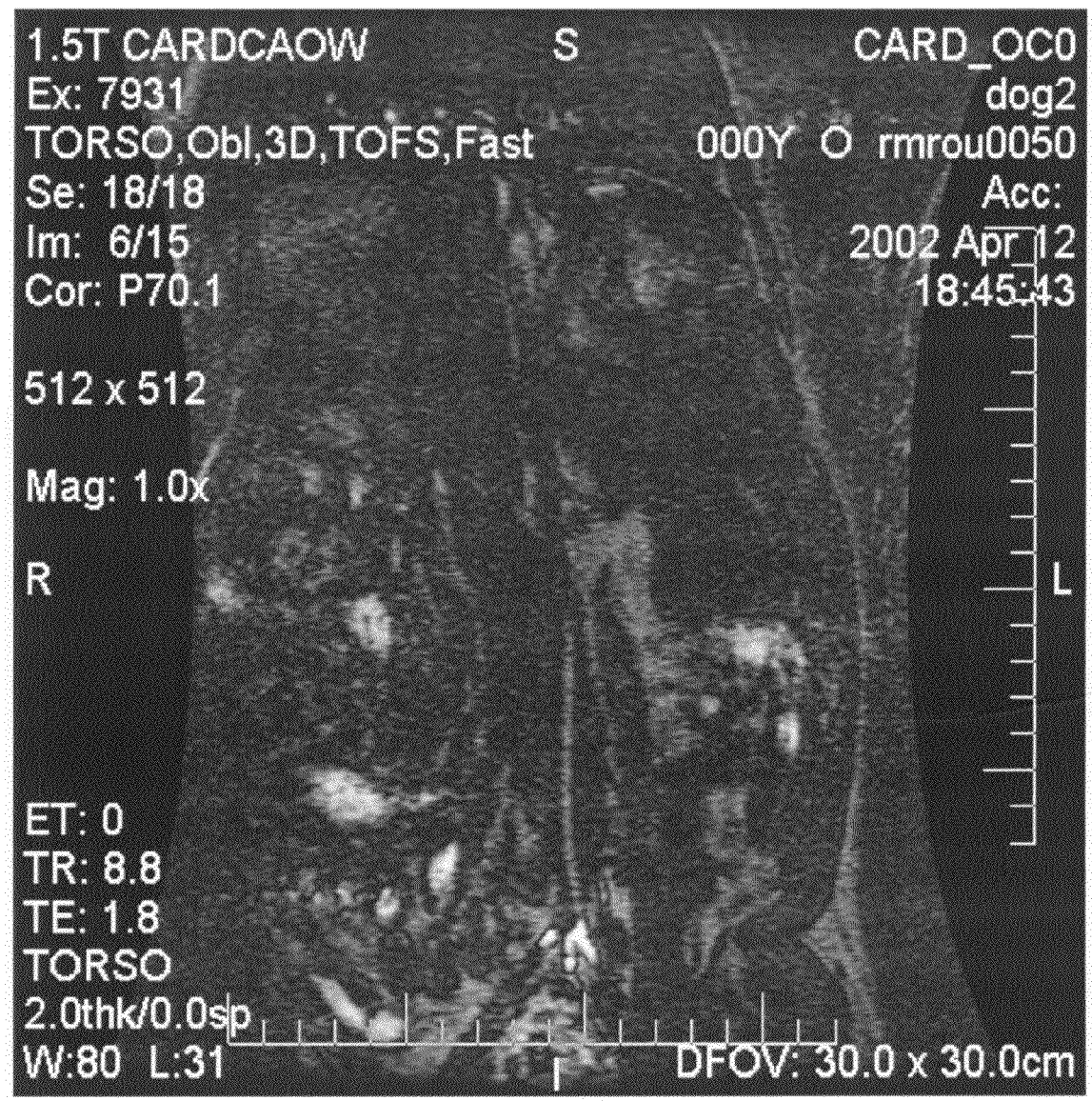
FIG. 15 is a temporal MR snapshot of a DTPA[Gd(III)] attached and then gelatin encapsulated PE rod in a canine aorta. More particularly.

The DTPA[Gd(III)] attached and then cross-linked gelatin encapsulated PE rods (length 40 cm, diameter 2 mm) were visualized in canine aorta, and the results are shown in FIG. 15. More particularly, FIG. 15 is a 3D maximum-intensity-projection (MIP) MR image of the PE rods 25 minutes after it was inserted into the canine aorta. The coated PE rods is clearly visible as shown in FIG. 15. It is noteworthy that the signal intensity appears to be improving with time.

Example 12

Coupling of Diethylenetriaminepentaacetic Acid (DTPA) to Poly(N-[3-aminopropyl]methylacrylamide); Functional Coating on a Guide-Wire; Cross-Linking of the Gel-Coating on the Guide-Wire; and Complexing Gd(III) to the DPTA-Linked Poly(N-[3-aminopropyl]methylacrylamide) and DTPA Dispersed in the Gel-Coating. The Schematic Structure of the Coating and Chemistry Detail are Illustrated in FIGS. 16 and 17

Again, the same materials as set forth in Example 11 were used in Example 12. The guide-wire used in this example is a commercial product from Medi-tech, Inc. (Watertown, Mass. 02272) with the diameter of 0.038 in. and length of 150 cm. Coupling of Diethylenetriaminepentaacetic Acid (DTPA) to Poly(N-[3-aminopropyl]methylacrylamide).

0.79 g of DTPA (2 mmol) was dissolved in 20 mL DMSO at 80° C. for 30 minutes, and then the solution was cooled to room temperature. 0.14 g poly(N-[3-aminopropyl]methylacrylamide) as a carrier polymer having one mmol of repeating unit and separately synthesized was dissolved with 0.206 g DCC (1 mmol) 20 mL of DMSO. The solution was slowly added to the DTPA solution dropwise with stirring. When all of the polymer and DCC solution was added, the final mixture was stirred for 8 hours at room temperature and then filtered. 200 mL of diethyl ether was added to the filtered solution to precipitate the product, a mixture of free DTPA and DTPA linked polymer. The solid product was collected by filtration and dried.
Functional Coating on a Guide-Wire 0.5 g of the above product and 20 g gelatin were dissolved in 100 mL of distilled water at 60° C. for 1 hour with stirring. The solution was transferred to a long glass tube with a jacket and kept in the water bath in the jacket at 35° C. Part of (60 cm) a guide-wire was then dipped into the solution. After removing the guide-wire from the solution, it was cooled to room temperature in order to allow a gel-coating to chill-set, i.e., to form as a hydrogel coating on the wire surface. The final dry thickness of gel-coating was around 30 µm. The same procedure may be repeated to overcoat additional layers of the gel. When it was repeated twice, the final dry thickness of gel-coating was around 60 µm.
Cross-Linking of the Gel-Coating on a Guide-Wire Several minutes after the gel-coating, the coated guide-wire was soaked in 300 mL of 0.5% glutaraldehyde for 2 hours to cross-link the gelatin and the carrier polymer. Then, the rods were first washed with distilled water and soaked further in distilled water for 2 hours to remove all soluble and diffusible materials such as free DTPA and glutaraldehyde.
Coordination of Gd(III) to the DPTA-Linked Poly(N-[3-aminopropyl]methylacrylamide) and DTPA Dispersed in the Gel-Coating After the cross-linking the gel-coating on the guide-wire with glutaraldehyde, the wire was soaked in a solution of 1.70 g GdCl3.6H2O dissolved in 300 mL of distilled water for 8 to 10 hours. Then, the wire washed with distilled water and further soaked for 8 to 10 hours to remove free GdCl3. Finally the gel-coated wire was dried in air.
Results The guide-wire with a functional gelatin coating, in which DTPA[Gd(III)] linked polymer was dispersed and cross-linked with gelatin, was visualized in a canine aorta using 2D and 3D RF spoiled gradient-recalled echo (SPGR) sequences. Typical scan parameters for 2D SPGR sequence were: TR=18 ms, TE=3.7 ms. acquisition matrix=256×256, FOV=20 cm×20 cm, slice thickness=3 mm, and flip angle=30°. Typical scan parameters for 3D SPGR sequence were: TR=8.8 ms, TE=1.8 ms. acquisition matrix=512×192, FOV=20 cm×20 cm, slice thickness=2 mm, and flip angle=60°.

Figure 18:
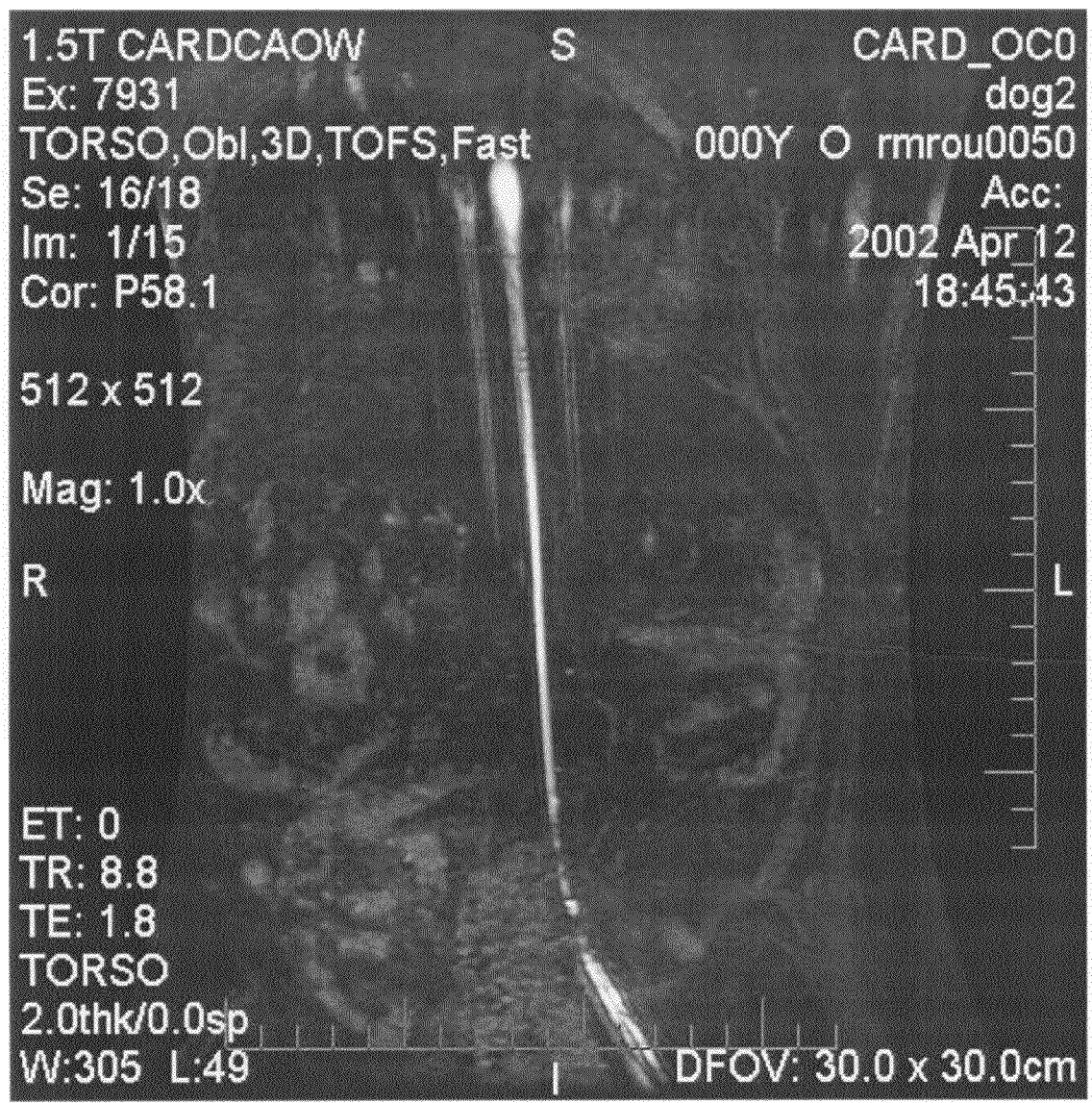
FIG. 18 is a temporal MR snapshot of a guide-wire with a functional gelatin coating in which a DTPA[Gd(III)] linked polymer was dispersed and cross-linked with gelatin. More particularly.

These results are shown in FIG. 18. In the experiments, the thickness of the gelatin coating is about 60 µm. The diameter of the coated guide-wire is about 0.038 in and the length of coated part is around 60 cm. FIG. 18 is the 3D maximum-intensity-projection (MIP) MR image of the guide-wire 10 minutes after it was inserted into the canine aorta. The coated guide-wire is visible in canine aorta as shown in FIG. 18. The signal of the coated guide-wire is very bright and improved with time.

Example 13

Synthesizing Diethylenetriaminepentaacetic Dianhydride (DTPAda); Functional Coating on a Guide-Wire and Catheter; Cross-Linking of the Gel-Coating on the Guide-Wire and Catheter; and Coordinating Gd(III) to the DPTA-Linked Gelatin Dispersed in the Gel-Coating. The Schematic Structure of the Coating and Chemistry in Detail are Illustrated in FIGS. 19 and 20

Again, the same materials set forth in Example 11-12 were used in Example 13. The catheter used in this example is a commercial product from Target Therapeutics, Inc. (San Jose, Calif.) having a length of 120 cm and diameter of 4.0 French.
Synthesizing Diethylenetriaminepentaacetic Dianhydride (DTPAda)

1.08 gram of DTPA (2.7 mmol), 2 mL acetic anhydride and 1.3 mL pyridine were stirred for 48 hours at 60° C. and then the reaction mixture was filtered at room temperature. The solid product washed to be free of pyridine with acetic anhydride and then with diethyl ether, and is dried.
Coupling of Diethylenetriaminepentaacetic Acid (DTPA) to Gelatin 0.6 g gelatin (0.16 mmol of lysine residue) was dissolved in 20 mL of distilled water at 60° C. for 1 hours. Then the solution was kept above 40° C. ⅓ of the gelatin solution and ⅓ of the total DTPAda weighing 0.5 g (1.4 mmol) were successively added to 20 mL of water at 35° C. with stirring. This step was carried out by keeping the solution pH constant at 10 with 6N NaOH. This operation was repeated until all the reagents were consumed. The final mixture was stirred for an additional 4 hours. Then, the pH of the mixture was adjusted to 6.5 by adding 1N HNO3.
Functional Coating on a Guide-Wire and Catheter 5.0 g DTPA linked gelatin and DTPA mixture (around 1:1 by weight) and 20 g of fresh gelatin were dissolved in 100 mL distilled water at 60° C. for one hour with stirring. The solution was transferred to a long glass tube with a jacket and kept in the water bath in the jacket at 35° C. A part of (60 cm) a guide-wire was then dipped into the solution. After removing the guide-wire from the solution, it was cooled to room temperature in order to allow a gel-coating to chill-set, i.e., to form as a hydrogel coating on the rod surface. The final dry thickness of gel-coating was around 30 µm. The same procedure may be repeated to overcoat additional layers of the gel. When it was repeated twice, the final dry thickness of gel-coating was around 60 µm.

Using the same procedure, a part of (45 cm) catheter (diameter 4.0 F) was coated with such functional gelatin, in which DTPA linked gelatin dispersed.

Cross-Linking of the Gel-Coating on PE Rods

Several minutes after the gel-coating, the coated guidewire and catheter were soaked in 300 mL of 0.5% glutaraldehyde for 2 hours in order to cross-link the gelatin coating. Then, guide-wire and catheter were first washed with distilled water and soaked further for 2 hours to remove all soluble and diffusible materials such as free DTPA and glutaraldehyde.

Coordinating Gd(III) to the DPTA-Linked Gelatin Dispersed in the Gel-Coating

After the cross-linking the gel-coating on a guidewire and catheter with glutaraldehyde, the rods were soaked in a solution of 1.7 g GdCl3.6H2O dissolved in 300 mL of distilled water for 8 to 10 hours. Then the guide-wire and catheter were washed with distilled water and further soaked for 8 to 10 hours to remove the free GdCl3. Finally the gel-coated guide-wire and catheter were dried in air.

Results

Figure 21:
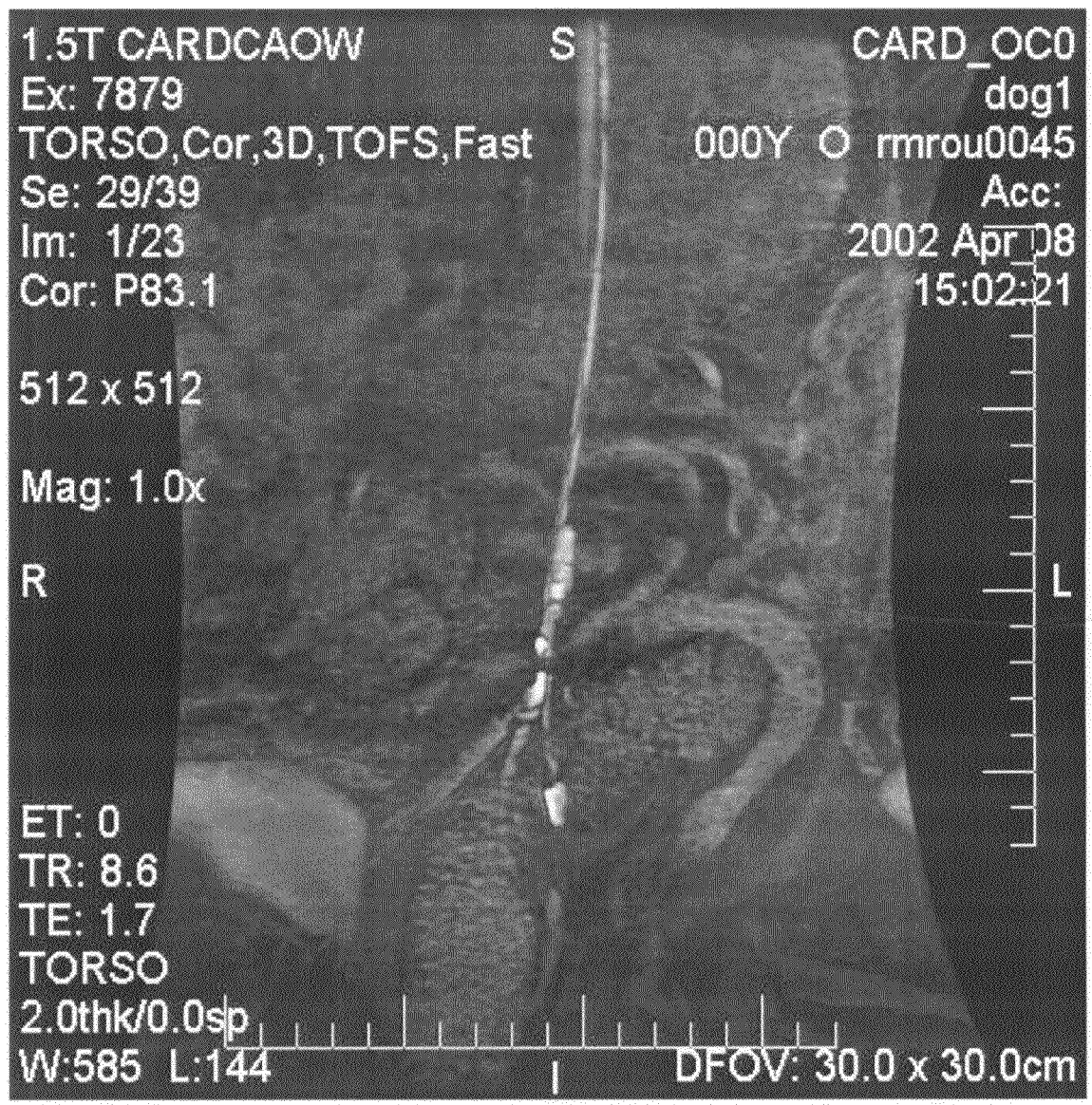
FIG. 21 is a temporal MR snapshot of a guide-wire with a functional gelatin coating in which a DTPA[Gd(III)] linked gelatin was dispersed and cross-linked. More particularly.

The guide-wire and catheter with a functional gelatin coating, in which DTPA[Gd(III)] linked gelatin was dispersed, was visualized in a canine aorta using 2D and 3D RF spoiled gradient-recalled echo (SPGR) sequences. Typical scan parameters for 2D SPGR sequence were: TR=18 ms, TE=3.7 ms. acquisition matrix=256×256, FOV=20 cm×20 cm, slice thickness=3 mm, and flip angle=30°. Typical scan parameters for 3D SPGR sequence were: TR=8.8 ms, TE=1.8 ms. acquisition matrix=512×192, FOV=20 cm×20 cm, slice thickness=2 mm, and flip angle=60°. These results are shown in FIG. 20. In the experiments, the thickness of gelatin coating is about 60 μm. The diameter of the coated guide-wire is 0.038 in and the length of coated part is around 60 cm. FIG. 21 is the 3D MIP MR image of the guide-wire 30 minutes after it was inserted into the canine aorta. The coated guide-wire is visible in canine aorta as shown in FIG. 21. The signal of the coated guide-wire improved with time.

Figure 22:
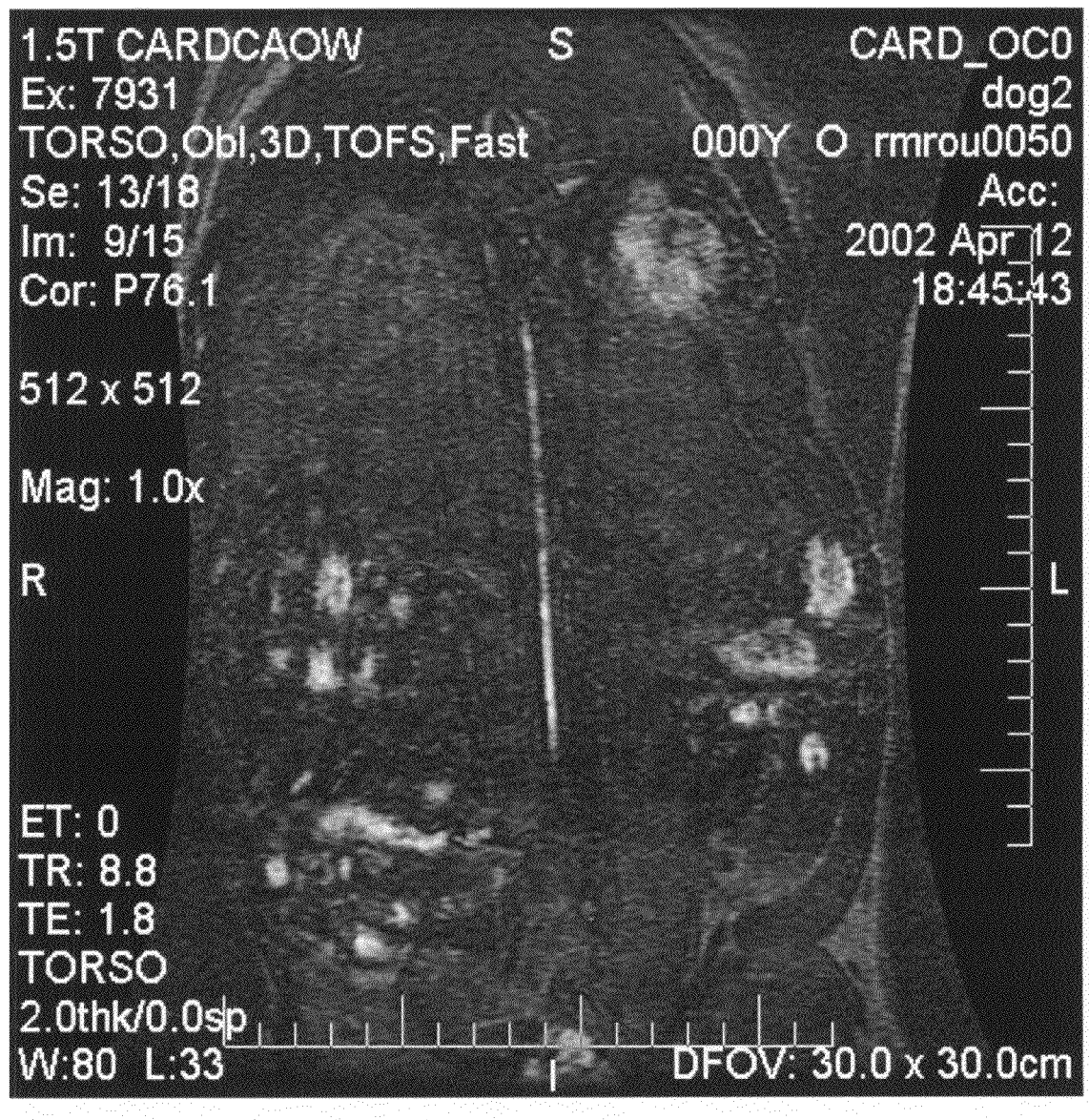
FIG. 22 is a temporal MR snapshot of a catheter with a functional gelatin coating in which a DTPA[Gd(III)] linked gelatin was dispersed and cross-linked. More particularly.

The catheter with a functional gelatin coating, in which DTPA[Gd(III)] linked gelatin was dispersed, was visualized in canine aorta, the results of which are shown in FIG. 22. In the experiments, the thickness of gelatin coating is about 30 μm. The diameter of the coated catheter is 4.0 F and the length of coated part is around 45 cm. Typical scan parameters for 3D SPGR sequence were: TR=8.8 ms, TE=1.8 ms. acquisition matrix=512×192, FOV=20 cm×20 cm, slice thickness=2 mm, and flip angle=60°. FIG. 22 is the 3D MIP MR image of the catheter 20 minutes after it was inserted into the canine aorta. The coated catheter is visible and bright in canine aorta as shown in FIG. 22. The MR signal intensity of coated catheter improved with time.

In summary, the present invention provides a method of visualizing pre-existing medical devices under MR guidance utilizing a coating, which is a polymeric-paramagnetic ion complex, on the medical devices. The methods practiced in accordance with the present invention provide various protocols for applying and synthesizing a variety of coatings.

Example 14

Preparation of Polyethylene Rods Coated with Gelatin and DTPA[Gd(III)] Mixture

Diethylenetriaminepentaacetic acid (DTPA), gadolinium trichloride hexahydrate, $GdCl_3 \cdot 6H_2O$ (99.9%), and fluorescein were all purchased from Aldrich (Milwaukee, Wis.), and they were used without further purification. Gelatin Type-IV and bis-vinyl sulfonyl methane (BVSM) were provided by Eastman Kodak Company. Glutaraldehyde (25% solution) was purchased from Sigma (St. Louis, Mo.). The guide-wire used in this example was a commercial product from Meditech, Inc. (Watertown, Mass.) having a diameter of 0.038 inch and a length of 150 cm. The polyethylene (PE) rods having a diameter of 2 mm were supplied by SurModics, Inc. (Eden Prairie, Minn.).

Coating the PE Rods

A gelatin and DTPA[Gd(III)] mixture was coated on the polyethylene rods. Different coatings having different cross-link densities were prepared as set forth in Table 5. For each of the samples, gelatin and DTPA[Gd(III)] were dissolved in distilled water at 80° C. for 30 minutes and stirred. Different amounts of cross-linker (BVSM) were added to the gelatin solutions with stirring after it was cooled down to 40° C. The compositions of the gelatin solutions used for the coating are collected in Table 5.

TABLE 5

Compositions of different gelatin solutions for coating

| Sample | BVSM content relative to dry gelatin in the coating (% wt) | Amount of gelatin (gram) | DTPA content (gram) | $GdCl_3 \cdot 6H_2O$ (gram) | Water (mL) | 3.6% (by wt) solution of BVSM (mL) mixed |
|---|---|---|---|---|---|---|
| 1 | 0 | 2 | 0.1 | 0.094 | 10 | 0 |
| 2 | 1 | 2 | 0.1 | 0.094 | 9.45 | 0.55 |
| 3 | 2 | 2 | 0.1 | 0.094 | 8.9 | 1.1 |
| 4 | 4 | 1 | 0.05 | 0.047 | 8.9 | 1.1 |
| 5 | 8 | 1 | 0.05 | 0.047 | 7.8 | 2.2 |

Samples having the above formulations were transferred to a glass tube and kept in a water bath at 35° C. A bare PE rod (5 cm in length) was then dipped into the solution, and then removed. The rod was then cooled to room temperature to allow chill-setting of the gelatin solution and to form the coating on the rod surface. The same procedure was repeated to overcoat additional layers of gel. The final dry thickness of gel-coating was about 60 μm.

The gelatin coatings were dried in air while being chemically cross-linked by BVSM. The dried and cross-linked samples were then soaked in distilled water for 12 hours. Soaking each sample in distilled water may remove the DTPA [Gd(III)] that was not physically or chemically constrained by the cross-linked network of gelatin overcoat. Because the DTPA[Gd(III)] complexes were not chemically linked to the gelatin chains, most of them would be expected to diffuse out of the coating when soaked in water, whereas some of DTPA [Gd(III)] may be confined by the crystal domains in gelatin or by hydrogen bonding between gelatin chains and DTPA. In any event, after the soaking, the gelatin coating was dried again in air before MRI test.

MR Visibility Test of the Functional Coating on PE Rod

Figure 24:
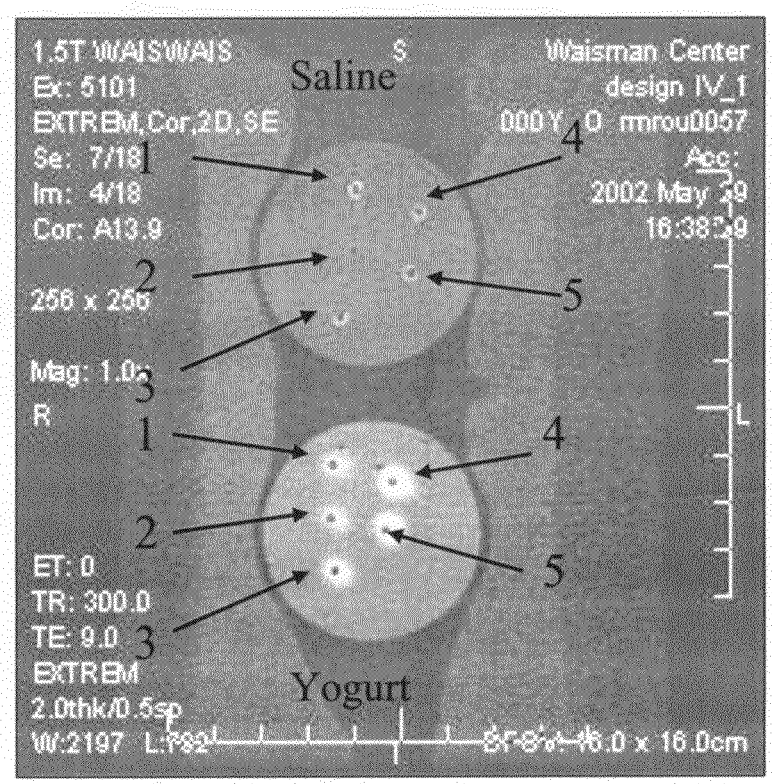
FIG. 24 is a temporal MR snapshot of PE rods having the functional gelatin coatings of Formula (VI) set forth below. As listed in Table 5 below, the samples designated as 1, 2, 3, 4 and 5 have different cross-link densities as varied by the content of the cross-linker (bis-vinyl sulfonyl methane (BVSM)) therein. Each of samples 1 through 5 was MRI tested in two immersing media, namely, saline and yogurt.

The MR visibility of the samples prepared as outlined above, was tested in two media: saline and yogurt. As shown above in Table 5, the BVSM content in the coatings of the samples designated 1, 2, 3, 4, and 5 were 0% (i.e. no cross-linker), 1%, 2%, 4% and 8%, respectively. FIG. 24 shows the MR image of the samples 1 through 5 in yogurt and saline. All of the samples were well visualized in yogurt. This implies that at least some of the contrast agent, namely DTPA[Gd (III)] complex, was encapsulated by the gel coating, and produced the MR signal contrast in the imaging. It is possible that at least some of DTPA[Gd(III)] complex may be tightly associated with microcrystals of gelatin upon being chill-set. Accordingly, it is possible that some fraction of the complexes cannot be freed and diffused out of the gelatin matrix upon swelling during the presoak, even without chemical cross-linking. Thus, the MRI signal intensity may be independent of the cross-link density. As shown in FIG. 24, the invisibility of sample 2 in saline may be due to the gel coating coming off after being soaked in water for twelve hours. The hydrogel coating may be more stable with the higher cross-link densities of samples 4 and 5.

Diffusion of a Fluorescent Probe in Swollen Gelatin Gel

To assess the stability of DTPA[Gd(III)] in the gelatin coating, the diffusion of a fluorescence probe in gelatin was studied by the technique of fluorescence recovery after photobleaching (FRAP). The instrument and data analysis scheme are described in Kim, S. H. and Yu, H., J. Phys. Chem. 1992, 96, 4034, which is hereby fully incorporated by reference. Fluorescein was used as the fluorescence probe due, in part, to its molecular size being roughly the same as that of DTPA[Gd(III)].

Figure 25:
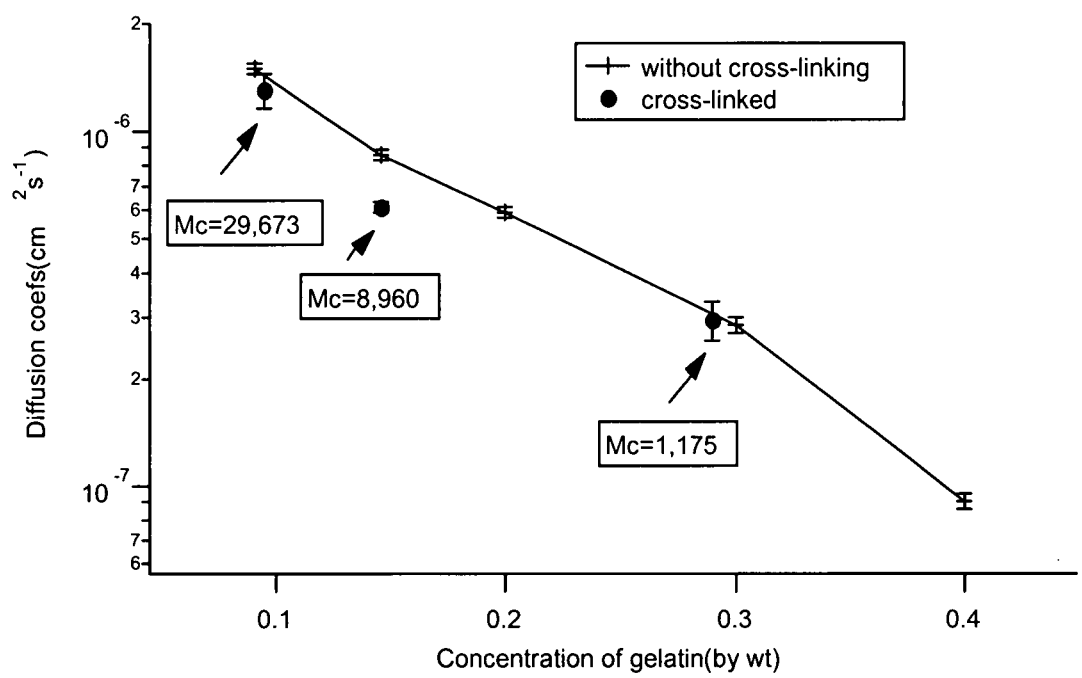
FIG. 25 is a graph depicting the diffusion coefficients of a fluorescent probe, namely, fluorescein, in swollen gelatin hydrogel as determined by the technique of FRAP.

The focus of the study was to examine the possible retardation effects of gelatin concentration and cross-link density on the diffusion, which was determined at room temperature, i.e., below the gel point of gelatin. The measured diffusion coefficient of fluorescein in gelatin solution is shown in FIG. 25. The diffusion of fluorescein probe slows down with the increase of gelatin concentration. The diffusion coefficient decreases from $1.5 \times 10^{-10}$ to $9 \times 10^{-12}$ m2s−1 when the concentration of gelatin increases from 9% to 40%. The diffusion coefficients in the cross-linked and non-cross-linked gel may be comparable provided that the gelatin concentrations are similar. Accordingly, the probe diffusion is more likely controlled by the concentration of gelatin rather than the cross-link density. On the other hand, the cross-link density may determine the swelling ratio of gelatin, i.e., the concentration of gelatin in aqueous solution.

Without intending to be limited by or restricted to any particular scientific theory, it appears that based upon the diffusion coefficient data, it may be possible to estimate how long will it take for DTPA[Gd(III)] or other paramagnetic-metal-ion/chelate complexes to diffuse out of the gelatin coating. For example, if the thickness of the gelatin coating is 60 μm, and the diffusion coefficient is $9 \times 10^{-12}$ m2s−1, DTPA may diffuse out of the coating in about 67 seconds. In the MRI experiments, the samples were already soaked in water for 12 hours before MRI test. Hence, all of mobile DTPA[Gd(III)] should have diffused out of the coating during the soaking in water. Based on the MRI experiments, however, it appears that some fraction of DTPA[Gd(III)] remained in the gel. Thus, it may be possible that some of the DTPA[Gd(III)] complexes are tightly associated with microcrystals of gelatin upon being chill-set such that a fraction of them, albeit small, cannot diffuse out of the gelatin matrix upon swelling during the presoak. Similarly, the FRAP experiments appear to demonstrate that there was still fluorescence signal after the gelatin films were soaked in water for 18 hours, including the gelatin films that were not cross-linked. As a result, it appears that some fraction of fluorescein was trapped inside the gelatin and may be unable to diffuse out.

Physical Properties of Hydrogels, and More Particularly, Gelatin Hydrogel

Figure 26:
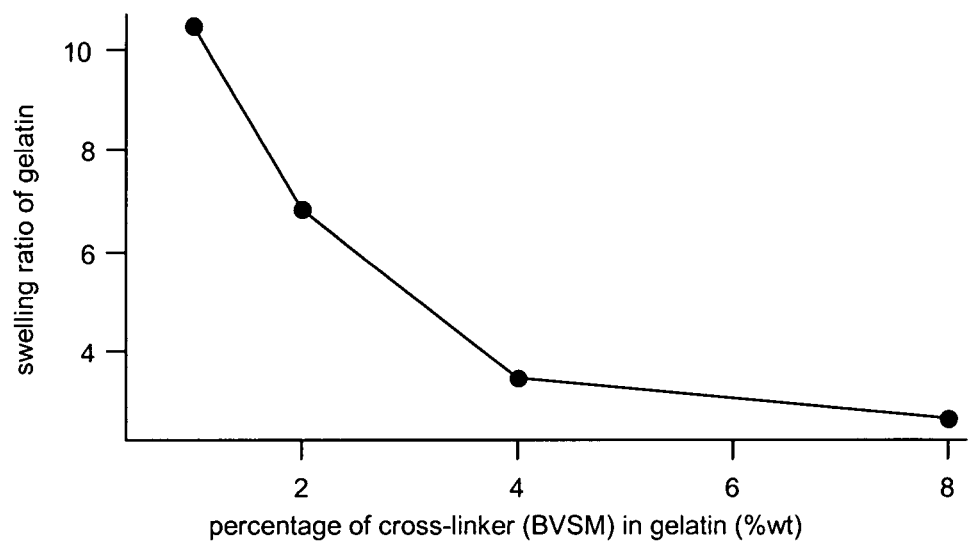
FIG. 26 is a graph plotting the volume swelling ratio of cross-linked gelatin against the cross-linker content, by weight % based on dry gelatin. A solution of BVSM (3.6%) was added to a gelatin solution in appropriate amount, then the gelatin coating was allowed to dry in air at room temperature while the cross-linking reaction proceeded. Once thoroughly dried, the swelling experiment in water was performed at room temperature.
Figure 27:
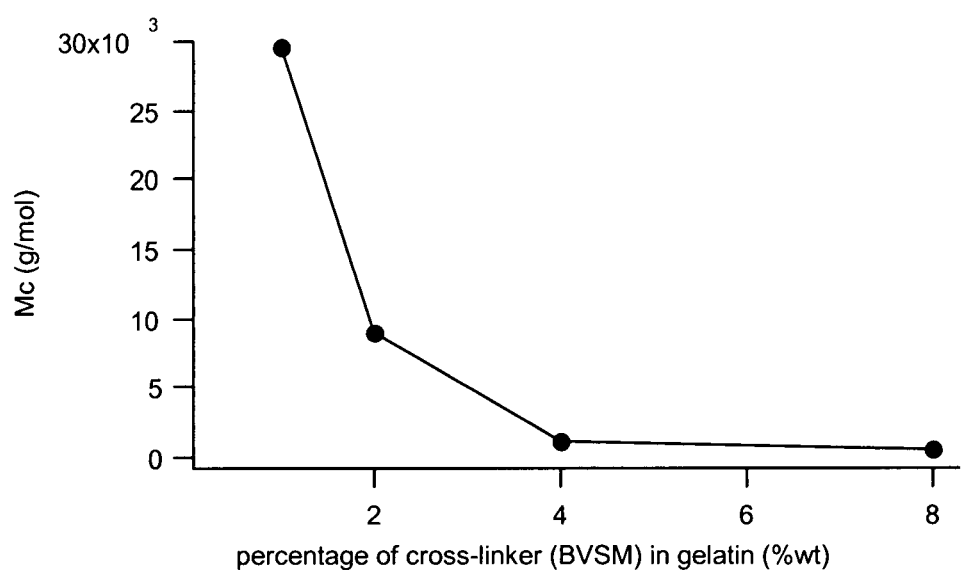
FIG. 27 is a graph plotting the average molecular weight between a pair of adjacent cross-link junctures Mc against BVSM content from the data shown in FIG. 26, with the Flory-Huggins solute-solvent interaction parameter for the gelatin/water system being 0.496.

The properties of hydrogel in solution may be controlled by the cross-link density. In our experiments the cross-link density of gelatin was measured by the water swelling method. FIG. 26 depicts the volume swelling ratio of cross-linked gelatin at equilibrium. The swelling ratio is defined as the ratio of the volume of water swollen gel to the volume of dry gel. The swelling ratio tends to decrease as the amount of cross-linker increases in gelatin. As shown in FIG. 26, the cross-linking saturation is reached by 4% BVSM in gelatin, hence 8% solution gave almost the same swelling ratio as that of 4%. This may indicate that most of the amine groups in the gelatin were consumed when the cross-linker, BVSM, is up to 4%. From the data in FIG. 26, the cross-link density is calculated as shown in FIG. 27. The cross-link density is characterized by the average molecular weight. Mc between a pair of adjacent cross-link junctures. The Flory-Huggins solute-solvent interaction parameter for gelatin/water is taken to be 0.497 in calculating Mc.

Figure 28:
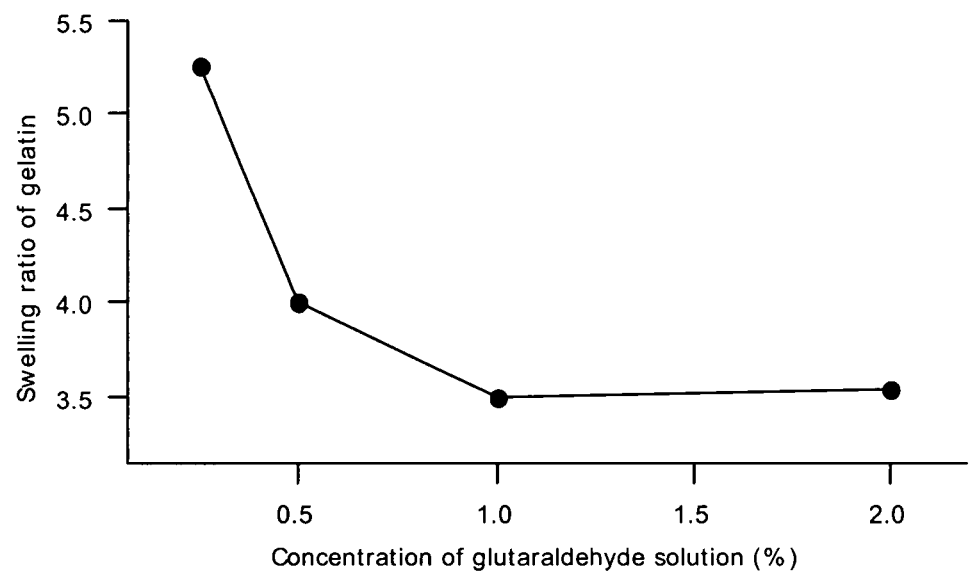
FIG. 28 is a graph plotting the volume swelling ratio of cross-linked gelatin against the glutaraldehyde concentration as the cross-linker. Gelatin gel was prepared and allowed to dry in air for several days. Then, the dry gel was swollen in water for half an hour, then soaked into a glutaraldehyde solution for 24 hours. The cross-linked gel was resoaked in distilled water for 24 hours. Then, the cross-linked gel was dried in air for one week. The swelling experiment of the completely dried gel was performed in water at room temperature.
Figure 29:
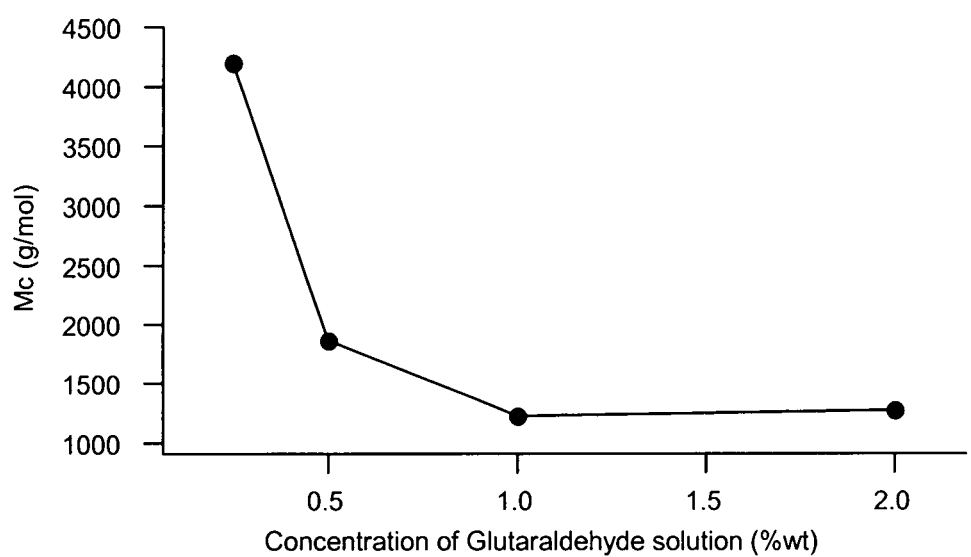
FIG. 29 is a graph plotting the average molecular weight between a pair of adjacent cross-link junctures Mc against glutaraldehyde concentration from the data shown in FIG. 28, with the Flory-Huggins solute-solvent interaction parameter for the gelatin/water system being 0.496.

The properties of gelatin cross-linked by the glutaraldehyde, were also studied and the results are shown in FIGS. 28 and 29. Here, the cross-linked gelatin was prepared as follows. Gelatin gel without BVSM was prepared and allowed to dry in air for several days. The dry gel, so obtained, was swollen in water for half an hour, then soaked into a glutaraldehyde solution for 24 hours at room temperature. In FIG. 28, a graph plotting the swelling ratio of cross-linked gelatin against glutaraldehyde concentration is displayed while a graph plotting Mc against glutaraldehyde concentration is shown in FIG. 29.

Example 15

In Vivo Test of MR Signal Emitting Coatings

Functional Coatings on a Guide-Wire and Catheter 1.7 g DTPA and 20 g of fresh gelatin were dissolved in 100 mL distilled water at 80° C. for one hour with stirring. The solution was transferred to a long glass tube with a circulating water jacket, through which the solution was maintained at 35° C. by being connected to a thermostated water bath at the same temperature. A part of (60 cm) a guide-wire or catheter was then dipped into the solution. After removing the guide-wire or catheter from the solution, it was cooled to room temperature in order to allow a gel-coating to chill-set, i.e., to form as a hydrogel coating on the wire or catheter surface. The same procedure may be repeated to overcoat additional layers of the gel. When it was repeated twice, the final dry thickness of gel-coating was about 60 μm.

Cross-Linking of the Gel-Coatings on a Guide-Wire and Catheter

Several minutes after the gel-coating, the coated wire or catheter was soaked in 300 mL of 0.5% glutaraldehyde solution for 2 hours in order to cross-link the gelatin coating. Then, the wire or catheter was first washed with distilled water and soaked further for 2 hours to remove all soluble and diffusible materials such as mobile DTPA and glutaraldehyde.

Coordinating Gd(III) to the DPTA-Linked Gelatin Dispersed in the Gel-Coating

After the cross-linking the gel-coatings on the surface of the wire or catheter with glutaraldehyde, the wire or catheter was soaked in a solution of GdCl3.6H2O solution (1.7 g dissolved in 300 mL of distilled water) for 8 to 10 hours. Subsequently, the guide-wire or catheter washed with distilled water and further soaked for 8 to 10 hours to remove the free GdCl3. Finally the gel-coated guide-wire or catheter was dried in air.

MRI Results

Figure 30:
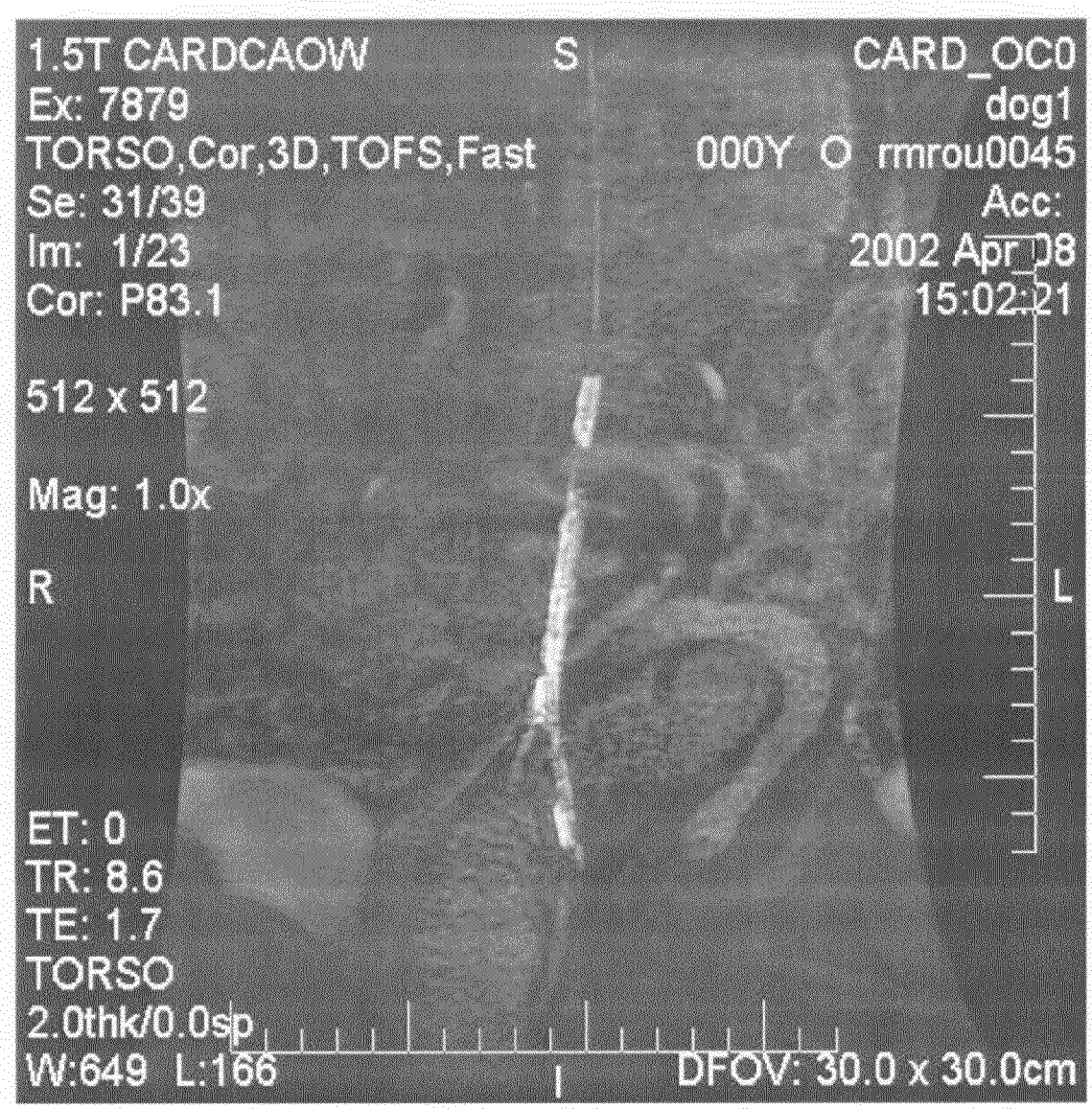
FIG. 30 is a temporal MR snapshot of a guide-wire with a functional gelatin coating of the fifth embodiment of the present invention illustrated in FIG. 23 in which an MR contrast agent DTPA[Gd(III)] was sequestered by gelatin gel. The dry thickness of the entire coating was about 60 μm, the length of coated section of the guide-wire was about 60 cm with the diameter of about 0.038 in. The image was acquired 15 minutes after the rod was inserted into live canine aorta.

The guide-wire and catheter having functional gelatin coatings, in which DTPA[Gd(III)] linked gelatin was dispersed, was visualized in a canine aorta using 2D and 3D RF spoiled gradient-recalled echo (SPGR) sequences. Typical scan parameters for 2D SPGR sequence were: TR=18 ms, TE=3.7 ms. acquisition matrix=256×256, FOV=20 cm×20 cm, slice thickness=3 mm, and flip angle=30°. Typical scan parameters for 3D SPGR sequence were: TR=8.8 ms, TE=1.8 ms. acquisition matrix=512×192, FOV=20 cm×20 cm, slice thickness=2 mm, and flip angle=60°. These results are shown in FIG. 30. In the experiments, the thickness of gelatin coating is 60 µm. The diameter of the coated guide-wire is 0.038 in and the length of coated part is around 60 cm. FIG. 30 is the 3D MIP MR image of the guide-wire 15 minutes after it was inserted into the canine aorta. The coated guide-wire is visible in canine aorta as shown in FIG. 30. Similar MRI results were obtained with the coated catheter.

Example 16

A Multi-Mode Medical Device System Having Tracking, Internal Imaging, and Visualizing (Wireless Marker) Capabilities A multi-mode medical device system 200 according to this example, and one embodiment of the present invention, is shown in FIGS. 33 and 34. The multi-mode medical device system 200 included an electrical circuit 201 coupled to a medical device 202. The electrical circuit 201 included an integrated tracking device 204 and imaging/visualizing device 206. In this example, the medical device 202 included a catheter, the tracking device 204 included a solenoid, the imaging/visualizing device 206 included a resonant loop, and the electrical circuit 201 comprising the tracking device 204 and the imaging/visualizing device 206 was incorporated onto the outer surface of the catheter. The multi-mode medical device system 200 was successfully tracked and, additionally, had a radially circular imaging sensitivity which was useful for vessel wall internal imaging and characterization of plaques in internal imaging mode, as well as suitable orientation in visualizing mode. The multi-mode medical device system 200 was tested in a phantom consisting of a vessel with a diameter of 25.4 mm in the center of the phantom filled with water.

The medical device 202 used in this example was a catheter, and particularly, was a FASGUIDE® hydrophilic catheter, available from Boston Scientific, having a length of 120 cm and diameter of 6 F. The electrical circuit 201 of the multi-mode medical device system 200 was formed of a 36 AWG magnet wire that was adhered to the outer wall of the catheter. The tracking device 204 formed a first portion of the electrical circuit 201 and, specifically, included a solenoid that was tightly wound around the outer surface of the tip of the catheter and comprised about 10-15 turns, with a length of about 1.5-2 mm and a diameter of about 1.5-2 mm. The imaging/visualizing device 206 formed a second portion of the electrical circuit 201, and included a resonant loop that was about 20-30 mm long and about 2-3 mm wide. The resonant loop was employed for visualizing the portion of the catheter to which the resonant loop was coupled or for MR internal imaging anatomical structures from the point of view of catheter. The electrical circuit 201 was longitudinally incorporated/fixed onto the catheter close to the distal end (i.e., tip) using super glue, and was connected to an MR scanner receiver channel using a shielded micro-coaxial cable 210 of 42 AWG (specifically, a half-wavelength (nλ/2) coaxial cable), which extended through the lumen of the catheter, as shown in FIG. 33. The catheter used included a double lumen, and the micro-coaxial cable 210 was positioned within one lumen of the catheter. Alternatively, the catheter could include additional lumens, or the micro-coaxial cable 210 could have been run along the outer wall the catheter.

In this example, the tracking device 204, i.e., the solenoid, of the electrical circuit 201 was wound around an outer surface of the catheter, and the imaging/visualizing device 206, i.e., the resonant loop of the electrical circuit 201 was adhered to the outer surface of the catheter. The solenoid and the resonant loop were connected in series to form one integral tracking/imaging/visualizing circuit. However, it should be understood that the medical device 202, i.e., the catheter, could instead be manufactured such that the medical device 202 (e.g., the outer wall of the catheter) included the electrical circuit embedded or integrally formed therein. By manufacturing the medical device 202 in this way, the outer surface of the medical device 202, and any MR-visible coatings applied thereto, would not be compromised during placement of the electrical circuit 201 onto the medical device 202.

The imaging/visualizing device 206, i.e., the resonant loop, included a surface mounted capacitor 208 that was connected across the loop of the electrical circuit 201 (i.e., across the width of the catheter), and used to tune the imaging/visualizing device 206 to parallel resonance at the Larmor frequency. Tuning and matching of the resonant loop for the purpose of imaging was achieved using the surface mounted capacitor 208 in conjunction with the micro-coaxial cable 210 and a remote decoupling circuit 192 (see also FIGS. 32, 38 and 39) connected to the proximal end of the micro-coaxial cable 210.

Tracking Mode

The electrical circuit 201 of the multi-mode medical device system 200 was connected to the decoupling circuit 192 via the micro-coaxial cable 210, and the decoupling circuit 192 was connected to an MR receiver channel on a 1.5 T SIGNA® MR scanner (available from General Electric, Waukesha, Wis.). The micro-coaxial cable 210 at one end was electrically coupled (e.g., by soldering) to the electrical circuit 201, and at the other end was electrically connected to the decoupling circuit 192. It should be understood to those of ordinary skill in the art that other electrical connections or couplings (including hard-wired and wireless connections) can be used to electrically couple the electrical circuit 201, the micro-coaxial cable 210, and/or the decoupling circuit 192 to the MR scanner.

In the tracking mode of the multi-mode medical device system 200, employing the tracking device 204, a spatially non-selective RF pulse and a readout gradient along a single axis were applied. Due to the localized spatial sensitivity of the solenoid, a sharp peak was observed in a Fourier-transformed signal, as shown in FIG. 35. The position of the peak corresponds to the location of the tracking device 204 (i.e., the solenoid located at the tip of the catheter in this example) along the axis. FIG. 36 illustrates a representation of the profile of the multi-mode medical device system 200. The narrow peak in the Fourier-transformed signal shown in FIG. 36 is due to the tracking device 204, and a perspective view of the multi-mode medical device system 200 has been lined up with the Fourier-transformed signal in FIG. 36 to illustrate this. The RF pulse and readout gradient was repeated for the remaining two axes to obtain the 3-dimensional position of the coil with a frequency of up to 20 Hz. As shown in FIG. 37, this coordinate information was then superimposed as an icon 211 on a previously acquired roadmap image. Tip tracking locations were obtained using a 2D gradient-recalled echo (GRE) sequence. Typical scan parameters for 2D GRE sequence were: TR=8 ms, TE=3 ms. acquisition matrix=256× 256, FOV=32 cm×32 cm, slice thickness=5 mm, and flip angle=30°.

Internal Imaging Mode

In the imaging mode of the multi-mode medical device system 200, employing the imaging/visualizing device 206, and particularly, the resonant loop portion of the electrical circuit 201, the resonant loop was tuned to resonate at the Larmor frequency (i.e., by choosing an appropriate capacitance for the capacitor 208). The parallel resonant loop was connected to the MR scanner via the micro-coaxial cable 210 and the remote decoupling circuit 192. The specific remote decoupling circuit 192a used in this example is illustrated in FIGS. 38 and 39. The decoupling circuit 192a included a matching circuit or network 250, and a decoupling network 252. The decoupling circuit 192a also included a signal path 251 from the imaging/visualizing device 206 to the receive chain of the MR scanner. The direction of current in the signal path 251 is illustrated by the arrows in FIGS. 38 and 39. The decoupling circuit 192a further included an RF path 254, a DC path 256, and an RF and DC path ("RF+DC path") 258. The RF path 254 was bounded on each side by a DC block capacitor (DCB) 255. The DC path 256 was bounded on each side by an RF choke ("RFC") 257.

The matching network 250 used included a π (pi) network, which included the parallel resonant loop capacitor 208 (shown in FIGS. 33 and 34), the micro-coaxial cable 210 in series with an inductor 260, and another parallel capacitor 262. Part of the matching network 250 was contained in the decoupling circuit 192a, and particularly, in the RF path 254 of the decoupling circuit 192a. The solenoid of the tracking device 204 was tuned to parallel resonance at the Larmor frequency with the capacitor 208. This created a high impedance at the terminals of the imaging/visualizing device 206. This impedance was then transferred to the decoupling circuit 192a by the micro-coaxial cable 210. The matching network 252 (i.e., parallel capacitor 208—series inductor 260—parallel capacitor 262) was implemented to match the high impedance of the imaging/visualizing device 206 to the MR scanner impedance of 50Ω to achieve maximum transfer of signal from the imaging/visualizing device 206 to the MR scanner.

The decoupling network 252 was used to decouple the imaging/visualizing device 206 of the multi-mode medical device system 200 from an external RF coil (e.g., either of the RF transmit coils 91 or 191 of FIGS. 31 and 32) during the transmit cycle. Decoupling was achieved by activating a PIN diode switch 264 that switched a capacitor 266 across the series inductor 260 when an appropriate DC bias was applied to the PIN diode switch 264. The value of the capacitor 266 was chosen such that it formed a parallel resonant tank circuit which acted essentially as a high resistance placed in series with the signal path 251 from the imaging/visualizing device 206. The DC bias to the PIN diode switch 264 was only applied during the transmit cycle of the MR scanner to block the relatively large RF signal induced in the imaging/visualizing device 206 by an external transmit coil. The decoupling network 252 was thus used to protect sensitive downstream circuits in the receive chain of the MR scanner.

Sagittal and Axial images obtained using a 2D steady state free precession (SSFP) sequence are shown in FIG. 40 and FIG. 41, respectively. Typical scan parameters for 2D SSFP sequence were: TR=16 ms, TE=3 ms. acquisition matrix=256×256, FOV=14 cm×14 cm, slice thickness=5 mm, and flip angle=50°.

Visualizing Mode

In the visualizing (or wireless marker) mode of the multi-mode medical device system 200, employing the imaging/ visualizing device 206, and particularly, the resonant loop portion of the electrical circuit 201, the electrical circuit 201 was disconnected from the MR scanner. Therefore, the imaging/visualizing device 206 (i.e., the resonant loop) was inductively coupled to an external RF coil. The signal generated by the resonant loop (also referred to herein as an "inductively coupled resonator") was picked up by the external RF coil. A snapshot coronal image of the multi-mode medical device system 200 obtained using the resonant loop portion of the electrical circuit 201 is shown in FIG. 42. The image in FIG. 42 was obtained using a 2D steady state free precession (SSFP). Note that not only the resonant loop portion of the electrical circuit 201 was visible in the visualizing mode, but also the entire length of the micro-coaxial cable 210 was visible as well. Typical scan parameters for 2D SSFP sequence were: TR=7.4 ms, TE=2.5 ms. acquisition matrix=256×256, FOV=20 cm×20 cm, slice thickness=20 mm, and flip angle=6°.

Example 17

A Multi-Mode Medical Device System Having Tracking, Internal Imaging, and Visualizing Capabilities, and Including an MR-Visible Coating The multi-mode medical device system of this example includes all of the elements of the multi-mode medical device system 200 described in Example 16 above, with an MR-visible coating 212 applied to the surface of the medical device 202 (i.e., the catheter). By way of example only, the MR-visible coating 212 is illustrated in FIG. 34. The MR-visible coating 212 can be applied to the outer surface of the catheter along the length of the catheter, or a portion thereof, to allow the respective portion of the catheter to be visualized under MR guidance. In addition, the MR-visible coating 212 can act as an internal signal source for the tracking device 204 and the imaging/visualizing device 206 of the multi-mode medical device system 200. The MR-visible coating 212 allows the catheter, and any nonlinear configurations thereof, to be visualized during the visualizing mode of the multi-mode medical device system 200. The MR-visible coating 212 can be applied to the surface of the catheter before, during or after the electrical circuit 201 is coupled to the catheter.

Example 18

Figure 43:
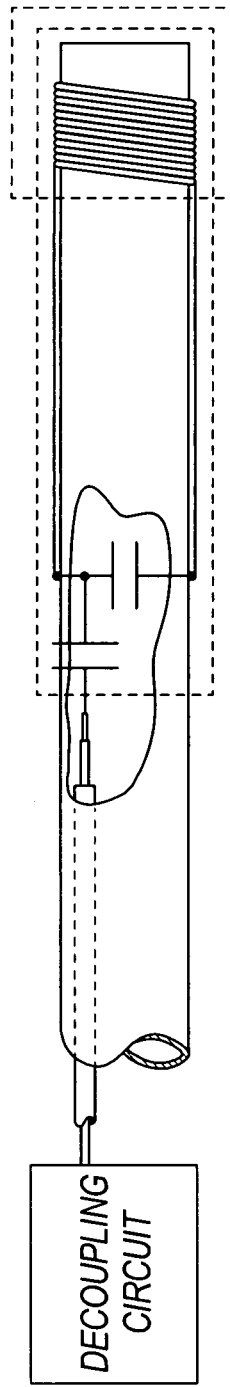
FIG. 43 is a partially schematic cut-away view of a multi-mode medical device system according to another embodiment of the present invention, described in Example 18, the multi-mode medical device system shown electrically coupled to a decoupling circuit.

A Multi-Mode Medical Device System Having Tracking, Internal Imaging, and Visualizing Capabilities A multi-mode medical device system 300 according to this example, and one embodiment of the present invention, is shown in FIG. 43. The multi-mode medical device system 300 included an electrical circuit 301 coupled to a medical device 302. The electrical circuit 301 included an integrated tracking device 304 and imaging/visualizing device 306. In this example, the medical device 302, the electrical circuit 301, the tracking device 304 and the imaging/visualizing device 306 were substantially the same as that described above in Example 16, except that the catheter used was an XXL® hydrophilic catheter, available from Boston Scientific, having a length of 120 cm and diameter of 6 F. In addition, the electrical circuit 301 was connected to a receiver channel of a 1.5 T SIGNA® MR scanner (available from General Electric, Waukesha, Wis.) via a shielded micro-coaxial cable 310, which was the same micro-coaxial cable as that described in Example 16. The micro-coaxial cable 310 extended through the lumen of the catheter, as shown in FIG. 43.

The imaging/visualizing device 306, i.e., the resonant loop, included a surface mounted capacitor 308 connected across the loop of the electrical circuit 301 and used to tune the imaging/visualizing device 306 to resonate at the Larmor frequency (i.e., 64 MHz) of the 1.5 T SIGNA® MR scanner. As shown in FIG. 43, a surface mounted capacitor 309 was connected in series between the resonant loop and the micro-coaxial cable 310 for matching. The capacitor 308 served as a tuning capacitor 308, and the capacitor 309 served as a matching capacitor 209 for tuning and matching of the resonant loop. A remote decoupling circuit 192b was connected to the proximal end of the micro-coaxial cable 310 was used to block the large signal induced in the imaging/visualizing device 306 during a transmit cycle of the MR scanner, thus protecting sensitive downstream circuitry in the receive chain.

Tracking Mode

Figure 46:
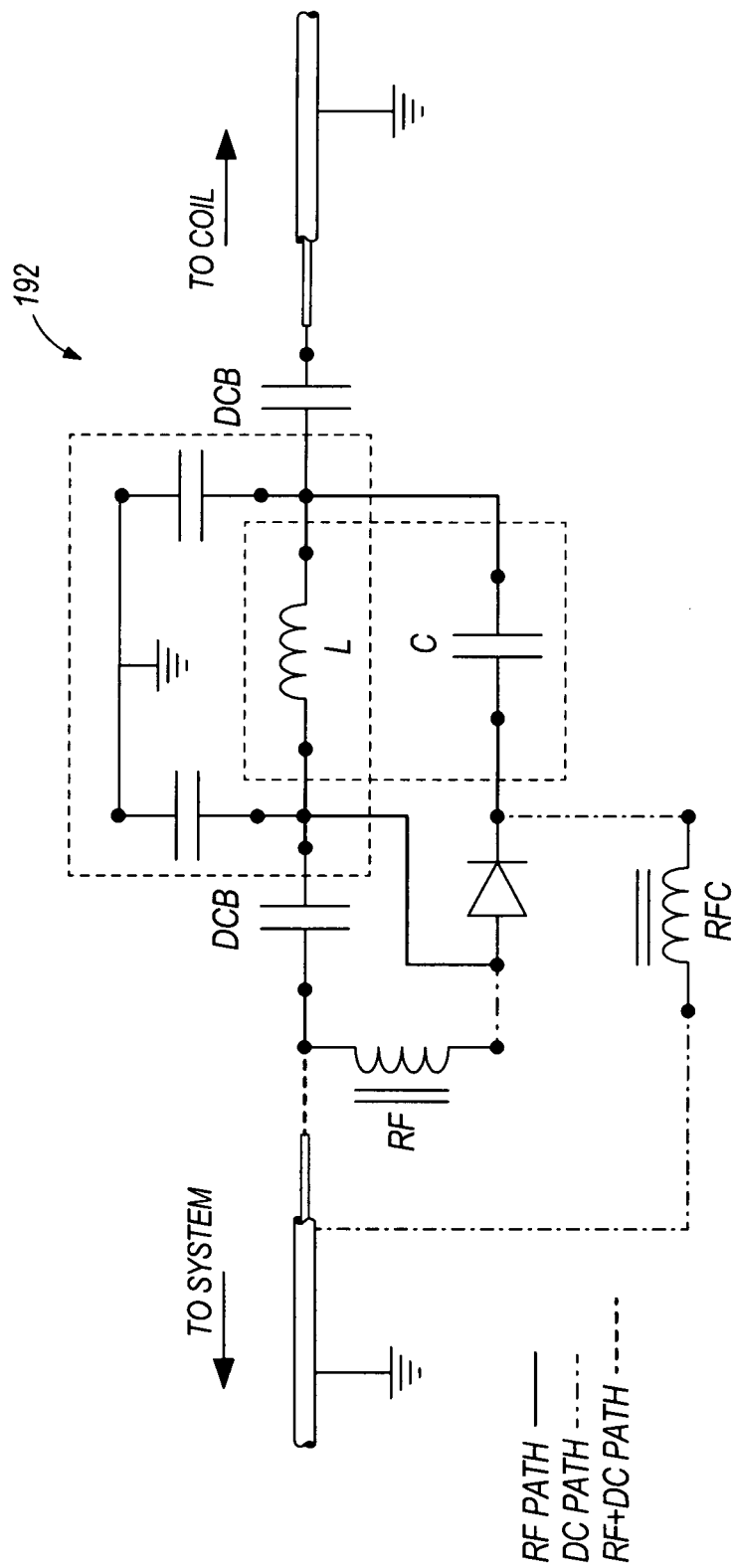
FIG. 46 is a schematic representation of a decoupling circuit according to another embodiment of the present invention, described in Example 18.
Figure 47:
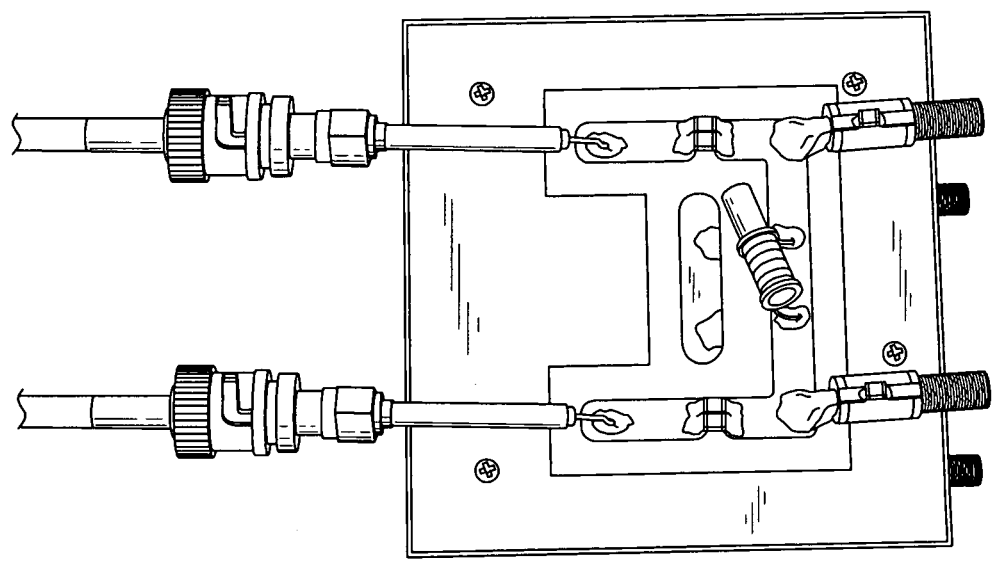
FIG. 47 is a top perspective view of one embodiment of the decoupling circuit of FIG. 46.
Figure 48:
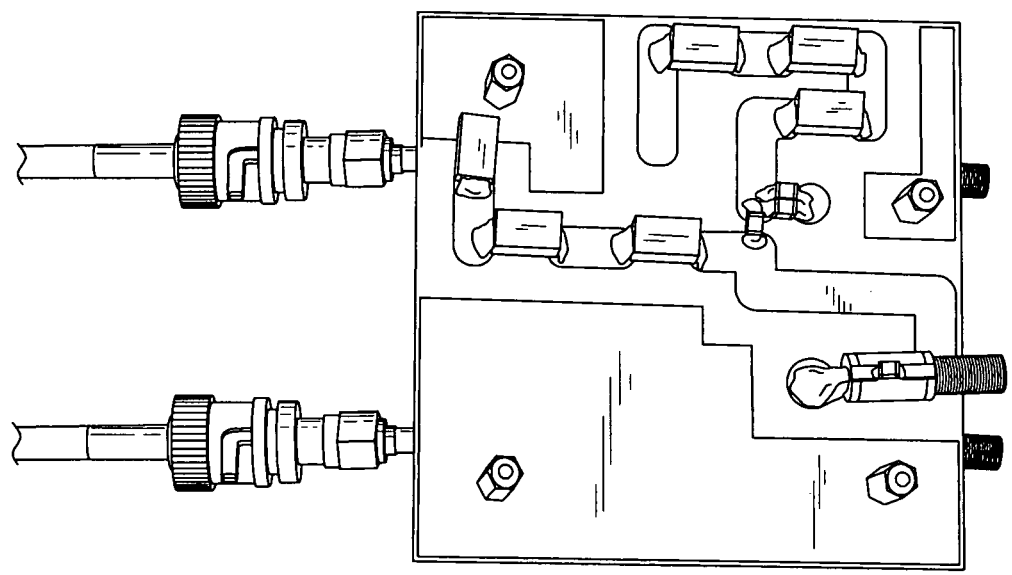
FIG. 48 is a bottom perspective view of the decoupling circuit of FIGS. 46 and 47.

The electrical circuit 301 of the multi-mode medical device system 300 was connected to the decoupling circuit 192b, shown in FIGS. 46-48, via the micro-coaxial cable 310, and the decoupling circuit 192b was connected to an MR receiver channel on a 1.5 T SIGNA® MR scanner (available from General Electric, Waukesha, Wis.).

In the tracking mode of the multi-mode medical device system 300, employing the tracking device 304, a spatially non-selective RF pulse and a readout gradient along a single axis were applied. Due to the localized spatial sensitivity of the solenoid, a sharp peak was observed in a Fourier-transformed signal, as shown in FIG. 44. The position of the peak corresponds to the location of the tracking device 304 (i.e., the solenoid located at the tip of the catheter in this example) along the axis. The RF pulse and readout gradient was repeated for the remaining two axes to obtain the 3-dimensional position of the coil with a frequency of up to 20 Hz. As shown in FIG. 45, this coordinate information was then superimposed as an icon 311 on a previously acquired roadmap image. Tip tracking locations were obtained using a 2D gradient-recalled echo (GRE) sequence. Typical scan parameters for 2D GRE sequence were: TR=8 ms, TE=3 ms. acquisition matrix=256×256, FOV=32 cm×32 cm, slice thickness=5 mm, and flip angle=30°.

Internal Imaging Mode

In the internal imaging mode of the multi-mode medical device system 300, employing the imaging/visualizing device 306, and particularly, the resonant loop portion of the electrical circuit 301, the resonant loop was tuned to resonate at the Larmor frequency (i.e., by choosing an appropriate capacitance for capacitor 308). The parallel resonant loop was connected to the MR scanner via the micro-coaxial cable 310 and the remote decoupling circuit 192b. As shown in FIGS. 46-48, the decoupling circuit 192b included a 50Ω lumped element transmission line section 353, and a decoupling network 352. The decoupling circuit 192b also included a signal path 351 from the imaging/visualizing device 306 to the receive chain of the MR scanner. The direction of current in the signal path 351 is illustrated by the arrows in FIGS. 46-48. The decoupling circuit 192b further included an RF path 354, a DC path 356, and an RF and DC path ("RF+DC path") 358. The RF path 354 was bounded by three DC block capacitors (DCB) 355. The DC path 356 was bounded on each side by an RF choke ("RFC") 357.

The matching network 350 was implemented at the terminals of the imaging/visualizing device 306 with the matching capacitor 309. The matching network 350 transformed the impedance of the imaging/visualizing device 306 to the MR scanner impedance of 50Ω to achieve maximum transfer of signal from the imaging/visualizing device 306 to the MR scanner. The decoupling mechanism of the decoupling network 352 was the same as that described in Example 16, wherein like numerals represent like elements. The only difference between the decoupling circuit 192a of Example 16 and the decoupling circuit 192b used in this example was that the matching network 250 of the decoupling circuit 192a was replaced by a 50Ω lumped element transmission line section 353 in the decoupling circuit 192b. In other words, because the matching network 350 was moved upstream to the terminals of the imaging/visualizing device 306 (i.e., with the matching capacitor 309), the same components that formed the matching network 250 of Example 16 were used in this example to form a portion of the 50Ω lumped element transmission line section 353. The 50Ω lumped element transmission line section 353 included the same pi configuration as that of the matching network 250 in Example 16, but the 50Ω lumped element transmission line section 353 included two capacitors 362 connected in parallel with an in-series inductor 360. The 50Ω lumped element transmission line section 353 provided the series components necessary for the decoupling network 352, namely, the series inductor 360. The capacitors 362 of the 50Ω lumped element transmission line section 353 provided the appropriate impedance compensation for the inductor 360 of the decoupling network 352. Thus, the 50Ω lumped element transmission line section 353 achieved a greater signal-to-noise ratio (SNR) from the imaging device 306 by maintaining the 50Ω impedance necessary to match that of the MRI system. The pi configuration of the 50Ω lumped element transmission line section 353 was used to demonstrate one type of controlled impedance path that could be used in the decoupling circuit 192b, and is described and shown here by way of example only.

Figure 49:
FIG. 49 is a sagittal image of a phantom, obtained using an imaging device during an internal imaging mode of the multi-mode medical device system of FIG. 43, described in Example 18.
Figure 50:
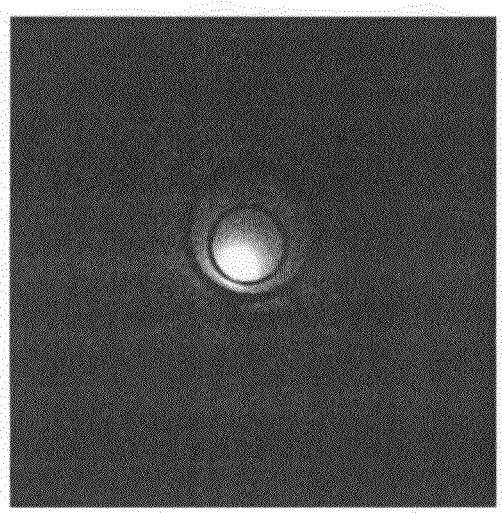
FIG. 50 is an axial image of a phantom, obtained using an imaging device during an internal imaging mode of the multi-mode medical device system of FIG. 43, described in Example 18.

Sagittal and Axial images obtained using a 2D steady state free precession (SSFP) sequence are shown in FIG. 49 and FIG. 50, respectively. Typical scan parameters for 2D SSFP sequence were: TR=16 ms, TE=3 ms. acquisition matrix=256×256, FOV=14 cm×14 cm, slice thickness=5 mm, and flip angle=50°.

Visualizing Mode

In the visualizing mode of the multi-mode medical device system 300, employing the imaging/visualizing device 306, and particularly, the resonant loop portion of the electrical circuit 301, the electrical circuit 301 was disconnected from the MR scanner. Therefore, the imaging/visualizing device 306 was inductively coupled to an external RF coil. The signal generated by the resonant loop was picked up by the external RF coil. A snapshot coronal image of the multi-mode medical device system 300 obtained using the resonant loop portion of the electrical circuit 301 is shown in FIG. 51. The image in FIG. 51 was obtained using a 2D steady state free precession (SSFP). Note that not only the resonant loop portion of the electrical circuit 301 was visible in the visualizing mode, but also the entire length of the micro-coaxial cable 310 was visible as well. Typical scan parameters for 2D SSFP sequence were: TR=7.4 ms, TE=2.5 ms. acquisition matrix=256×256, FOV=20 cm×20 cm, slice thickness=20 mm, and flip angle=6°.

Example 19

Figure 52:
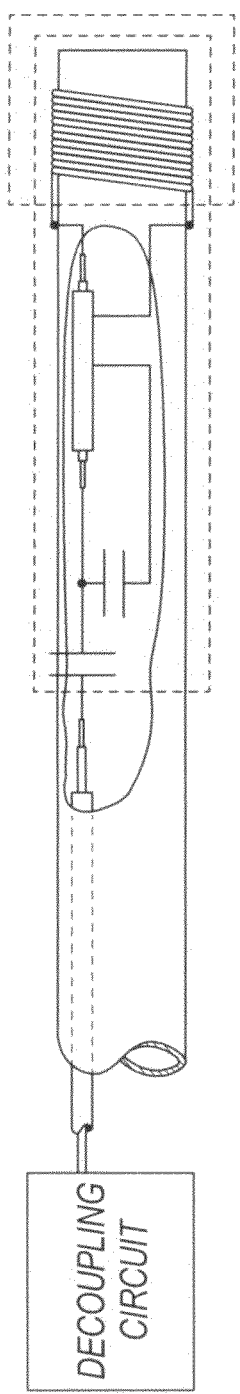
FIG. 52 is a partially schematic cut-away view of a multi-mode medical device system according to another embodiment of the present invention, described in Example 19, the multi-mode medical device system shown electrically coupled to a decoupling circuit.

A Multi-Mode Medical Device System Having Tracking, Internal Imaging, and Visualizing Capabilities A multi-mode medical device system 400 according to this example, and one embodiment of the present invention, is shown in FIG. 52. The multi-mode medical device system 400 included an electrical circuit 401 coupled to a medical device 402. The multi-mode medical device system 400 is similar to the multi-mode medical device system 300 described in Example 18, wherein like numerals represent like elements. The multi-mode medical device system 400 included an electrical circuit 401 that included a tracking device 404, and an imaging/visualizing device 406, as described in Example 18. The multi-mode medical device system 400 further included a tuning capacitor 408, a matching capacitor 409, and a micro-coaxial cable 410, similar to that described in Example 18. In addition, the same decoupling circuit 192b was connected to the multi-mode medical device system 400 via the micro-coaxial cable 410.

The electrical circuit 401 included an integrated tracking device 404 and imaging/visualizing device 406. However, the multi-mode medical device system 400 included an extension micro-coaxial cable 470 that connected the tracking device 404 and the imaging/visualizing device 406 such that the tracking device 404 would be spatially disposed from the imaging/visualizing device 406 along the length of the catheter, as shown in FIG. 52. The extension micro-coaxial cable 470 used in this example was 15 millimeters in length. However, it should be understood that varying lengths of the extension micro-coaxial cable 470 can be used without departing from the spirit and scope of the present invention.

Internal Imaging Mode

In the internal imaging mode of the multi-mode medical device system 400, employing the imaging/visualizing device 406, and particularly, the resonant loop portion of the electrical circuit 401, the resonant loop was tuned to resonate at the Larmor frequency (i.e., by choosing an appropriate capacitance for capacitor 408). The parallel resonant loop was connected to the MR scanner via the micro-coaxial cable 410 and the decoupling circuit 192b illustrated in FIGS. 46-48.

Figure 53:
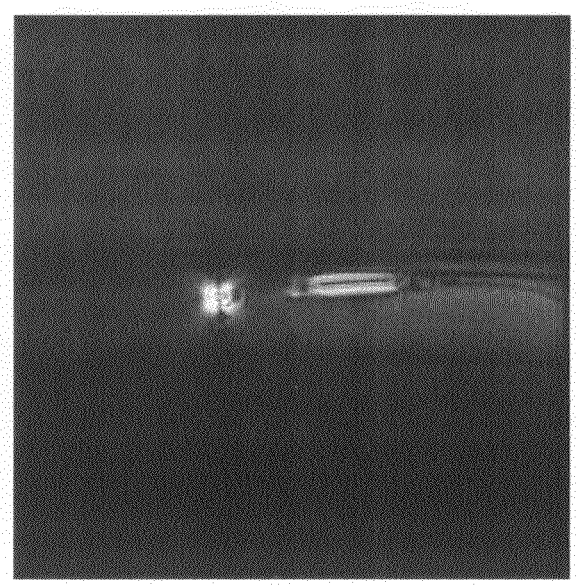
FIG. 53 is a sagittal image of a phantom, obtained using an imaging device during an internal imaging mode of the multi-mode medical device system of FIG. 52, described in Example 19.
Figure 54:
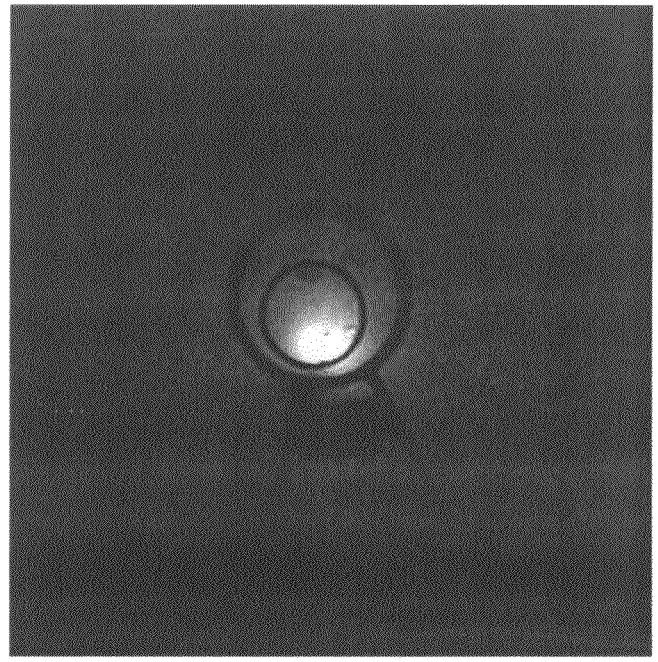
FIG. 54 is an axial image of a phantom, obtained using an imaging device during an internal imaging mode of the multi-mode medical device system of FIG. 52, described in Example 19.

Sagittal and Axial images obtained using a 2D steady state free precession (SSFP) sequence are shown in FIG. 53 and FIG. 54, respectively. Typical scan parameters for 2D SSFP sequence were: TR=16 ms, TE=3 ms. acquisition matrix=256×256, FOV=14 cm×14 cm, slice thickness=5 mm, and flip angle=50°. As shown in FIG. 53, the imaging/visualizing device 406 imaged a first portion 472 of the phantom, corresponding to the position of the solenoid and disposed a distance from a second portion 474 of the phantom, corresponding to the position of the remainder of the resonant loop. The distance between the first portion and second portion being due to the extension micro-coaxial cable 470.

Visualizing Mode

In the visualizing mode of the multi-mode medical device system 400, employing the imaging/visualizing device 406, and particularly, the resonant loop portion of the electrical circuit 401, the electrical circuit 401 was disconnected from the MR scanner. Therefore, the imaging/visualizing device 406 was inductively coupled to an external RF coil. The signal generated by the resonant loop was picked up by the external RF coil. A snapshot coronal image of the multi-mode medical device system 400 obtained using the resonant loop portion of the electrical circuit 401 is shown in FIG. 55. The image in FIG. 55 was obtained using a 2D steady state free precession (SSFP). Note that a first portion 476 of the multi-mode medical device system 400 corresponding to the solenoid and a second portion 478 of the multi-mode medical device system 400 disposed a distance from the first portion 476 and corresponding the resonant loop were both visible in the visualizing mode. The distance, or void, visible between the first portion 476 and the second portion 478 was due to the extension micro-coaxial cable 470. Typical scan parameters for 2D SSFP sequence were: TR=7.4 ms, TE=2.5 ms. acquisition matrix=256×256, FOV=20 cm×20 cm, slice thickness=20 mm, and flip angle=6°.

Example 20

A Multi-Mode Medical Device System Having Tracking, Internal Imaging, Visualizing, and Forward-Looking Capability A multi-mode medical device system according to this example, and one embodiment of the present invention, is shown in FIG. 56. The multi-mode medical device system 500 included an electrical circuit 504 coupled to a medical device 502. The electrical circuit 504 included a tracking device 506 and an imaging/visualizing device 508. In this example, the medical device 502 included a catheter, the tracking device 506 included a Helmholtz pair, and the imaging/visualizing device 508 included an imaging loop. The electrical circuit 504 comprising the tracking device 506 and the imaging/visualizing device 508 was incorporated onto the outer surface 512 of the catheter. The multi-mode medical device system 500 further included a pi matching network 520 and was connected to a micro-coaxial cable.

The multi-mode medical device system 500 operated substantially similar to the multi-mode medical device system described above in Example 16.

The tracking device 506 was constructed on a modified 6 F (2 mm outer diameter) double lumen balloon catheter using 36 gauge wire. The tracking device 506 included an 8-turn Helmholtz pair placed at the distal end 514 of the catheter 502 and connected in series with a 2-turn imaging loop 508 as illustrated in FIG. 56. The imaging loop 508 was 20 mm long, spanned the outer diameter of the catheter 502 and was wound in a sense opposite to that of the Helmholtz pair.

A voltage standing wave suppression device 550 was implemented by forming cable traps comprising 70 tightly wound turns of the imaging loop 508 around the catheter. A first or distal cable trap 554 was placed close to and proximally to the tracking device 506. Another similar cable trap was placed towards the proximal end of the catheter 502. This was done to prevent the formation of voltage standing waves induced on the coaxial cable shield.

While the present invention has now been described and exemplified with some specificity, those skilled in the art will appreciate the various modifications, including variations, additions, and omissions, which may be made in what has been described. Accordingly, it is intended that these modifications also be encompassed by the present invention and that the scope of the present invention be limited solely by the broadest interpretation that can lawfully be accorded the appended claims. All printed publications, patents and patent applications referred to herein are hereby fully incorporated by reference.

Various features and advantages of the invention are set forth in the following claims.

What is claimed is:

1. A medical system comprising: a flexible catheter having a proximal end and a distal end and comprising:
    a flexible tubular wall having an interior surface defining a lumen extending along a longitudinal axis and an exterior surface coaxially exposed outside the flexible tubular wall and separated from the interior surface by a wall thickness, between the distal end and the proximal end;
    an antenna coil device coupled to the exterior surface adjacent the distal end of the flexible catheter, the antenna coil device having a tracking portion and an imaging portion, the tracking portion providing localized spatial sensitivity relative to the imaging portion, the tracking portion and imaging portion connected together to transmit a combined signal, the combined signal simultaneously comprising a tracking signal and an imaging signal, the combined signal being of a character so that the imaging signal may be distinguished from the tracking signal after their combination at an imaging system to generate an image of a field-of-view forward of the distal end and to generate a location of the distal end;
    a conductive member electrically coupled to the antenna coil device adapted to transmit the combined signal therein, and extending to the proximal end of the flexible catheter along the exterior surface;
    a proximal cable trap and a distal cable trap electrically coupled to the conductive member, wherein the proximal cable trap and distal cable trap are located on the exterior surface of the flexible tubular wall, the proximal cable trap and a distal cable trap adapted to suppress the formation of standing voltage waves at the conductive member;
    whereby the lumen may pass a therapeutic device therein from the proximal end to the distal end without interference from the cable trap or antenna coil device.

2. The medical system of claim 1, wherein a distance between the proximal cable trap and the distal cable trap is substantially half of a length of the flexible catheter.

3. The medical system of claim 1, wherein the signal has a frequency F and a corresponding wavelength WL, wherein a distance between the proximal cable trap and the distal cable trap is less than substantially one fifth WL.

4. The medical system of claim 3, wherein the distance between the proximal cable trap and the distal cable trap is substantially one tenth WL.

5. The medical system of claim 1, further comprising an intermediate cable trap evenly spaced between the proximal and distal cable traps.

6. The medical system of claim 1, wherein the proximal and distal cable traps each comprise a coiled region of the conductive member having tightly packed coil turns.

7. The medical system of claim 6, wherein the coiled region has from substantially 70 to 75 coil turns.

8. The medical system of claim 1, wherein the antenna coil device further comprises an imaging loop located on the exterior surface of the distal end of the flexible tubular wall and electrically coupled to the conductive member, the imaging device being adapted to transmit a signal to the imaging system to generate an image from a point of view of the flexible catheter.

9. The medical system of claim 1, further comprising an MR-visible coating applied to at least a portion of the exterior surface of the flexible tubular wall of the flexible catheter to allow the respective portion of the flexible catheter to be visualized using magnetic resonance imaging, wherein the MR-visible coating includes at least one of a paramagnetic-metal-ion/ligand complex, a paramagnetic-metal-ion/chelate complex, a cross-linker, a hydrogel, and combinations thereof.

10. A medical system comprising: a flexible catheter having a proximal end and a distal end and comprising:
    a flexible tubular wall having an interior surface defining a lumen extending along a longitudinal axis and an exterior surface coaxially exposed outside the flexible tubular wall and separated from the interior surface by a wall thickness, between the distal end and the proximal end;
    an antenna coil device coupled to the exterior surface of the flexible tubular wall adjacent the distal end of the flexible catheter, the antenna coil device having a tracking portion and an imaging portion, the tracking portion providing localized spatial sensitivity relative to the imaging portion, the tracking portion and imaging portion connected together to transmit combined signal, the combined signal simultaneously comprising a tracking signal and a imaging signal, the combined signal being of a character so that the imaging signal may be distinguished from the tracking signal after their combination at an imaging system to generate an imaging field-of-view forward of the distal end and a location of the distal end;
    a conductive member electrically coupled to the antenna coil device and extending to the proximal end of the flexible catheter along the exterior surface of the flexible tubular wall; and
    a voltage standing wave suppression device on the exterior surface of the exterior surface of the flexible tubular wall;
    whereby the lumen may pass a therapeutic device therein from the proximal end to the distal end without interference from the cable trap or antenna coil device.

11. The medical system of claim 10, wherein the voltage standing wave suppression device is adapted to block a common mode signal induced on the exterior surface of the flexible tubular wall and transmit the imaging signal.

12. The medical system of claim 10, wherein the voltage standing wave suppression device comprises spaced apart first and second coiled regions of the conductive member.

13. The medical system of claim 12, wherein the flexible catheter has a length defined by the distance between the distal and proximal ends, and wherein a distance between the first coiled region and the second coiled region is substantially half of the length of the flexible catheter.

14. The medical system of claim 12, wherein the imaging signal has a frequency F and a corresponding wavelength WL, wherein a distance between the first coiled region and the second coiled region is less than substantially one fifth WL.

15. The medical system of claim 14, wherein the distance between the first coiled region and the second coiled region is substantially one tenth WL.

16. The medical system of claim 12, wherein each coiled region has from substantially 70 to 75 coil turns.

17. The medical system of claim 10, wherein the antenna coil device further comprises an imaging loop located on the exterior surface of the distal end of the flexible tubular wall and electrically coupled to the conductive member, the imaging device being adapted to transmit a signal to the imaging system to generate an image from a point of view of the flexible catheter.

18. The medical system of claim 10, further comprising an MR-visible coating applied to at least a portion of the exterior surface of the flexible tubular wall of the flexible catheter to allow the respective portion of the flexible catheter to be visualized using magnetic resonance imaging, wherein the MR-visible coating includes at least one of a paramagnetic-metal-ion/ligand complex, a paramagnetic-metal-ion/chelate complex, a cross-linker, a hydrogel, and combinations thereof.

19. A medical system comprising: a flexible catheter having a proximal end and a distal end and further comprising:
a flexible tubular wall having an interior surface defining a lumen extending along a longitudinal axis and an exterior surface coaxially exposed outside the flexible tubular wall and separated from the interior surface by a wall thickness between the distal end and the proximal end;
an imaging device adjacent to the distal end of the flexible tubular wall and configured to generate an image from a point of view of the distal end of the flexible catheter;
a tracking device adjacent to the distal end of the flexible tubular wall and configured to generate a location of the distal end of the flexible catheter, the tracking device providing localized spatial sensitivity relative to the imaging device;
a conductive member electrically coupled to the imaging device and the tracking device and extending to the proximal end of the flexible catheter along the exterior surface of the flexible tubular wall, the conductive member adapted to transmit a combined signal from the imaging device and tracking device therealong, the combined signal simultaneously comprising a tracking signal and an imaging signal and being of a character so that the imaging signal may be distinguished from the tracking signal after their combination;
a proximal cable trap and a distal cable trap electrically coupled to the conductive member, and located on the exterior surface of the flexible tubular wall; and
whereby the lumen may pass a therapeutic device therein from the proximal end to the distal end without interference from the cable trap or an antenna coil.

20. The medical system of claim 19, further comprising an MR-visible coating applied to at least a portion of the exterior surface of the flexible tubular wall of the flexible catheter to allow the respective portion of the flexible catheter to be visualized using magnetic resonance imaging, wherein the MR-visible coating includes at least one of a paramagnetic-metal-ion/ligand complex, a paramagnetic-metal-ion/chelate complex, a cross-linker, a hydrogel, and combinations thereof.

21. A method of performing an interventional procedure using an imaging system, the method comprising: moving a flexible multi-mode catheter toward a target area; transmitting a combined signal from a distal end of the flexible multi-mode catheter to a proximal end of the flexible multi-mode catheter along an outer surface of the multi-mode catheter, the combined signal simultaneously comprising an imaging signal and a tracking signal, and being of a character so that the imaging signal may be distinguished from the tracking signal after their combination; and suppressing a common mode signal on the exterior surface of the flexible multi-mode catheter.

22. The method of claim 21, wherein the flexible multi-mode catheter comprises a flexible tubular wall having an interior surface defining a lumen configured to receive a therapeutic device, the lumen extending along a longitudinal axis of the flexible tubular wall, the catheter having a length defined by the distance between the distal and proximal ends, and wherein suppressing the common mode signal further comprises providing a distal cable trap on an exterior surface coaxially exposed outside the inner wall and separated from an inner wall by a wall thickness of a distal end of the flexible multi-mode catheter and a proximal cable trap on the exterior surface of a proximal end of the flexible multi-mode catheter, the proximal cable trap being spaced apart from the distal cable trap by a distance D, wherein D is substantially one half the length of the flexible multi-mode catheter.

23. The method of claim 21, wherein the imaging signal comprises a wavelength, and wherein suppressing the common mode signal further comprises providing a distal cable trap on the exterior surface of the distal end of the flexible multi-mode catheter and a proximal cable trap on the exterior surface of the proximal end of the flexible multi-mode catheter, the proximal cable trap being spaced apart from the distal cable trap by a distance D, wherein D is substantially one tenth of the wavelength of the imaging signal.

24. The method of claim 21, further comprising generating an image from a point-of-view of the flexible multi-mode catheter.

25. The method of claim 21, further comprising generating an image of the target area that lies within an image field forward of the distal end of the flexible multi-mode catheter.

26. A medical system comprising: a flexible catheter having a proximal end and a distal end and further comprising:
a flexible tubular wall having an interior surface defining a lumen extending along a longitudinal axis and an exterior surface coaxially exposed outside the flexible tubular wall and separated from the interior surface by a wall thickness, between the distal end and the proximal end;
a antenna coil device coupled to the exterior surface of the flexible tubular wall adjacent the distal end of the flexible catheter, the antenna coil device having a tracking portion and an imaging portion, the tracking portion providing localized spatial sensitivity relative to the imaging portion, the tracking portion and imaging portion connected together to transmit a combined signal to an imaging system to generate an image field forward of the distal end, the combined signal simultaneously comprising an imaging signal and a tracking signal, and the combined signal being of a character so that the imaging signal may be distinguished from the tracking signal after their combination;
an imaging device electrically coupled to the antenna coil device, the imaging device being adapted to transmit the image signal to the imaging system to generate an image from a point of view of the flexible catheter;
a tracking device electrically coupled to the antenna coil device, the tracking device being adapted to transmit the tracking signal to the imaging device to generate a location of the distal end of the flexible catheter;
an MR-visible coating applied to at least a portion of the exterior surface of the flexible tubular wall to allow the respective portion of the flexible catheter to be visualized using magnetic resonance imaging, wherein the MR-visible coating includes at least one of a paramagnetic-metal-ion/ligand complex, a paramagnetic-metal-ion/chelate complex, a cross-linker, a hydrogel, and combinations thereof; and
a proximal cable trap and a distal cable trap electrically coupled to the imaging device, and on the exterior surface of the flexible tubular wall, and wherein the proximal cable trap and a distal cable trap suppress the formation of standing voltage waves at the conductive member;
whereby the lumen may pass a therapeutic device therein from the proximal end to the distal end without interference from the cable trap or antenna coil device.

27. A medical system comprising: a flexible catheter having a proximal end and a distal end and further comprising:

a flexible tubular wall having an interior surface defining a lumen extending along a longitudinal axis and an exterior surface coaxially exposed outside the inner wall and separated from the inner wall by a wall thickness, between the distal end and proximal end, the flexible catheter being adapted for use within an external field;

a co-axial conductive member extending from the distal end of the flexible catheter to the proximal end of the flexible catheter, along the exterior surface of the flexible tubular wall, the co-axial conductive member adapted to transmitting a combined signal simultaneously comprising an imaging signal and a tracking signal, the combined signal being of a character so that the imaging signal may be distinguished from the tracking signal after their combination;

and a proximal cable trap and a distal cable trap coupled to the exterior surface of the flexible tubular wall, wherein the proximal cable trap and a distal cable trap suppress the formation of standing voltage waves at the co-axial conductive member; and whereby the lumen may pass a therapeutic device therein from the proximal end to the distal end without interference from the cable trap or an antenna coil.

28. The medical system of claim 27, wherein the flexible catheter comprises at least one of a flexible multi-mode catheter, or an endovascular delivery device.

29. The medical system of claim 27, wherein the flexible catheter is adapted for implantation during an MR procedure.

30. A medical system comprising: a flexible catheter having a proximal end and a distal end and further comprising:

a flexible tubular wall having an interior surface defining a lumen extending along a longitudinal axis and an exterior surface coaxially exposed outside the inner wall and separated from the inner wall by a wall thickness, between the distal end and proximal end, the flexible catheter being adapted for use within an external field;

a co-axial conductive member extending from the distal end of the flexible tubular wall to the proximal end of the flexible tubular wall along the exterior surface of the flexible tubular wall, the co-axial conductive member adapted to transmitting a combined signal simultaneously comprising an imaging signal and a tracking signal, the combined signal being of a character so that the imaging signal may be distinguished from the tracking signal after their combination;

a voltage standing wave suppression device coupled to the exterior surface of the flexible tubular wall; and the lumen configured to pass a therapeutic device therein from the proximal end to the distal end.

31. The medical system of claim 30, wherein the flexible catheter comprises at least one of a flexible multi-mode catheter-or an endovascular delivery device.

32. The medical system of claim 30, wherein the flexible catheter is adapted for implantation during an MR procedure.

* * * * *